US012799547B2

(12) United States Patent
Li et al.

(10) Patent No.: US 12,799,547 B2
(45) Date of Patent: Nov. 17, 2026

(54) RAPID MULTIPLEX RPA BASED NANOPORE SEQUENCING METHOD FOR REAL-TIME DETECTION AND SEQUENCING OF MULTIPLE VIRAL PATHOGENS

(71) Applicant: King Abdullah University of Science and Technology, Thuwal (SA)

(72) Inventors: Mo Li, Thuwal (SA); Chongwei Bi, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 851 days.

(21) Appl. No.: 18/001,365

(22) PCT Filed: Jun. 10, 2021

(86) PCT No.: PCT/IB2021/055127

§ 371 (c)(1),
(2) Date: Dec. 9, 2022

(87) PCT Pub. No.: WO2021/250617

PCT Pub. Date: Dec. 16, 2021

(65) Prior Publication Data

US 2024/0279751 A1 Aug. 22, 2024

Related U.S. Application Data

(60) Provisional application No. 63/163,227, filed on Mar. 19, 2021, provisional application No. 63/037,175, filed on Jun. 10, 2020.

(51) Int. Cl.
*C12Q 1/70* (2006.01)
*C12Q 1/68* (2018.01)
*C12Q 1/6844* (2018.01)

(52) U.S. Cl.
CPC ........... *C12Q 1/701* (2013.01); *C12Q 1/6844* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 11,149,320 | B1 * | 10/2021 | Brambati | C12Q 1/701 |
| 11,207,370 | B2 * | 12/2021 | Schinazi | C07K 5/0812 |
| 11,510,977 | B2 * | 11/2022 | Ying | A61K 39/12 |
| 11,713,491 | B2 * | 8/2023 | Kana | C12Q 1/6806 435/5 |
| 12,037,653 | B2 * | 7/2024 | Inchingolo | C12Q 1/701 |
| 12,077,758 | B2 * | 9/2024 | Khvorova | C12N 15/1131 |
| 2019/0360030 | A1 | 11/2019 | Piepenburg et al. | |
| 2023/0151441 | A1 * | 5/2023 | Zhang | C12Q 1/701 435/5 |

FOREIGN PATENT DOCUMENTS

| | | | |
|---|---|---|---|
| CN | 107287349 | A | 10/2017 |
| CN | 108192996 | A | 6/2018 |
| CN | 111187856 | A | 5/2020 |
| WO | 2005118853 | A2 | 12/2005 |
| WO | 2007096702 | A2 | 8/2007 |

OTHER PUBLICATIONS

Kim et al. (CellPress, May 14, 2020, p. 914-921).*
Pachetti et al. (Journal of Translational Medicine, Apr. 2020, pp. 1-9).*
Behrmann et al. (Clinical Chemistry, May 2020, p. 1047-1054).*
Yan et al. (Clinical Microbiology and Infection, Apr. 8, 2020, p. 773-779).*
"An Outbreak of NCIP (2019-nCOV) Infection in China—Wuhan, Hubei Province, 2019-2020", The 2019-nCOV Outbreak Joint Field Epidemiology Investigation Team, China CDC Weekly, vol. 2, No. 5, Jan. 31, 2020, pp. 79-80.
"Clinical and Virologic Characteristics of the First 12 Patients with Coronavirus Disease 2019 (COVID-19) in the United States", The COVID-19 Investigation Team, Nature Medicine, vol. 26, 2020, pp. 861-868.
International Preliminary Report on Patentability received for PCT Patent Application No. PCT/IB2021/055127, mailed on Dec. 22, 2022, 12 pages.
International Search Report and Written Opinion received for PCT Patent Application No. PCT/IB2021/055127, mailed on Nov. 16, 2021, 17 pages.
"Naming the coronavirus disease (COVID-19) and the virus that causes it", World Health Organization, Available at <https://www.who.int/emergencies/diseases/novel-coronavirus-2019/technical-guidance/naming-the-coronavirus-disease-(covid-2019)-and-the-virus-that-causes-it>, 2020, 4 pages.
"Real-Time RT-PCR Panel for Detection 2019-Novel Coronavirus", Centers for Disease Control and Prevention, R. V. B., Division of Viral Diseases, 2020, 12 pages.
"The Species Severe Acute Respiratory Syndrome-Related Coronavirus: Classifying 2019-nCOV and Naming it SARS-CoV-2", Coronaviridae Study Group of the International Committee on Taxonomy of Viruses, Nat Microbiol, vol. 5, No. 4, Apr. 2020, pp. 536-544.
Attwood , et al., "Clinical Evaluation of AusDiagnostics SARS-CoV-2 Multiplex Tandem PCR Assay", Journal of Clinical Virology, Elsevier, Amsterdam, NL, vol. 128, May 19, 2020, 4 pages.

(Continued)

*Primary Examiner* — Agnieszka Boesen
(74) *Attorney, Agent, or Firm* — PABST PATENT GROUP LLP

(57) ABSTRACT

Methods for the rapid and accurate detection and characterization of a viral nucleic acid in a sample are provided. The method is a method for multiplex isothermal amplification-based sequencing and real-time analysis of multiple viral genomes. It can simultaneously detect SARS-CoV-2 and co-infecting respiratory viruses, and monitor mutations for up to 96 samples in real time. The method, termed NIRVANA for Nanopore sequencing of Isothermal Rapid Viral Amplification for Near real-time Analysis, showed high sensitivity and specificity for SARS-CoV-2 in 70 clinical samples. It also simultaneously detected other viral pathogens (e.g. influenza A) in clinical and municipal wastewater samples. It provides a rapid field-deployable solution of COVID-19 and co-infection detection and surveillance of the evolution of pandemic strains.

20 Claims, 13 Drawing Sheets

Specification includes a Sequence Listing.

(56) References Cited

OTHER PUBLICATIONS

Babiker , et al., "Metagenomic Sequencing To Detect Respiratory Viruses in Persons under Investigation for COVID-19", J Clin Microbiol, vol. 59, No. 1, e02142-20, 2020, 6 pages.
Bi , et al., "Long-read Individual-molecule Sequencing Reveals CRISPR-induced Genetic Heterogeneity in Human ESCs", bioRxiv, vol. 21, No. 1, 213, 2020, 14 pages.
Bi , et al., "Simultaneous Detection and Mutation Surveillance of SARS-CoV-2 and Multiple Respiratory Viruses by Rapid Field-Deployable Sequencing", MED, vol. 2, No. 6, Mar. 31, 2021, pp. 689-700.e4.
Broughton , et al., "CRISPR-Cas12-based detection of SARS-CoV-2", Nat Biotechnol, vol. 38, No. 7, 2020, pp. 870-874.
Carter , et al., "Assay Techniques and Test Development for COVID-19 Diagnosis", ACS Central Science, vol. 6, No. 5, Available at <https://www.ncbi.nlm.nih.gov/pmc/articles/PMC7197457/pdf/oc0c00501.pdf>, May 27, 2020, pp. 591-605.
Chomczynski , et al., "Single-step Method of RNA Isolation by Acid Guanidinium Thiocyanate-Phenol-Chloroform Extraction", Anal. Biochem, vol. 162, No. 1, 1987, pp. 156-159.
Corman , et al., "Detection of 2019 Novel Coronavirus (2019-nCOV) by Real-Time RT-PCR", Euro Surveill, vol. 25, No. 3: 2000045, 2020, 8 pages.
Gardy , et al., "Towards a Genomics-Informed, Real-Time, Global Pathogen Surveillance System", Nature reviews, vol. 19, No. 1, 2018, pp. 9-20.
Greninger , et al., "Rapid Metagenomic Identification of Viral Pathogens in Clinical Samples by Real-Time Nanopore Sequencing Analysis", Genome Med, vol. 7: 99, 2015, 13 pages.
Haramoto , et al., "Detection of Noroviruses in Tap Water in Japan by Means of a New Method for Concentrating Enteric Viruses in Large Volumes of Freshwater", Appl Environ Microbiol., vol. 70, No. 4, Apr. 2004, pp. 2154-2160.
Hashemi , et al., "High Prevalence of SARS-CoV-2 and Influenza A virus (H1N1) Coinfection in Dead Patients in Northeastern Iran", Journal of Medical Virology, vol. 93, No. 2, 2020, pp. 1008-1012.
James , et al., "LamPORE: Rapid, Accurate and Highly Scalable Molecular Screening for SARS-CoV-2 Infection, based on Nanopore Sequencin", medRxiv, 2020, 17 pages.
Joung , et al., "Point-of-care Testing for COVID-19 using SHERLOCK Diagnostics", medRxiv, 2020, 14 pages.
Katz , et al., "False-Positive Reverse Transcriptase Polymerase Chain Reaction Screening for SARS-CoV-2 in the Setting of Urgent Head and Neck Surgery and Otolaryngologic Emergencies during the Pandemic: Clinical Implications", Head Neck-J Sci Spec, vol. 42, No. 7, 2020, pp. 1621-1628.
Kim , et al., "Rates of Co-infection Between SARS-CoV-2 and Other Respiratory Pathogens", Jama-J Am Med Assoc, vol. 323, No. 20, May 26, 2020, pp. 2085-2086.
Kitajima , et al., "Pepper Mild Mottle Virus as a Water Quality Indicator", Npj Clean Water, vol. 1: 19, 2018, 9 pages.
Lansbury , et al., "Co-infections in People with COVID-19: A Systematic Review and Meta-Analysis", J Infection, vol. 81, No. 2, Aug. 2020, pp. 266-275.
Li , et al., "DeepSimulator1.5: A more Powerful, Quicker and Lighter Simulator for Nanopore Sequencing", Bioinformatics, vol. 36, No. 8, Apr. 15, 2020, pp. 2578-2580.
Li, Heng , "Minimap2: Pairwise Alignment for Nucleotide Sequences", Bioinformatics, vol. 34, No. 18, Sep. 15, 2018, pp. 3094-3100.
Li , et al., "The Sequence Alignment/Map format and SAMtools", Bioinformatics vol. 25, No. 16, Aug. 15, 2009, pp. 2078-2079.
Ma, et al., "Coinfection of SARS-CoV-2 and Other Respiratory Pathogens", Infect Drug Resist, vol. 13, Aug. 26, 2020, pp. 3045-3053.
Medema , et al., "Presence of SARS-Coronavirus-2 RNA in Sewage and Correlation with Reported COVID-19 Prevalence in the Early Stage of the Epidemic in The Netherlands", Environmental Science & Technology Letters, vol. 7, No. 7, May 20, 2020, pp. 511-516.
Notomi , et al., "Loop-Mediated Isothermal Amplification of DNA", Nucleic acids research, vol. 28, No. 12: E63, Jun. 15, 2000, 7 pages.
Nyan , et al., "A novel Multiplex Isothermal Amplification Method for Rapid Detection and Identification of Viruses", Scientific Reports, vol. 5, No. 1, Dec. 8, 2015, 9 pages.
Pachetti , et al., "Emerging SARS-CoV-2 Mutation Hot Spots include a Novel RNA-dependent-RNA Polymerase Variant", J Transl Med, vol. 18, No. 1: 179, Apr. 22, 2020, 9 pages.
Quick , et al., "Multiplex PCR method for MinION and Illumina Sequencing of Zika and other Virus Genomes directly from Clinical Samples", Nature Protocols, vol. 12, No. 6, May 24, 2017, pp. 1261-1276.
Richards , et al., "Elements of Family-Centered Care in the Pediatric Intensive Care Unit: An Integrative Review", J Hosp Palliat Nurs, vol. 19, No. 3, Jun. 2017, pp. 238-246.
Soliman , et al., "Rapid Detection and Differentiation of Carp Oedema Virus and Cyprinid Herpes Virus-3 in Koi and Common Carp", Journal of Fish Diseases, vol. 41, No. 5, May 2018, pp. 761-772.
Surkova, et al., "False-Positive COVID-19 Results: Hidden Problems and Costs", Lancet Respir Med, vol. 8, No. 12, Dec. 2020, pp. 1167-1168.
Vogels , et al., "Analytical Sensitivity and Efficiency Comparisons of SARS-CoV-2 RT-qPCR Primer-Probe Sets", Nat Microbiol, vol. 5, No. 10, Oct. 2020, pp. 1299-1305.
Voloshin , et al., "Homologous DNA Pairing Promoted by a 20-amino Acid Peptide Derived from RecA", Science vol. 272, No. 5263, May 10, 1996, pp. 868-872.
Wu , et al., "A New Coronavirus Associated with Human Respiratory Disease in China", Nature, vol. 579, No. 7798, Mar. 2020, pp. 265-269.
Yan , et al., "Rapid and Visual Detection of 2019 Novel Coronavirus (SARS-CoV-2) by a Reverse Transcription Loop-Mediated Isothermal Amplification Assay", Clin Microbiol Infect, vol. 26, No. 6, Jun. 2020, pp. 773-779.
Yin, Changchuan , "Genotyping Coronavirus SARS-CoV-2: Methods and Implications", Genomics, vol. 112, No. 5, Sep. 2020, pp. 3588-3596.
Zhang, et al., "A Genomic Perspective on the Origin and Emergence of SARS-CoV-2", Cell, vol. 181, No. 2, Apr. 16, 2020, pp. 223-227.
Zhang , et al., "Rapid Molecular Detection of SARS-CoV-2 (COVID-19) Virus RNA Using Colorimetric LAMP", medRxiv, 2020.02.26.20028373, 2020, 14 pages.

* cited by examiner

| | | | |
|---|---|---|---|
| sample01 | | | 28144 T/C |
| sample02 | | | 28144 T/C |
| sample03 | | | 28144 T/C |
| sample04 | 14408 C/T | | |
| sample05 | 14408 C/T | 23403 A/G | 28144 T/C |
| sample06 | 14408 C/T | 23403 A/G | |
| sample07 | 14408 C/T | 23403 A/G | |
| sample08 | 14408 C/T | 23403 A/G | |
| sample09 | | 23403 A/G | |
| sample10 | 14408 C/T | 23403 A/G | |

| Read number per amplicon | | | | | |
|---|---|---|---|---|---|
| position / sample | Pair 13 | Pair 5 | Pair 9 | Pair 4 | Pair 10 |
| sample01 | 34401 | 24845 | 2287 | 66325 | 41788 |
| sample02 | 20938 | 1043 | 29 | 20735 | 11830 |
| sample03 | 32322 | 9850 | 332 | 51450 | 22589 |
| sample04 | 37847 | 6151 | 3379 | 81953 | 3586 |
| sample05 | 27862 | 1503 | 668 | 6248 | 438 |
| sample06 | 59838 | 10427 | 1920 | 17849 | 3892 |
| sample07 | 63907 | 21127 | 22480 | 38411 | 26992 |
| sample08 | 32394 | 14867 | 8632 | 23044 | 8291 |
| sample09 | 34126 | 1569 | 651 | 10685 | 481 |
| sample10 | 27783 | 17773 | 13889 | 27825 | 18077 |

Read number per amplicon

| sample \ position | Pair 13 | Pair 5 | Pair 9 | Pair 4 | Pair 10 | ACTB |
|---|---|---|---|---|---|---|
| sample01_1 | 8055 | 404 | 21 | 12235 | 13 | 8357 |
| sample01_2 | 5430 | 155 | 15 | 4918 | 37 | 5 |
| sample02 | 1222 | 35 | 6 | 1052 | 4 | 10569 |

SEQUENCE LISTING

<160> NUMBER OF SEQ ID NOS: 21

<210> SEQ ID NO 1
<211> LENGTH: 29903
<212> TYPE: DNA
<213> ORGANISM: Severe acute respiratory syndrome coronavirus 2

<400> SEQUENCE: 1

```
attaaaggtt tataccttcc caggtaacaa accaaccaac tttcgatctc ttgtagatct     60
gttctctaaa cgaactttaa aatctgtgtg gctgtcactc ggctgcatgc ttagtgcact    120
cacgcagtat aattaataac taattactgt cgttgacagg acacgagtaa ctcgtctatc    180
ttctgcaggc tgcttacggt ttcgtccgtg ttgcagccga tcatcagcac atctaggttt    240
cgtccgggtg tgaccgaaag gtaagatgga gagccttgtc cctggtttca acgagaaaac    300
acacgtccaa ctcagtttgc ctgttttaca ggttcgcgac gtgctcgtac gtggctttgg    360
agactccgtg gaggaggtct tatcagaggc acgtcaacat cttaaagatg gcacttgtgg    420
cttagtagaa gttgaaaaag gcgttttgcc tcaacttgaa cagccctatg tgttcatcaa    480
acgttcggat gctcgaactg cacctcatgg tcatgttatg gttgagctgg tagcagaact    540
cgaaggcatt cagtacggtc gtagtggtga gacacttggt gtccttgtcc ctcatgtggg    600
cgaaatacca gtggcttacc gcaaggttct tcttcgtaag aacggtaata aaggagctgg    660
tggccatagt tacggcgccg atctaaagtc atttgactta ggcgacgagc ttggcactga    720
tccttatgaa gattttcaag aaaactggaa cactaaacat agcagtggtg ttacccgtga    780
actcatgcgt gagcttaacg gaggggcata cactcgctat gtcgataaca acttctgtgg    840
ccctgatggc taccctcttg agtgcattaa agaccttcta gcacgtgctg gtaaagcttc    900
atgcactttg tccgaacaac tggactttat tgacactaag aggggtgtat actgctgccg    960
tgaacatgag catgaaattg cttggtacac ggaacgttct gaaaagagct atgaattgca   1020
gacacctttt gaaattaaat tggcaaagaa atttgacacc ttcaatgggg aatgtccaaa   1080
ttttgtattt cccttaaatt ccataatcaa gactattcaa ccaagggttg aaaagaaaaa   1140
gcttgatggc tttatgggta gaattcgatc tgtctatcca gttgcgtcac caaatgaatg   1200
caaccaaatg tgcctttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaaattt attgtccagc   1380
atgtcacaat tcagaagtag gacctgagca tagtcttgcc gaataccata atgaatctgg   1440
cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
```

```
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
tatttttggt gctgacccta tacattcttt aagagtttgt gtagatactg ttcgcacaaa   3780
tgtctactta gctgtctttg ataaaaatct ctatgacaaa cttgtttcaa gctttttgga   3840
aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
```

```
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca aagaaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
```

```
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt tttgatggt aaatcaaaat gtgaagaatc    7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
```

-continued

```
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
```

tggtaataca cttcagtgta taatgctagt ttattgtttc ttaggctatt tttgtacttg 11640
ttactttggc ctcttttgtt tactcaaccg ctactttaga ctgactcttg gtgtttatga 11700
ttacttagtt tctacacagg agtttagata tatgaattca cagggactac tcccacccaa 11760
gaatagcata gatgccttca aactcaacat taaattgttg ggtgttggtg gcaaaccttg 11820
tatcaaagta gccactgtac agtctaaaat gtcagatgta aagtgcacat cagtagtctt 11880
actctcagtt ttgcaacaac tcagagtaga atcatcatct aaattgtggg ctcaatgtgt 11940
ccagttacac aatgacattc tcttagctaa agatactact gaagcctttg aaaaaatggt 12000
ttcactactt tctgttttgc tttccatgca gggtgctgta gacataaaca agctttgtga 12060
agaaatgctg gacaacaggg caaccttaca agctatagcc tcagagttta gttcccttcc 12120
atcatatgca gcttttgcta ctgctcaaga agcttatgag caggctgttg ctaatggtga 12180
ttctgaagtt gttcttaaaa agttgaagaa gtctttgaat gtggctaaat ctgaatttga 12240
ccgtgatgca gccatgcaac gtaagttgga aaagatggct gatcaagcta tgacccaaat 12300
gtataaacag gctagatctg aggacaagag ggcaaaagtt actagtgcta tgcagacaat 12360
gcttttcact atgcttagaa agttggataa tgatgcactc aacaacatta tcaacaatgc 12420
aagagatggt tgtgttccct tgaacataat acctcttaca acagcagcca aactaatggt 12480
tgtcatacca gactataaca catataaaaa tacgtgtgat ggtacaacat ttacttatgc 12540
atcagcattg tgggaaatcc aacaggttgt agatgcagat agtaaaattg ttcaacttag 12600
tgaaattagt atggacaatt cacctaattt agcatggcct cttattgtaa cagctttaag 12660
ggccaattct gctgtcaaat tacagaataa tgagcttagt cctgttgcac tacgacagat 12720
gtcttgtgct gccggtacta cacaaactgc ttgcactgat gacaatgcgt tagcttacta 12780
caacacaaca aagggaggta ggtttgtact tgcactgtta tccgatttac aggatttgaa 12840
atgggctaga ttccctaaga gtgatggaac tggtactatc tatacagaac tggaaccacc 12900
ttgtaggttt gttacagaca cacctaaagg tcctaaagtg aagtatttat actttattaa 12960
aggattaaac aacctaaata gaggtatggt acttggtagt ttagctgcca cagtacgtct 13020
acaagctggt aatgcaacag aagtgcctgc caattcaact gtattatctt tctgtgcttt 13080
tgctgtagat gctgctaaag cttacaaaga ttatctagct agtgggggac aaccaatcac 13140
taattgtgtt aagatgttgt gtacacacac tggtactggt caggcaataa cagttacacc 13200
ggaagccaat atggatcaag aatcctttgg tggtgcatcg tgttgtctgt actgccgttg 13260
ccacatagat catccaaatc ctaaaggatt ttgtgactta aaaggtaagt atgtacaaat 13320
acctacaact tgtgctaatg accctgtggg ttttacactt aaaaacacag tctgtaccgt 13380
ctgcggtatg tggaaaggtt atggctgtag ttgtgatcaa ctccgcgaac ccatgcttca 13440
gtcagctgat gcacaatcgt ttttaaacgg gtttgcggtg taagtgcagc ccgtcttaca 13500
ccgtgcggca caggcactag tactgatgtc gtatacaggg cttttgacat ctacaatgat 13560
aaagtagctg gttttgctaa attcctaaaa actaattgtt gtcgcttcca agaaaaggac 13620
gaagatgaca atttaattga ttcttacttt gtagttaaga gacacacttt ctctaactac 13680
caacatgaag aaacaattta taatttactt aaggattgtc cagctgttgc taaacatgac 13740
ttctttaagt ttagaataga cggtgacatg gtaccacata tatcacgtca acgtcttact 13800
aaatacacaa tggcagacct cgtctatgct ttaaggcatt ttgatgaagg taattgtgac 13860
acattaaaag aaatacttgt cacatacaat tgttgtgatg atgattattt caataaaaag 13920

-continued

```
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
```

```
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
```

```
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
```

aagactaaaa atgttacaaa agaaaatgac tctaaagagg gttttttcac ttacatttgt 21120
gggtttatac aacaaaagct agctcttgga ggttccgtgg ctataaagat aacagaacat 21180
tcttggaatg ctgatcttta taagctcatg ggacacttcg catggtggac agcctttgtt 21240
actaatgtga atgcgtcatc atctgaagca tttttaattg gatgtaatta tcttggcaaa 21300
ccacgcgaac aaatagatgg ttatgtcatg catgcaaatt acatattttg gaggaataca 21360
aatccaattc agttgtcttc ctattcttta tttgacatga gtaaatttcc ccttaaatta 21420
aggggtactg ctgttatgtc tttaaaagaa ggtcaaatca atgatatgat tttatctctt 21480
cttagtaaag gtagacttat aattagagaa aacaacagag ttgttatttc tagtgatgtt 21540
cttgttaaca actaaacgaa caatgtttgt ttttcttgtt ttattgccac tagtctctag 21600
tcagtgtgtt aatcttacaa ccagaactca attacccct gcatacacta attctttcac 21660
acgtggtgtt tattaccctg acaaagtttt cagatcctca gttttacatt caactcagga 21720
cttgttctta cctttctttt ccaatgttac ttggttccat gctatacatg tctctgggac 21780
caatggtact aagaggtttg ataaccctgt cctaccattt aatgatggtg tttattttgc 21840
ttccactgag aagtctaaca taataagagg ctggattttt ggtactactt tagattcgaa 21900
gacccagtcc ctacttattg ttaataacgc tactaatgtt gttattaaag tctgtgaatt 21960
tcaattttgt aatgatccat ttttgggtgt ttattaccac aaaaacaaca aaagttggat 22020
ggaaagtgag ttcagagttt attctagtgc gaataattgc acttttgaat atgtctctca 22080
gccttttctt atggaccttg aaggaaaaca gggtaatttc aaaaatctta gggaatttgt 22140
gtttaagaat attgatggtt attttaaaat atattctaag cacacgccta ttaatttagt 22200
gcgtgatctc cctcagggtt tttcggcttt agaaccattg gtagatttgc caataggtat 22260
taacatcact aggtttcaaa ctttacttgc tttacataga agttatttga ctcctggtga 22320
ttcttcttca ggttggacag ctggtgctgc agcttattat gtgggttatc ttcaacctag 22380
gacttttcta ttaaaatata atgaaaatgg aaccattaca gatgctgtag actgtgcact 22440
tgaccctctc tcagaaacaa agtgtacgtt gaaatccttc actgtagaaa aaggaatcta 22500
tcaaacttct aactttagag tccaaccaac agaatctatt gttagatttc ctaatattac 22560
aaacttgtgc ccttttggtg aagtttttaa cgccaccaga tttgcatctg tttatgcttg 22620
gaacaggaag agaatcagca actgtgttgc tgattattct gtcctatata attccgcatc 22680
attttccact tttaagtgtt atggagtgtc tcctactaaa ttaaatgatc tctgctttac 22740
taatgtctat gcagattcat ttgtaattag aggtgatgaa gtcagacaaa tcgctccagg 22800
gcaaactgga aagattgctg attataatta taaattacca gatgatttta caggctgcgt 22860
tatagcttgg aattctaaca atcttgattc taaggttggt ggtaattata attacctgta 22920
tagattgttt aggaagtcta atctcaaacc ttttgagaga gatatttcaa ctgaaatcta 22980
tcaggccggt agcacacctt gtaatggtgt tgaaggtttt aattgttact ttcctttaca 23040
atcatatggt ttccaaccca ctaatggtgt tggttaccaa ccatacagag tagtagtact 23100
ttcttttgaa cttctacatg caccagcaac tgtttgtgga cctaaaaagt ctactaattt 23160
ggttaaaaac aaatgtgtca atttcaactt caatggttta acaggcacag gtgttcttac 23220
tgagtctaac aaaaagtttc tgcctttcca acaatttggc agagacattg ctgacactac 23280
tgatgctgtc cgtgatccac agacacttga gattcttgac attacaccat gttcttttgg 23340
tggtgtcagt gttataacac caggaacaaa tacttctaac caggttgctg ttctttatca 23400

```
ggatgttaac tgcacagaag tccctgttgc tattcatgca gatcaactta ctcctacttg  23460
gcgtgtttat tctacaggtt ctaatgtttt tcaaacacgt gcaggctgtt taatagggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
```

aacccattac tttatgatgc caactatttt ctttgctggc atactaattg ttacgactat 25860
tgtatacctt acaatagtgt aacttcttca attgtcatta cttcaggtga tggcacaaca 25920
agtcctattt ctgaacatga ctaccagatt ggtggttata ctgaaaaatg ggaatctgga 25980
gtaaaagact gtgttgtatt acacagttac ttcacttcag actattacca gctgtactca 26040
actcaattga gtacagacac tggtgttgaa catgttacct tcttcatcta caataaaatt 26100
gttgatgagc ctgaagaaca tgtccaaatt cacacaatcg acggttcatc cggagttgtt 26160
aatccagtaa tggaaccaat ttatgatgaa ccgacgacga ctactagcgt gcctttgtaa 26220
gcacaagctg atgagtacga acttatgtac tcattcgttt cggaagagac aggtacgtta 26280
atagttaata gcgtacttct ttttcttgct ttcgtggtat tcttgctagt tacactagcc 26340
atccttactg cgcttcgatt gtgtgcgtac tgctgcaata ttgttaacgt gagtcttgta 26400
aaaccttctt tttacgttta ctctcgtgtt aaaaatctga attcttctag agttcctgat 26460
cttctggtct aaacgaacta aatattatat tagtttttct gtttggaact ttaattttag 26520
ccatggcaga ttccaacggt actattaccg ttgaagagct taaaaagctc cttgaacaat 26580
ggaacctagt aataggtttc ctattcctta catggatttg tcttctacaa tttgcctatg 26640
ccaacaggaa taggtttttg tatataatta agttaatttt cctctggctg ttatggccag 26700
taactttagc ttgttttgtg cttgctgctg tttacagaat aaattggatc accggtggaa 26760
ttgctatcgc aatggcttgt cttgtaggct tgatgtggct cagctacttc attgcttctt 26820
tcagactgtt tgcgcgtacg cgttccatgt ggtcattcaa tccagaaact aacattcttc 26880
tcaacgtgcc actccatggc actattctga ccagaccgct tctagaaagt gaactcgtaa 26940
tcggagctgt gatccttcgt ggacatcttc gtattgctgg acaccatcta ggacgctgtg 27000
acatcaagga cctgcctaaa gaaatcactg ttgctacatc acgaacgctt tcttattaca 27060
aattgggagc ttcgcagcgt gtagcaggtg actcaggttt tgctgcatac agtcgctaca 27120
ggattggcaa ctataaatta aacacagacc attccagtag cagtgacaat attgctttgc 27180
ttgtacagta agtgacaaca gatgtttcat ctcgttgact ttcaggttac tatagcagag 27240
atattactaa ttattatgag gacttttaaa gtttccattt ggaatcttga ttacatcata 27300
aacctcataa ttaaaaattt atctaagtca ctaactgaga ataaatattc tcaattagat 27360
gaagagcaac caatggagat tgattaaacg aacatgaaaa ttattctttt cttggcactg 27420
ataacactcg ctacttgtga gctttatcac taccaagagt gtgttagagg tacaacagta 27480
cttttaaaag aaccttgctc ttctggaaca tacgagggca attcaccatt tcatcctcta 27540
gctgataaca aatttgcact gacttgcttt agcactcaat ttgcttttgc ttgtcctgac 27600
ggcgtaaaac acgtctatca gttacgtgcc agatcagttt cacctaaact gttcatcaga 27660
caagaggaag ttcaagaact ttactctcca atttttctta ttgttgcggc aatagtgttt 27720
ataacacttt gcttcacact caaaagaaag acagaatgat tgaactttca ttaattgact 27780
tctatttgtg ctttttagcc tttctgctat tccttgtttt aattatgctt attatctttt 27840
ggttctcact tgaactgcaa gatcataatg aaacttgtca cgcctaaacg aacatgaaat 27900
ttcttgtttt cttaggaatc atcacaactg tagctgcatt tcaccaagaa tgtagtttac 27960
agtcatgtac tcaacatcaa ccatatgtag ttgatgaccc gtgtcctatt cacttctatt 28020
ctaaatggta tattagagta ggagctagaa aatcagcacc tttaattgaa ttgtgcgtgg 28080
atgaggctgg ttctaaatca cccattcagt acatcgatat cggtaattat acagtttcct 28140

-continued

```
gtttaccttt tacaattaat tgccaggaac ctaaattggg tagtcttgta gtgcgttgtt  28200

cgttctatga agacttttta gagtatcatg acgttcgtgt tgttttagat ttcatctaaa  28260

cgaacaaact aaaatgtctg ataatggacc ccaaaatcag cgaaatgcac cccgcattac  28320

gtttggtgga ccctcagatt caactggcag taaccagaat ggagaacgca gtggggcgcg  28380

atcaaaacaa cgtcggcccc aaggtttacc caataatact gcgtcttggt tcaccgctct  28440

cactcaacat ggcaaggaag accttaaatt ccctcgagga caaggcgttc caattaacac  28500

caatagcagt ccagatgacc aaattggcta ctaccgaaga gctaccagac gaattcgtgg  28560

tggtgacggt aaaatgaaag atctcagtcc aagatggtat ttctactacc taggaactgg  28620

gccagaagct ggacttccct atggtgctaa caaagacggc atcatatggg ttgcaactga  28680

gggagccttg aatacaccaa aagatcacat tggcacccgc aatcctgcta acaatgctgc  28740

aatcgtgcta caacttcctc aaggaacaac attgccaaaa ggcttctacg cagaagggag  28800

cagaggcggc agtcaagcct cttctcgttc ctcatcacgt agtcgcaaca gttcaagaaa  28860

ttcaactcca ggcagcagta ggggaacttc tcctgctaga atggctggca atggcggtga  28920

tgctgctctt gctttgctgc tgcttgacag attgaaccag cttgagagca aaatgtctgg  28980

taaaggccaa caacaacaag gccaaactgt cactaagaaa tctgctgctg aggcttctaa  29040

gaagcctcgg caaaaacgta ctgccactaa agcatacaat gtaacacaag ctttcggcag  29100

acgtggtcca gaacaaaccc aaggaaattt tggggaccag gaactaatca gacaaggaac  29160

tgattacaaa cattggccgc aaattgcaca atttgccccc agcgcttcag cgttcttcgg  29220

aatgtcgcgc attggcatgg aagtcacacc ttcgggaacg tggttgacct acacaggtgc  29280

catcaaattg gatgacaaag atccaaattt caaagatcaa gtcattttgc tgaataagca  29340

tattgacgca tacaaaacat tcccaccaac agagcctaaa aaggacaaaa agaagaaggc  29400

tgatgaaact caagccttac cgcagagaca gaagaaacag caaactgtga ctcttcttcc  29460

tgctgcagat ttggatgatt tctccaaaca attgcaacaa tccatgagca gtgctgactc  29520

aactcaggcc taaactcatg cagaccacac aaggcagatg ggctatataa acgttttcgc  29580

ttttccgttt acgatatata gtctactctt gtgcagaatg aattctcgta actacatagc  29640

acaagtagat gtagttaact ttaatctcac atagcaatct ttaatcagtg tgtaacatta  29700

gggaggactt gaaagagcca ccacattttc accgaggcca cgcggagtac gatcgagtgt  29760

acagtgaaca atgctaggga gagctgccta tatggaagag ccctaatgtg taaaattaat  29820

tttagtagtg ctatccccat gtgattttaa tagcttctta ggagaatgac aaaaaaaaaa  29880

aaaaaaaaaa aaaaaaaaaa aaa                                          29903
```

<210> SEQ ID NO 2
<211> LENGTH: 25
<212> TYPE: DNA
<213> ORGANISM: Artificial Sequence
<220> FEATURE:
<223> OTHER INFORMATION: pair4-F Primer

<400> SEQUENCE: 2

```
gctggttcta aatcacccat tcagt                                          25
```

<210> SEQ ID NO 3
<211> LENGTH: 24
<212> TYPE: DNA
<213> ORGANISM: Artificial Sequence
<220> FEATURE:
<223> OTHER INFORMATION: pair4-R Primer

<400> SEQUENCE: 3
tctggttact gccagttgaa tctg 24

<210> SEQ ID NO 4
<211> LENGTH: 22
<212> TYPE: DNA
<213> ORGANISM: Artificial Sequence
<220> FEATURE:
<223> OTHER INFORMATION: pair 5-F Primer

<400> SEQUENCE: 4
ttgggatcag acataccacc ca 22

<210> SEQ ID NO 5
<211> LENGTH: 23
<212> TYPE: DNA
<213> ORGANISM: Artificial Sequence
<220> FEATURE:
<223> OTHER INFORMATION: pair5-R Primer

<400> SEQUENCE: 5
caacacctag ctctctgaag tgg 23

<210> SEQ ID NO 6
<211> LENGTH: 21
<212> TYPE: DNA
<213> ORGANISM: Artificial Sequence
<220> FEATURE:
<223> OTHER INFORMATION: pair9-F Primer

<400> SEQUENCE: 6
ccagcaactg tttgtggacc t 21

<210> SEQ ID NO 7
<211> LENGTH: 20
<212> TYPE: DNA
<213> ORGANISM: Artificial Sequence
<220> FEATURE:
<223> OTHER INFORMATION: pair9-R Primer

<400> SEQUENCE: 7
agcaacaggg acttctgtgc 20

<210> SEQ ID NO 8
<211> LENGTH: 20
<212> TYPE: DNA
<213> ORGANISM: Artificial Sequence
<220> FEATURE:
<223> OTHER INFORMATION: pair10-F Primer

<400> SEQUENCE: 8
gaccccaaaa tcagcgaaat 20

<210> SEQ ID NO 9
<211> LENGTH: 21
<212> TYPE: DNA
<213> ORGANISM: Artificial Sequence
<220> FEATURE:
<223> OTHER INFORMATION: pair10-R Primer

<400> SEQUENCE: 9
tgtagcacga ttgcagcatt g 21

<210> SEQ ID NO 10

<211> LENGTH: 25
<212> TYPE: DNA
<213> ORGANISM: Artificial Sequence
<220> FEATURE:
<223> OTHER INFORMATION: pair13-F Primer

<400> SEQUENCE: 10
ccagagtact caatggtctt tgttc 25

<210> SEQ ID NO 11
<211> LENGTH: 23
<212> TYPE: DNA
<213> ORGANISM: Artificial Sequence
<220> FEATURE:
<223> OTHER INFORMATION: pair13-R Primer

<400> SEQUENCE: 11
acccaactag caggcatata gac 23

<210> SEQ ID NO 12
<211> LENGTH: 27
<212> TYPE: DNA
<213> ORGANISM: Artificial Sequence
<220> FEATURE:
<223> OTHER INFORMATION: ACTB-F Primer

<400> SEQUENCE: 12
cccagccatg tacgttgcta tccaggc 27

<210> SEQ ID NO 13
<211> LENGTH: 28
<212> TYPE: DNA
<213> ORGANISM: Artificial Sequence
<220> FEATURE:
<223> OTHER INFORMATION: ACTB-R Primer

<400> SEQUENCE: 13
acagcttctc cttaatgtca cgcacgat 28

<210> SEQ ID NO 14
<211> LENGTH: 27
<212> TYPE: DNA
<213> ORGANISM: Artificial Sequence
<220> FEATURE:
<223> OTHER INFORMATION: FluA-F Primer
<220> FEATURE:
<221> NAME/KEY: variation
<222> LOCATION: (3)..(3)
<223> OTHER INFORMATION: Y is C or T
<220> FEATURE:
<221> NAME/KEY: variation
<222> LOCATION: (6)..(6)
<223> OTHER INFORMATION: Y is C or T

<400> SEQUENCE: 14
atgagyctty taaccgaggt cgaaacg 27

<210> SEQ ID NO 15
<211> LENGTH: 23
<212> TYPE: DNA
<213> ORGANISM: Artificial Sequence
<220> FEATURE:
<223> OTHER INFORMATION: FluA-R Primer
<220> FEATURE:
<221> NAME/KEY: variation
<222> LOCATION: (9)..(9)
<223> OTHER INFORMATION: N is C or T or A or G
<220> FEATURE:
<221> NAME/KEY: misc_feature
<222> LOCATION: (9)..(9)
<223> OTHER INFORMATION: n is a, c, g, or t

<400> SEQUENCE: 15
tggacaaanc gtctacgctg cag 23

<210> SEQ ID NO 16
<211> LENGTH: 23
<212> TYPE: DNA
<213> ORGANISM: Artificial Sequence
<220> FEATURE:
<223> OTHER INFORMATION: HAdV-F Primer

<400> SEQUENCE: 16
gccgagaagg gcgtgcgcag gta 23

<210> SEQ ID NO 17
<211> LENGTH: 23
<212> TYPE: DNA
<213> ORGANISM: Artificial Sequence
<220> FEATURE:
<223> OTHER INFORMATION: HAdV-R Primer

<400> SEQUENCE: 17
tacgccaact ccgcccacgc gct 23

<210> SEQ ID NO 18
<211> LENGTH: 32
<212> TYPE: DNA
<213> ORGANISM: Artificial Sequence
<220> FEATURE:
<223> OTHER INFORMATION: HCoV-F Primer

<400> SEQUENCE: 18
atggtcaagg agttcccatt gctttcggag ta 32

<210> SEQ ID NO 19
<211> LENGTH: 34
<212> TYPE: DNA
<213> ORGANISM: Artificial Sequence
<220> FEATURE:
<223> OTHER INFORMATION: HCoV-R Primer

<400> SEQUENCE: 19
gggccggtac cgagatagta gaaataccat ctcg 34

<210> SEQ ID NO 20
<211> LENGTH: 31
<212> TYPE: DNA
<213> ORGANISM: Artificial Sequence
<220> FEATURE:
<223> OTHER INFORMATION: PMMoV-R Primer

<400> SEQUENCE: 20
aactcatcgg acactgtgtt gcctgttaga c 31

<210> SEQ ID NO 21
<211> LENGTH: 32
<212> TYPE: DNA
<213> ORGANISM: Artificial Sequence
<220> FEATURE:
<223> OTHER INFORMATION: PMMoV-F Primer

<400> SEQUENCE: 21
tcaaatgaga gtggtttgac cttaacgttt ga 32

RAPID MULTIPLEX RPA BASED NANOPORE SEQUENCING METHOD FOR REAL-TIME DETECTION AND SEQUENCING OF MULTIPLE VIRAL PATHOGENS

CROSS-REFERENCE TO RELATED APPLICATIONS

This application is a National Phase application under 35 U.S.C. 371 of PCT/IB2021/055127, filed Jun. 10, 2021, which claims the benefit of and priority to U.S. Provisional Application No. 63/163,227 filed Mar. 19, 2021 and U.S. Provisional Application No. 63/037,175 filed Jun. 10, 2020, which are hereby incorporated herein by reference in their entirety.

REFERENCE TO SEQUENCE LISTING

The Sequence Listing submitted as a .txt file named "KAUST_2020-153-05_371_ST25.txt," created on Jun. 21, 2023, and having a size of 43,461 bytes, is hereby incorporated by reference pursuant to 37 C.F.R. § 1.52(e)(5) and 37 C.F.R. § 1.825(a)(2).

FIELD OF THE INVENTION

This invention is generally in the field of viral pathogen detection.

BACKGROUND OF THE INVENTION

The novel coronavirus disease (COVID-19) pandemic is one of the most serious challenges to public health and global economy in modern history. SARS-CoV-2 is a positive-sense RNA betacoronavirus that causes COVID-19[1]. It was identified as the pathogenic cause of an outbreak of viral pneumonia of unknown etiology in Wuhan, China, by the Chinese Center for Disease Control and Prevention (CCDC) on Jan. 7, 2020[2]. Three days later, the first SARS-CoV-2 genome was released online through a collaborative effort by scientists in universities in China and Australia and Chinese public health agencies (GenBank: MN908947.3)[3]. One week after the publication of the genome the first diagnostic detection of SARS-CoV-2 using real-time reverse transcription polymerase chain reaction (rRT-PCR) was released by a group in Germany[4].

To date, rRT-PCR assays of various designs, including one approved by the US Centers for Disease Control and Prevention (US CDC) under emergency use authorization (EUA)[5], have remained the predominant diagnostic method for SARS-CoV-2. Although proven sensitive and specific for providing a positive or negative answer, rRT-PCR provides little information on the genomic sequence of the virus, knowledge of which is crucial for monitoring how SARS-CoV-2 is evolving and spreading and ensuring successful development of new diagnostic tests and vaccines. To this end, samples need to go through a separate workflow-typically Illumina shotgun metagenomics or targeted next-generation sequencing (NGS)[6]. Because NGS requires complicated molecular biology procedures and high-value instruments in centralized laboratories, it is performed in <1% as many cases as rRT-PCR, evidenced by the number of genomes in the GISAID (Global initiative on sharing all influenza data) database (39,954) and confirmed global cases tallied by the WHO (6,535,354) as of Jun. 5, 2020.

SARS-CoV-2 infections often cause symptoms similar to other respiratory viruses, thus making it challenging to distinguish co-infection especially in the flu season. Several studies have reported co-infection of SARS-CoV-2 and other respiratory viruses-respiratory syncytial virus (RSV) and influenza being the most common viral pathogens identified[7,8], and influenza was particularly high in dead patients[9]. The detection of co-infection is potentially useful for monitoring the SARS-CoV-2 pandemic and benefiting the treatment of patients. To date, no method can rapidly diagnose multiple viral infections in a high-throughput manner. Ideally, such methods should be field-deployable to allow timely assessment of outbreaks anywhere anytime.

Both rRT-PCR and NGS are sophisticated techniques whose implementation is contingent on the availability of highly-specialized facilities, personnel and reagents. These limitations could translate into long turn-over time and inadequate access to tests even in developed countries. To address these issues, several PCR-free nucleic acid detection assays have been proposed as point-of-care replacements of rRT-PCR. Chief among them is reverse transcription coupled loop-mediated isothermal amplification (RT-LAMP[10]), which has been used for rapid detection of SARS-CoV-2 RNA[11-14] On the sequencing front, the pocket-sized Oxford Nanopore MinION sequencer has been used for rapid pathogen identification in the field[15,16]. Because MinION offers base calling on the fly, it is an attractive platform for consolidating viral nucleic acid detection by PCR-free rapid isothermal amplification and viral mutation monitoring by sequencing. However, there are several challenges for an integrated point-of-care solution based on RT-LAMP and Nanopore sequencing. RT-LAMP requires a complex mixture of primers that increases the chance of non-specific amplification and makes it difficult to multiplex. Additionally, LAMP amplicons used for SARS-CoV-2 detection are short[12,13]. Sequencing singleplex short amplicons not only fails to take advantage of the long-read and sequencing throughput (~10 Gb) of the MinION flow cell, it is also prone to false negative reporting due to amplification failure. Little to no reports on multiplexed isothermal amplification of SARS-CoV-2 have been published to date. Nanopore sequencing has its own caveats too. Due to its relatively high basecalling error, new bioinformatics tools based on dedicated algorithms[17,18] are also needed to accurate call the presence of viral sequences (substituting for rRT-PCR) and analyze virus mutations (substituting for NGS).

It is an object of the present invention to provide methods for detecting the presence of multiple viral RNA in a sample as well as mutations in the viral RNA sequence.

SUMMARY OF THE INVENTION

An isothermal recombinase polymerase amplification (RPA) assay is disclosed, which can be used to simultaneously amplify up to nine regions of multiple viruses. Also disclosed is a method termed Nanopore sequencing of Isothermal Rapid Viral Amplification for Near real-time Analysis (NIRVANA), to detect the presence of viral sequences and monitor mutations in multiple viruses in up to 96 patients at a time. A bioinformatics pipeline for on-the-fly demultiplexing and variant analysis has been developed, to reduce the time to answer, and sequencing cost, by stopping the sequencing run when data is sufficient to provide confident answers. The whole workflow can be as short as 3.5 hours, and all reactions can be done in a simple heating block. NIRVANA provides a rapid field-deployable solution of COVID-19 and co-infection detection and surveillance of the evolution of pandemic strains.

In a particular embodiment, disclosed is a method for determining the presence of a viral nucleic acid in a sample. Typically, the method involves (i) contacting the sample with a plurality of primers specific to the nucleic acid; (ii) performing a single reaction to simultaneously amplify a plurality of target regions in the multiple viral nucleic acid, thereby generating a plurality of amplification products; and (iii) detecting the amplification products. The detection can be achieved through fluorescence detection, gel electrophoresis, and the like, for example. Preferably, detection of amplification products indicates the presence of the viral nucleic acid in the sample.

The method is suitable for the detection of any virus or nucleic acid therefrom. In some embodiments, the virus is a coronavirus, such as a severe acute respiratory syndrome-related coronavirus (e.g., SARS-CoV or SARS-CoV-2).

Typically, the method involves the use of plurality of primers, such as 7-9 pairs of primers. Thus, in some embodiments, a corresponding number of target regions is amplified. For example, the plurality of target regions can include up to 7-9 target regions. In preferred embodiments, 9 pairs of primers are used and/or 9 target regions are amplified. The target regions can include viral genomic regions that harbor signature mutations or mutation hotspots. Exemplary target regions include regions within the N gene, S gene, ORFlab, or ORF8 of a coronavirus (e.g., SARS-CoV-2), influenza A (FluA), human adenovirus (HAdV), and non-SARS-CoV-2 human coronavirus (HCoV). Primers suitable for use in the method include primers having a nucleic acid sequence that has at least 90% sequence identity to any one of SEQ ID NOs:2-11. A preferred amplification reaction for use in the method is an isothermal recombinase polymerase amplification (RPA), although normal PCR is also usable. The method can further include characterizing the viral nucleic acid. For example, such characterization can involve sequencing the amplification products and analyzing the resulting sequences. Any suitable sequencing platform can be used. In preferred embodiments, the sequencing is performed using a Nanopore MinION. Typically, analysis of the sequences includes aligning the sequences to a reference viral genome. In some embodiments, the existence of targeted amplicons is indicative of the presence of the viral nucleic acid in the sample. The existence of transcripts of the human housekeeping gene ACTB is a quality check of sample collection. To simplify the interpretation of the result, the data analysis algorithm (RTNano) provides a summary score of SARS-CoV-2 based on predefined rules. SARS-CoV-2 positive samples (POS) are assigned with different confidence levels based on the number of covered amplicons and corresponding positive records, range from 0 to 3 (lowest to highest). When there is no record of SARS-CoV-2, the sample could be categorized as either negative (NEG) if there are enough records of ACTB; or unknown (UKN) if there are insufficient records of ACTB.

The analysis can additionally include identifying one or more genetic variants (e.g., mutations) in the sequences as compared to the reference. Exemplary variants that can be identified include single nucleotide variants, multiple nucleotide variants, indels, deletions or insertions larger than 50 bp, inversions, or duplications. The analysis can be performed in real-time or near real-time. For example, in some embodiments, a folder containing the sequences being generated is continuously monitored output and the analysis if intermittently performed on any interim sequencing results.

The method affords multiplexing across a variety of samples. For example, the method can be performed on about 10-100 samples simultaneously. In some embodiments, the method has a duration of about 0.5-4 hours.

Also disclosed is a method for detecting the presence of a viral nucleic acid in a sample and one or more mutations therein. Typically, the method includes: (a) performing an isothermal recombinase polymerase amplification (RPA) on the sample to simultaneously amplify a plurality of target regions in multiple viral nucleic acids, thereby generating a plurality of amplification products; (b) sequencing the amplification products; (c) aligning the sequences to reference viral genomes/sequences, wherein the existence of targeted amplicons indicates presence of the viral nucleic acid; and (d) determining the presence of one or more mutations in the sequences as compared to the reference.

Also provided are methods for detecting or diagnosing viral infections in a subject. An exemplary method of diagnosing a subject for infection with a virus involves detecting the presence of a viral nucleic acid in a sample from the subject by any of the foregoing methods. In some embodiments, detection of the amplification products indicates the subjects is infected with the virus. In other embodiments, detection of sequence reads across all the targeted regions indicates the subjects is infected with the virus. The subject may or may not exhibit symptoms of a disease, disorder, or condition associated with the virus. In some embodiments, upon diagnosis as infected with the virus, the subject is treated. Preferably, the subject is human.

In any of the forgoing methods, the sample can be a nucleic acid sample. For example, the sample can contain DNA and/or RNA. The nucleic acid can be isolated, extracted or derived (e.g., cDNA generated from RNA by a reverse transcriptase) from any suitable source. Suitable non-limiting sources for providing the nucleic acid sample include mucus, sputum (processed or unprocessed), bronchial alveolar lavage (BAL), bronchial wash (BW), cerebrospinal fluid (CSF), urine, tissue (e.g., biopsy material), rectal swab, nasopharyngeal aspirate, nasopharyngeal swab, throat swab, saliva, feces, mucosal excretions, plasma, serum, or whole blood.

Additional advantages of the disclosed methods will be set forth in part in the description which follows, and in part will be understood from the description, or can be learned by practice of the disclosed methods and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A is a schematic representation of NIRVANA. RNA samples were subjected to reverse transcription, followed by multiplex RPA to amplify multiple regions of the SARS-CoV-2 genome. The amplicons were purified and prepared to the Nanopore library using an optimized barcoding library preparation protocol. In the end, the sequencing was performed in the pocket-sized Nanopore MinION sequencer and sequencing results were analyzed by our algorithm termed RTNano on the fly. FIG. 1B. shows the RPA primers used in this study plotted in the SARS-CoV-2 genome. The RPA amplicons are shown. The corresponding prevalent variants were labeled under the genome. FIG. 1C shows agarose gel electrophoresis results of multiplex RPA. All of the five amplicons were shown in the gel with correct size (asterisks, note that pair 5 and 13 have similar sizes). The no template control (NTC) showed a different pattern of non-specific amplicons. M: molecular size marker. FIG. 1D shows IGV plots showing Nanopore sequencing read coverage of the SARS-CoV-2 genome. All samples showed reads covering all of the targeted regions. FIG. 1E shows pipeline of RTNano real-time analysis. RTNano monitors the Nanopore MinION sequencing output folder. Once newly generated fastq files are detected, it moves the files to the analyzing folder and makes a new folder for each sample. If the Nanopore demultiplexing tool guppy is provided, RTNano will do additional demultiplexing to make sure reads are correctly classified. The analysis will align reads to the SARS-CoV-2 reference genome, filter, and count alignment records, and assign result mark (POS, NEG or UNK) for each sample. As sequencing proceeds, RTNano will merge the newly analyzed results with existing ones to update the current sequencing statistics.

FIG. 2A shows agarose gel electrophoresis results of singleplex RPA with selected primers shown next a molecular size marker. The amplicons range from 194 bp to 466 bp. FIG. 2B shows agarose gel electrophoresis results of restriction enzyme digestion. The amplicon of pair 5 was digested by SpeI while the others were digested by NlaIII. The digested DNA bands (asterisks) were of expected sizes. FIG. 2C shows agarose gel electrophoresis results showing the sensitivity of RPA in amplifying the SARS-CoV-2 genome. Primer pair 4 was used in the experiment. Reliable amplification can be achieved with 1.4 copies (calculated from dilution) of the SARS-CoV-2 genome. FIG. 2D shows agarose gel electrophoresis result of one-pot reverse transcription and RPA reaction using primer pair 4.

FIG. 3A shows the experimental design of multiple virus detection by one-pot NIRVANA. A mixture of SARS-CoV-$2^+$ and Respiratory$21^+$ samples was used as positive control to adjust the primer concentration. The final primer mix could amplify all targeted viral regions. FIG. 3B is the result of the sequencing throughput of 60 clinical samples (1-60) and NTC (61). A total of 6.3 million reads were acquired in a 24-hour sequencing run. FIG. 3C shows CT values of potentially false-negative samples by RTNano analysis. The average CT value of the N1 assay was indicated by the blue line. FIG. 3D shows the average rRT-PCR CT values of SARS-CoV-2 RTNano$^+$ samples (PCR$^+$ of both N1 and N2 assays) of different confidence level using 9-amplicon NIRVANA. The sample number is shown in red under the graph. RTNano confidence level inversely correlates with CT value. FIG. 3E shows IGV plots showing the read alignment to the SARS-CoV-2, ACTB, and FluA amplicon in sample 46 using 9-amplicon NIRVANA. FIG. 3F shows the SNVs detected in multiplex RPA sequencing and their position as shown in the Nextstrain data portal (Nextstrain.org). A total of 16 SNVs were detected from 10 SARS-CoV-2 positive samples.

FIG. 4A shows the read length distribution and throughput of ten SAR-CoV-$2^+$ sample sequencing. FIG. 4B shows the read number for each amplicon in the sequencing of ten SAR-CoV-$2^+$ samples. All amplicons were covered by reads. FIG. 4C shows the read number for each amplicon in the trial sequencing of multiplex RPA of SARS-CoV-2 and ACTB. Sample 01 is used as RPA template to determine the primer concentration in two trials (sample01_1 and sample01_2). Sample 02 is used in a repeat trial using the same primer mix as sample01_2. FIG. 4D shows the IGV alignment plot showing robust amplification of PMMoV with SARS-CoV-2. A SARS-CoV-$2^+$ sample (S4) was used as input sample in two trials with different primer concentration. FIG. 4E shows the CT values of FluA$^+$ samples in Resp'Easy™ and IDT FluA assays. FIG. 4F shows the average rRT-PCR CT values of SARS-CoV-2 RTNano$^+$ samples (PCR$^+$ of both N1 and N2 primers) of different confidence level using 7-amplicon NIRVANA. FIG. 4G shows the IGV plots showing the read alignment to SARS-CoV-2, ACTB and FluA amplicon in sample 58 using 7-amplicon NIRVANA.

FIG. 5A shows IGV plots showing the nt28144 T/C SNV in samples 01-03 from RPA and RT-PCR Nanopore sequencing. The blue bar represents the C base while the red bar represents the T base. All of the 3 SNVs detected in RPA sequencing were confirmed by RT-PCR amplicon sequencing. FIG. 5B shows the equipment used in NIRVANA. The whole workflow can be done with one laptop, one Nanopore MinION sequencer, two pipettes, two boxes of pipette tips, and a heating block (using a miniPCR™ mini16 here). All equipment can be packed into a suitcase.

DETAILED DESCRIPTION OF THE INVENTION

Figure 1A:
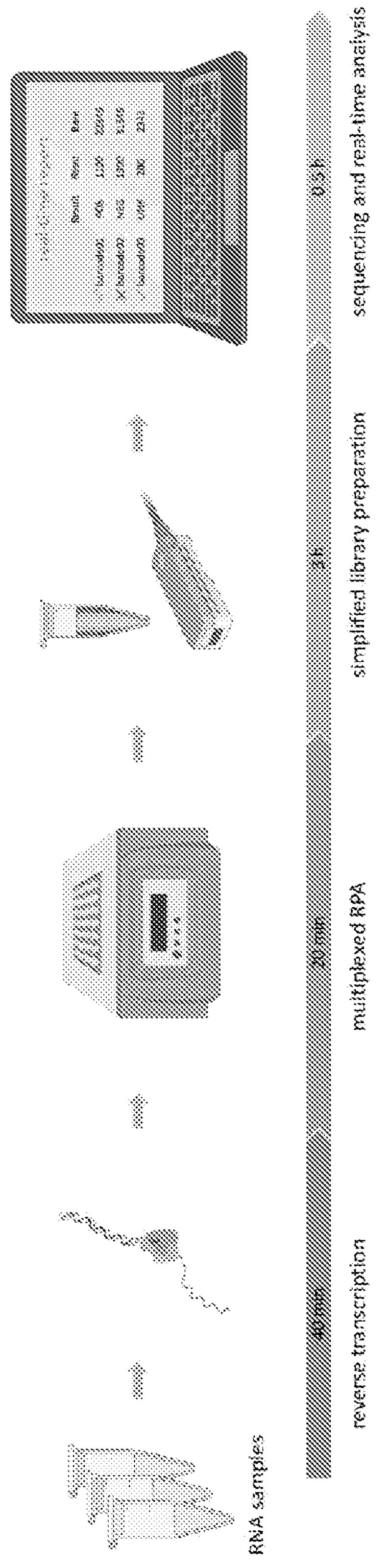
FIG. 1A-E shows multiplex RPA workflow for SARS-CoV-2 detection and Nanopore sequencing.

The disclosed compositions and method may be understood more readily by reference to the following detailed description of particular embodiments and the Example included therein and to the Figures and their previous and following description.

An isothermal recombinase polymerase amplification (RPA) assay is disclosed, to simultaneously amplify up to nine regions in four different viral genomes. Also disclosed is a method termed Nanopore sequencing of Isothermal Rapid Viral Amplification for Near real-time Analysis (NIRVANA), to detect the presence of viral sequences and monitor mutations in multiple regions of the genome in up to 96 patients at a time. A bioinformatics pipeline has been developed for on-the-fly demultiplexing and variant analysis to reduce the time to answer and sequencing cost by stopping the sequencing run when data are sufficient to provide confident answers. The whole workflow can be as short as 3.5 hours, and all reactions can be done in a simple heating block. NIRVANA provides a rapid field-deployable solution of COVID-19 and co-infection detection and surveillance of the evolution of pandemic strains.

A particularly preferred embodiment is demonstrated in the working examples.

It is to be understood that the disclosed compositions and method are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

I. Definitions

As used herein, the term "detect", "detecting", "determine" or "determining" generally refers to obtaining information. Detecting or determining can utilize any of a variety of techniques available to those skilled in the art, including for example specific techniques explicitly referred to herein. Detecting or determining may involve manipulation of a physical sample, consideration and/or manipulation of data or information, for example utilizing a computer or other processing unit adapted to perform a relevant analysis, and/or receiving relevant information and/or materials from a source. Detecting or determining may also mean comparing an obtained value to a known value, such as a known test value, a known control value, or a threshold value. Detecting or determining may also mean forming a conclusion based on the difference between the obtained value and the known value.

As used herein, the term "sample" refers to body fluids, body smears, cells, tissues, organs or portion thereof isolated from a subject. A sample may be a single cell or a plurality of cells. A sample may be a specimen obtained by biopsy (e.g., surgical biopsy). A sample may be one or more of cells, tissue, serum, plasma, urine, spittle, sputum, and stool. A sample may be one or more of a swab, fluid, blood, plasma, serum, urine, sputum, or exudate. In some embodiments, a sample includes viral nucleic acids, for example, viral DNA, viral RNA, or cDNA reverse transcribed from viral RNA. The sample can be used directly (e.g., fresh or frozen), or can be manipulated prior to use, for example, by heat-treatment, purification of nucleic acids, fixation (e.g., using formalin), and/or embedding in wax (such as FFPE tissue samples).

The terms "contact" or "contacting" describe placement in physical association for example, in solid and/or liquid form. For example, contacting can occur in vitro with one or more primers and/or probes and a biological sample (such as a sample including nucleic acids) in solution.

The term "variant" refers to a polypeptide or polynucleotide that differs from a reference polypeptide or polynucleotide. A typical variant of a polynucleotide has sequence alterations from another, reference polynucleotide. Generally, differences are limited so that the sequences of the reference and the variant are closely similar overall and, in many regions, identical. A variant and reference may differ in sequence by one or more modifications (e.g., substitutions, additions, and/or deletions). Exemplary variants" include substitutions (e.g., substitutions of single nucleic bases (single nucleotide variant; SNV or SNP) or multiple consecutive nucleic bases (multiple nucleotide variant; MNV)), indels (insertions and/or deletions less than 50 bp), insertions or deletions larger than 50 bp, and inversions. A variant of a polynucleotide may be naturally occurring such as an allelic variant, or it may be a variant that is not known to occur naturally.

"Amplification" or "amplifying" refers to increasing the number of copies of a nucleic acid molecule, such as a gene, fragment of a gene or other genomic region, for example at least a portion of an SARS-CoV-2 nucleic acid molecule. The products of an amplification reaction are called amplification products. Amplification techniques include recombinase polymerase amplification (RPA), polymerase chain reaction (PCR), real-time PCR, quantitative real-time PCR (qPCR), reverse transcription PCR (RT-PCR), quantitative RT-PCR (qRT-PCR), loop-mediated isothermal amplification (LAMP), reverse-transcriptase LAMP (RT-LAMP), strand displacement amplification, transcription-free isothermal amplification, repair chain reaction amplification, ligase chain reaction amplification, gap filling ligase chain reaction amplification, and coupled ligase detection and PCR.

As used herein, the term "diagnosing" refers to identifying the nature of a disease or condition that a subject may be suffering from. As used herein, the term "diagnosis" refers to the determination and/or conclusion that a subject suffers from a particular disease or condition or is infected with a virus. The term "diagnosing" may denote the virus' or disease's identification (e.g., by an authorized physician).

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of double-stranded DNA (dsDNA). A "reverse primer" anneals to the sense-strand of dsDNA.

As used herein, the term "subject," refers to any individual, organism or entity. The subject can be a vertebrate, for example, a mammal. Thus, the subject can be a human. A subject may be a non-human primate, domestic animal, farm animal, or a laboratory animal. For example, the subject may be a dog, cat, goat, horse, pig, mouse, rabbit, or the like. The subject may be a human. The subject may be healthy or suffering from or susceptible to a disease, disorder or condition. A patient refers to a subject afflicted with a disease or disorder. The term "patient" includes human and veterinary subjects.

"Treatment" or "treating" means to administer a composition to a subject or a system with an undesired condition (e.g., thalassemia). The condition can include one or more symptoms of a disease, pathological state, or disorder. Treatment includes medical management of a subject with the intent to cure, ameliorate, stabilize, or prevent a disease, pathological condition, or disorder. This includes active treatment, that is, treatment directed specifically toward the improvement of a disease, pathological state, or disorder, and also includes causal treatment, that is, treatment directed toward removal of the cause of the associated disease, pathological state, or disorder. In addition, this term includes palliative treatment, that is, treatment designed for the relief of symptoms rather than the curing of the disease, pathological state, or disorder; preventative treatment, that is, treatment directed to minimizing or partially or completely inhibiting the development of the associated disease, pathological state, or disorder; and supportive treatment, that is, treatment employed to supplement another specific therapy directed toward the improvement of the associated disease, pathological state, or disorder. It is understood that treatment, while intended to cure, ameliorate, stabilize, or prevent a disease, pathological condition, or disorder, need not actually result in the cure, amelioration, stabilization or prevention. In some specific embodiments, treatment means to administer a composition or therapy in an amount sufficient to reduce, alleviate or ameliorate one or more symptoms of a disorder, disease, or condition being treated. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied.

II. Methods of Detecting and Characterizing Viral Nucleic Acids

Methods of detecting or determining the presence of viral nucleic acids in a sample (such as a sample from a subject infected with or suspected to be infected with a virus) are disclosed. In preferred embodiments, the methods include an isothermal recombinase polymerase amplification (RPA) assay for detection of viral nucleic acids in a sample, such as a coronavirus nucleic acid. In some embodiments, the methods include detecting the viral nucleic acid in a sample and/or characterizing the nucleic acid to determine the presence of one or more genetic variants (e.g., mutations) in the nucleic acid. In some embodiments, the methods afford identification of a particular viral strain that may be present in the sample.

In a particular embodiment, a method for determining the presence of a viral nucleic acid in a sample involves (i) contacting the sample with a plurality of primers specific to the nucleic acid; (ii) performing a single reaction (e.g., RPA) to simultaneously amplify a plurality of target regions in the multiple viral nucleic acid, thereby generating a plurality of amplification products; and (iii) detecting the amplification products. Detection of amplification products indicates the presence of the viral nucleic acid in the sample.

In a particular embodiment, a method for detecting the presence of a viral nucleic acid in a sample and one or more mutations therein involves includes: (a) performing an isothermal recombinase polymerase amplification (RPA) on the sample to simultaneously amplify a plurality of target regions in the viral nucleic acid, thereby generating a plurality of amplification products; (b) sequencing the amplification products; (c) aligning the sequences to a reference viral genome/sequence, wherein sequencing read coverage across all the target regions indicates presence of the viral nucleic acid; and (d) determining the presence of one or more mutations in the sequences as compared to the reference.

The disclosed methods are highly sensitive and/or specific for detection of any viral nucleic acid of interest. In some examples, the disclosed methods can detect presence of at least 1 copy of a viral nucleic acid. For example at least 1, 2, 5, 10, 20, 50, 100, or more copies may be detected in a sample or reaction volume. In some embodiments, the methods can predict with a sensitivity of at least 75% and a specificity of at least 75% for presence of one or more of viral nucleic acids in a sample, such as a sensitivity of at least 80%, 85%, 90%, 95%, or even 100% and a specificity of at least of at least 80%, 85%, 90%, 95%, or even 100%.

The recent worldwide spread of the SARS-CoV-2 B.1.1.7 variant with an increased infectivity reveals an urgent need for rapid and field-deployable methods to monitor mutations in hopes of containing the spread of COVID-19 and ensuring the effectiveness of current vaccines. Alpha variant, also known as lineage B.1.1.7, is a variant of SARS-CoV-2. The two earliest genomes that belong to the B.1.1.7 lineage were collected on 20 Sep. 2020 in Kent and another on 21 Sep. 2020 in Greater London. These sequences were submitted to the GISAID sequence database (sequence accessions EPI_ISL_601443 and EPI_ISL_581117, respectively). One of the most important changes in B3.1.1.7 seems to be N501Y a change from asparagine (N) to tyrosine (Y) in amino-acid position 501. On 2 Feb. 2021, Public Health England reported that they had detected "[a] limited number of B.1.1.7 VOC-202012/01 genomes with E484K mutations", which is also present in the South Africa (Beta variant, also known as lineage B.1.351, and Brazil (Gamma variant, also known as lineage P.1) variants. The 9-amplicon NIRVANA covers three B.1.1.7-specific mutations and can be used for the identification of the variant. The framework of NIRVANA has a built-in flexibility in choosing what viral sequences to target and the level of multiplexing. The screening of new RPA primers can be performed at a low cost and with little effort.

A. Recombinase Polymerase Amplification (RPA)

A preferred technique for amplifying one or more target regions from the viral nucleic acid is RPA. RPA is a method that relies on the biological properties of a recombinase proteins (e.g., bacterial RecA or its prokaryotic and eukaryotic relatives). These proteins coat single-stranded DNA (ssDNA) to form filaments, which then scan double-stranded DNA (dsDNA) for regions of sequence homology. When homologous sequences are located, the nucleoprotein filament strand invades the dsDNA creating a short hybrid and a displaced strand bubble known as a D-loop. The free 3'-end of the filament strand in the D-loop can be extended by DNA polymerases to synthesize a new complementary strand. The complementary strand displaces the originally paired strand as it elongates. By utilizing pairs of oligonucleotides in a manner similar to that used in PCR, it is possible to amplify target DNA sequences in an analogous fashion but without any requirement for thermal melting (thermocycling). This has the advantage both of allowing the use of heat labile polymerases previously unusable in PCR, and increasing the fidelity and sensitivity by template scanning and strand invasion instead of hybridization.

In a particular embodiment of RPA, the isothermal amplification of specific DNA fragments is achieved by the binding of opposing oligonucleotide primers to template DNA and their extension by a polymerase. Recombinase-primer complexes scan double-stranded DNA and facilitate strand exchange at cognate sites. The resulting structures are stabilized by single-stranded DNA binding proteins (SSBs) interacting with the displaced template strand, thus preventing the ejection of the primer by branch migration. Recombinase disassembly leaves the 3'-end of the oligonucleotide accessible to a strand displacing DNA polymerase, and primer extension ensues. Exponential amplification is accomplished by the cyclic repetition of this process.

The target sequence to be amplified is preferably a double stranded DNA. However, the methods are not limited to double stranded DNA because other nucleic acid molecules, such as a single stranded DNA or RNA can be turned into double stranded DNA by one of skill in the arts using known methods. Suitable double stranded target DNA may be a genomic DNA or a cDNA. RPA may amplify a target nucleic acid at least 10 fold, preferably at least 100 fold, more preferably at least 1,000 fold, even more preferably at least 10,000 fold, and most preferably at least 1,000,000 fold.

Any suitable recombinase may be used in RPA. A recombinase is an enzyme that can coat single-stranded DNA (ssDNA) to form filaments, which can then scan double-stranded DNA (dsDNA) for regions of sequence homology. When homologous sequences are located, the nucleoprotein filament (comprising the recombinase agent) strand invades the dsDNA creating a short hybrid and a displaced strand bubble known as a D-loop. Suitable recombinase agents include the *E. coli* RecA protein, the T4 uvsX protein, or any homologous protein or protein complex from any phyla. Eukaryotic RecA homologues are generally named Rad51 after the first member of this group to be identified. Other non-homologous recombinase agents may be utilized in place of RecA, for example as RecT or RecO. Recombinase agents generally require the presence of ATP, ATPγS, or other nucleoside triphosphates and their analogs. Any derivatives and functional analogs of the recombinases above may be used as recombinases. For example, a small peptide from recA, which has been shown to retain some aspects of the recombination properties of recA, may be used. This peptide comprises residues 193 to 212 of *E. coli* recA and can mediate pairing of single stranded oligos (Oleg N. Voloshin, et al., DNA pairing Promoted by a 20-amino Acid Peptide Derived from RecA. Science Vol. 272 10 May 1996).

Exemplary single stranded DNA binding proteins include *E. coli* SSB, T4 gp32, or derivatives or combinations thereof such as, gp32(N), gp32(C), gp32(C)K3A, gp32(C)R4Q, gp32(C)R4T, gp32K3A, gp32R4Q, gp32R4T and a combination thereof.

The DNA polymerase may be a eukaryotic or prokaryotic polymerase. Examples of eukaryotic polymerases include pol-α, pol-β, pol-δ, pol-F and derivatives and combinations thereof. Examples of prokaryotic polymerase include *E. coli* DNA polymerase I Klenow fragment, bacteriophage T4 gp43 DNA polymerase, *Bacillus stearothermophilus* polymerase I large fragment, Phi-29 DNA polymerase, T7 DNA polymerase, *Bacillus subtilis* Pol I, *E. coli* DNA polymerase I, *E. coli* DNA polymerase II, *E. coli* DNA polymerase III, *E. coli* DNA polymerase IV, *E. coli* DNA polymerase V and derivatives and combinations thereof.

The RPA reaction is incubated for a period of time and at a temperature sufficient for production of an amplification product. The incubation temperature may be between 20° C. and 50° C., between 20° C. and 40° C., between 30° C. and 40° C., or between 20° C. and 30° C. One advantage of RPA over PCR is that thermocycling is not necessary. For example, in a field environment, it is sufficient to keep the RPA reaction at room temperature, or close to body temperature (e.g., 35° C. to 38° C.) by placing the sample in a body crevice. The RPA reaction is incubated for at least about 5 minutes (such as about 10, about 15, about 20, about 30, about 40, about 50, about 60 minutes or more), for example about 5-60 minutes, about 10-40 minutes, or about 20-30 minutes.

RPA can also be multiplexed through the addition of multiple primer sets with different specificities in a single reaction vessel (such as a tube, well, or other container). This capability is advantageous, for example, because it allows for incorporation of internal control(s), amplification of two or more regions within the same target, or detection of two or more targets or pathogens in a single reaction. In some embodiments, the methods include a multiplex RPA assay for detection and/or characterization of a plurality of target regions in a viral genome, such as a coronavirus genome.

In some embodiments, two or more (e.g., 2, 3, 4, 5, or more) pairs of primers are used. Thus, in some embodiments, a corresponding number of target regions (e.g., 2, 3, 4, 5, or more) is amplified. In preferred embodiments, 5 pairs of primers are used and/or 5 target regions are amplified. The target regions can include viral genomic regions that harbor signature mutations or mutation hotspots. In some embodiments, when the virus is SARS-CoV-2, target regions include genomic regions within the N gene, S gene, ORFlab, or ORF8 of a coronavirus. Exemplary primers include primers having a nucleic acid sequence that has at least 90% sequence identity to any one of SEQ ID NOs:2-11.

The sample and primers are contacted under conditions sufficient for amplification of the target regions of viral nucleic acid(s), producing amplification product(s). The sample is contacted with the plurality of primers at a concentration sufficient to support amplification of a desired viral nucleic acid(s). The term "conditions sufficient for" refers to any environment that permits the desired activity, for example, that permits specific binding or hybridization between two nucleic acid molecules or that permits reverse transcription and/or amplification of a nucleic acid. Such an environment may include, but is not limited to, particular incubation conditions (such as time and/or temperature) or presence and/or concentration of particular factors, for example in a solution (such as buffer(s), salt(s), metal ion(s), detergent(s), nucleotide(s), enzyme(s), etc.).

Primers are typically at least 10, 15, 18, or 30 nucleotides in length. In some embodiments, primers are preferably between about 15 to about 30 nucleotides in length, and more preferably between about 20 to about 25 nucleotides in length. However, there is no standard primer length for optimal hybridization or amplification. An optimal length for a particular primer application may be readily determined by those of skill in the art.

Variations and improvements to the general RPA method are well known in the art. See for example, US 2019/0360030, WO 2007/096702, and WO 2005/118853 which are specifically incorporated by reference in their entirety. RPA kits, such as the TwistAmp® Basic kit, are commercially available and are contemplated for use herein as well as LAMP, NASBA, helicase-dependent amplification (HDA), and nicking enzyme amplification reaction (NEAR.).

B. Detection & Characterization of Sequences

Following incubation of the RPA reaction, the amplification product(s) is detected by any suitable method. The detection methods may be quantitative, semi-quantitative, or qualitative. In some embodiments, accumulation of an amplification product is detected by gel electrophoresis, for example by detecting presence or amount of amplification product with agarose gel electrophoresis. The particular viral nucleic acid may be determined in some cases by the band pattern observed on gel electrophoresis. Amplification products can also be detected using a colorimetric assay, such as with an intercalating dye (for example, propidium iodide, SYBR green, GelRed™, or GelGreen™ dyes). Amplification products can also be detected with a metal ion sensitive fluorescent molecule (for example, calcein, which is a fluorescence dye that is quenched by manganese ions and has increased fluorescence when bound to magnesium ions).

In some embodiments, a sample is identified as containing a viral nucleic acid (for example is "positive" for the virus) if one or more amplifications products are detected (e.g., by any suitable quantitative, semi-quantitative, or qualitative approach). In some embodiments, a sample is identified as containing a viral nucleic acid (for example is "positive" for the virus) if an increase in fluorescence is detected compared to a control (such as a no template control sample or a known negative sample).

In some preferred embodiments, the amplification products are subjected to sequencing (e.g., sanger sequencing, next-generation sequencing, third-generation sequencing). Sequencing permits not only the detection of the viral nucleic acid by the identification of reads covering the amplified target regions, but also characterization of the viral sequence. This latter feature permits determination of the strain of a virus, its source, and/or evolution based on for example, the absence or presence of one or more mutations in the viral sequence. In some embodiments, a sample is identified as containing a viral nucleic acid (for example is "positive" for the virus) if sequence reads are detected for any targeted regions.

Suitable sequencing methods include, but are not limited to, sanger sequencing high-throughput sequencing, pyrosequencing, sequencing-by-synthesis, single-molecule sequencing, nanopore sequencing (e.g., MinION), semiconductor sequencing, sequencing-by-ligation, sequencing-by-hybridization, solexa sequencing (Illumina), Digital Gene Expression (Helicos), Next generation sequencing (e.g., Roche 454, Solexa platforms such as HiSeq2000, and SOLiD), Single Molecule Sequencing by Synthesis (SMSS) (Helicos), massively-parallel sequencing, Clonal Single Molecule Array (Solexa), Single Molecule Real Time sequencing (SMRT), shotgun sequencing, Maxim-Gilbert sequencing, primer walking, sequencing using PacBio, SOLiD, Ion Torrent, or Nanopore platforms and any other sequencing methods known in the art. In preferred embodiments, third generation sequencing is used. In preferred embodiments, sequencing is performed on an Oxford Nanopore MinION sequencer.

In some embodiments, a particular bioinformatic approach is used for the analysis of sequencing data. For example, when sequencing is performed on an Oxford Nanopore MinION sequencer, the bioinformatic approach (termed RTNano) intermittently scans the sequencing folder repeatedly based on user defined time intervals. Upon detection of newly generated sequencing results, the files are moved to an analysis folder. If necessary, the algorithm permits demultiplexing of the sequencing results to correctly classify reads. RTNano then align the sequencing reads to a reference viral genome (e.g., GenBank: NC_045512 in the case of SARS-CoV-2). After alignment, RTNano will filter the alignment records based on defined thresholds of parentage identity and amplicon coverage, followed by counting the alignment records of each amplicon. A read with >=89% alignment identity and >=96% amplicon coverage will be counted as one positive record. If an NTC barcode number was provided, RTNano will subtract this number in individual sample analysis to further ensure confident demultiplexing. In the end, RTNano will assign samples with different result marks (POS, NEG and UNK) based on the number of alignment records of each amplicon. As the sequencing continues, RTNano merges the newly analyzed result with completed ones to update the current sequencing statistics. Users can use this information to determine virus-positive samples in real time. In some embodiments, a positive sample is characterized by presence of reads covering all of the targeted regions. Identification of mutations or variants in the viral nucleic acid sequences can be performed using a variety of approaches standard in the art. For example, variants can be called using samtools (v1.9) and bcftools (v1.9). The detected variants can be compared to a database of viral genomes or variants (e.g., www.Nextstrain.org; www.gisaid.org) to assess evolution of the virus. In some embodiments, one or more of the following SARS-CoV-2 SNVs are detected 28144 T/C, 14408 C/T, and 23403 A/G.

C. Samples

The methods may be used for any purpose for which detection of viral nucleic acids is desirable, including diagnostic and prognostic applications, such as in laboratory and clinical settings. Appropriate samples include any conventional biological samples, including clinical samples obtained from a human or veterinary subject. Suitable samples include all biological samples useful for detection of infection in subjects, including, but not limited to, cells (such as buccal cells or peripheral blood mononuclear cells), tissues, autopsy samples, bone marrow aspirates, bodily fluids (for example, blood, serum, plasma, urine, cerebrospinal fluid, middle ear fluids, bronchoalveolar lavage, tracheal aspirates, sputum, nasopharyngeal aspirates, oropharyngeal aspirates, or saliva), oral swabs, eye swabs, cervical swabs, vaginal swabs, rectal swabs, stool, and stool suspensions.

In preferred embodiments, the sample is mucus, sputum (processed or unprocessed), bronchial alveolar lavage (BAL), bronchial wash (BW), cerebrospinal fluid (CSF), urine, tissue (e.g., biopsy material), rectal swab, nasopharyngeal aspirate, nasopharyngeal swab, throat swab, saliva, feces, mucosal excretions, plasma, serum, or whole blood. In some embodiments, the sample is a nucleic acid isolated and/or derived from any of the foregoing biological samples.

Generally, the sample is obtained non-invasively, such as by swabbing, scraping, collecting, drawing, or draining.

The sample can be used directly or can be processed, such as by adding solvents, preservatives, buffers, or other compounds or substances. In some examples, nucleic acids are isolated and/or derived from the sample. In other examples, isolation of nucleic acids from the sample is not necessary prior to use and the sample (such as a plasma or serum sample) is used directly (without nucleic acid extraction, but potentially with heat-treatment or other processing step). In some embodiments, the sample can be pre-treated with a lysis buffer, but nucleic acids are not isolated prior to use.

Samples also include isolated nucleic acids, such as DNA or RNA isolated from a biological specimen from a subject, a viral isolate, or other source of nucleic acids. The sample can also include DNA that is reverse transcribed from RNA isolated or extracted from a biological specimen from a subject, a viral isolate, or other source of nucleic acids. Methods for extracting nucleic acids such as RNA or DNA from a sample are known to one of skill in the art. Such methods will depend upon, for example, the type of sample in which the nucleic acid is found. Nucleic acids can be extracted using standard methods. For instance, rapid nucleic acid preparation can be performed using commercially available reagents/kit, such as kits and/or instruments from Invitrogen (TRIzol) Zymo Research (Direct-Zol RNA Miniprep kit), Qiagen (such as QiaAmpO, DNEasy® or RNEasy® kits), Roche Applied Science (such as MagNA Pure kits and instruments), Thermo Scientific (KingFisher mL), bioMerieux (Nuclisens® NASBA Diagnostics), or Epicentre (Masterpure™ kits). In some embodiments, the nucleic acids may be extracted using guanidinium isothiocyanate, such as single-step isolation by acid guanidinium isothiocyanate-phenol-chloroform extraction (Chomczynski et al. Anal. Biochem. 162:156-159, 1987).

D. Exemplary Viruses

The disclosed methods are suitable for the detection of any virus or nucleic acid therefrom. In some embodiments, the virus is a coronavirus, such as a severe acute respiratory syndrome-related coronavirus (e.g., SARS-CoV or SARS-CoV-2), influenza A (FluA), human adenovirus (HAdV), and non-SARS-CoV-2 human coronavirus (HCoV). The current classification of coronaviruses recognizes 39 species in 27 subgenera, five genera and two subfamilies that belong to the family Coronaviridae, suborder Cornidovirineae, order Nidovirales and realm Riboviria (Coronaviridae Study Group of the International Committee on Taxonomy of Viruses, *Nat Microbiol* 2020. DOI: 10.1038/s41564-020-0695-z). They are enveloped viruses with a positive-sense single-stranded RNA genome and a nucleocapsid of helical symmetry. The genome size of coronaviruses ranges from approximately 26 to 32 kilobases, one of the largest among RNA viruses.

Coronavirus species and representative viruses thereof include [representative virus (of species)]: SARSr-CoV BtKY72 (Severe acute respiratory syndrome-related coronavirus), SARS-CoV-2 (Severe acute respiratory syndrome-related coronavirus), and SARSr-CoV RaTG13 (Severe acute respiratory syndrome-related coronavirus), SARS-CoV PC4-227 (Severe acute respiratory syndrome-related coronavirus), SARS-CoV (Severe acute respiratory syndrome-related coronavirus), Bat-Hp-BetaCovC (BatHp-betacoronavirus Zhejiang2013), Ro-BatCoV GCCDC1 (Rousettus bat coronavirus GCCDC1), Ro-BatCoV HKU9 (Rousettus bat coronavirus HKU9), Ei-BatCoV C704 (Eidolon bat coronavirus C704), Pi-BatCoV HKU5 (*Pipistrellus* bat coronavirus HKU5), Ty-BatCoV HKU4 (*Tylonycteris* bar coronavirus HKU4), MERS-CoV (Middle East respiratory syndrome-related coronavirus), EriCoV (Hedgehog coronavirus), MHV (murine coronavirus), HCoV HKU1 (Human coronavirus HKUJ), ChRCoV HKU24 (China *Rattus* coronavirus HKU24), ChRCovC HKU24 (Betacoronavirus 1), MrufCoV 2JL14 (Myodes coronavirus 2JL14), HCoV NL63 (Human coronavirus NL63), HCoV 229E (Human coronavirus 229E), and HCoV OC43 (Human coronavirus OC43). See, e.g., Coronaviridae Study Group of the International Committee on Taxonomy of Viruses, *Nat Microbiol* 2020. DOI: 10.1038/s41564-020-0695-z), which is specifically incorporated by reference in its entirety. In some embodiments, the coronavirus is a common cold coronavirus such as 229E, NL63, OC43, and HKU1.

In particularly preferred embodiments, the virus is a Severe acute respiratory syndrome-related virus, preferably one that infects humans such as SARS-CoV or SARS-CoV-2 including variants thereof such as the SARS-CoV-2 B.1.1.7 variant.

Various strains of the foregoing viruses are known and include the representative genomic sequences provided as, for example, SEQ ID NO:1, the accession numbers provided herein, and those sequences and accession numbers provided in, e.g., Coronaviridae Study Group of the International Committee on Taxonomy of Viruses, *Nat Microbiol* 2020. DOI: 10.1038/s41564-020-0695-z). These, however, are non-limiting examples, and the disclosed methods can also be used to detect other strains of coronavirus, particularly SARS and MERS coronaviruses. In some embodiments, the (DNA sequence) of the viral genome has a sequence at least 80%, preferably at 85%, more preferably at least 86%, 87%, 88%, 89%, 90%, 91%, 92%, 93%, 94%, 95%, 96%, 97%, 98%, 99%, or 100% sequence identity to SEQ ID NO:1 or a sequence or accession number provided in Coronaviridae Study Group of the International Committee on Taxonomy of Viruses, *Nat Microbiol* 2020. DOI: 10.1038/s41564-020-0695-z, all of which are specifically incorporated by reference herein in their entireties. It will be appreciated that the sequences are provided as DNA sequences, but the viral genome itself will typically have the corresponding RNA sequences. Thus, the corresponding RNA sequences are also expressly provided herein.

GenBank Accession No. MN908947.3, which is specifically incorporated by reference herein in its entirety, provides the following (DNA) genomic sequence for SARS-CoV-2 (Severe acute respiratory syndrome coronavirus 2 isolate Wuhan-Hu-1, complete genome):

```
                                                    (SEQ ID NO: 1)
  1 attaaaggtt tataccttcc caggtaacaa accaaccaac tttcgatctc ttgtagatct

 61 gttctctaaa cgaactttaa aatctgtgtg gctgtcactc ggctgcatgc ttagtgcact

121 cacgcagtat aattaataac taattactgt cgttgacagg acacgagtaa ctcgtctatc

181 ttctgcaggc tgcttacggt ttcgtccgtg ttgcagccga tcatcagcac atctaggttt

241 cgtccgggtg tgaccgaaag gtaagatgga gagccttgtc cctggtttca acgagaaaac

301 acacgtccaa ctcagtttgc ctgttttaca ggttcgcgac gtgctcgtac gtggctttgg

361 agactccgtg gaggaggtct tatcagaggc acgtcaacat cttaaagatg gcacttgtgg

421 cttagtagaa gttgaaaaag gcgttttgcc tcaacttgaa cagccctatg tgttcatcaa

481 acgttcggat gctcgaactg cacctcatgg tcatgttatg gttgagctgg tagcagaact

541 cgaaggcatt cagtacggtc gtagtggtga gacacttggt gtccttgtcc ctcatgtggg
```

-continued

```
 601 cgaaatacca gtggcttacc gcaaggttct tcttcgtaag aacggtaata aaggagctgg
 661 tggccatagt tacggcgccg atctaaagtc atttgactta ggcgacgagc ttggcactga
 721 tccttatgaa gattttcaag aaaactggaa cactaaacat agcagtggtg ttacccgtga
 781 actcatgcgt gagcttaacg gaggggcata cactcgctat gtcgataaca acttctgtgg
 841 ccctgatggc taccctcttg agtgcattaa agaccttcta gcacgtgctg gtaaagcttc
 901 atgcactttg tccgaacaac tggactttat tgacactaag aggggtgtat actgctgccg
 961 tgaacatgag catgaaattg cttggtacac ggaacgttct gaaaagagct atgaattgca
1021 gacacctttt gaaattaaat tggcaaagaa atttgacacc ttcaatgggg aatgtccaaa
1081 ttttgtattt cccttaaatt ccataatcaa gactattcaa ccaagggttg aaaagaaaaa
1141 gcttgatggc tttatgggta gaattcgatc tgtctatcca gttgcgtcac caaatgaatg
1201 caaccaaatg tgcctttcaa ctctcatgaa gtgtgatcat tgtggtgaaa cttcatggca
1261 gacgggcgat tttgttaaag ccacttgcga attttgtggc actgagaatt tgactaaaga
1321 aggtgccact acttgtggtt acttacccca aaatgctgtt gttaaaattt attgtccagc
1381 atgtcacaat tcagaagtag gacctgagca tagtcttgcc gaataccata atgaatctgg
1441 cttgaaaacc attcttcgta agggtggtcg cactattgcc tttggaggct gtgtgttctc
1501 ttatgttggt tgccataaca agtgtgccta ttgggttcca cgtgctagcg ctaacatagg
1561 ttgtaaccat acaggtgttg ttggagaagg ttccgaaggt cttaatgaca accttcttga
1621 aatactccaa aaagagaaag tcaacatcaa tattgttggt gactttaaac ttaatgaaga
1681 gatcgccatt attttggcat ctttttctgc ttccacaagt gcttttgtgg aaactgtgaa
1741 aggtttggat tataaagcat tcaaacaaat tgttgaatcc tgtggtaatt ttaaagttac
1801 aaaaggaaaa gctaaaaaag gtgcctggaa tattggtgaa cagaaatcaa tactgagtcc
1861 tctttatgca tttgcatcag aggctgctcg tgttgtacga tcaattttct cccgcactct
1921 tgaaactgct caaaattctg tgcgtgtttt acagaaggcc gctataacaa tactagatgg
1981 aatttcacag tattcactga gactcattga tgctatgatg ttcacatctg atttggctac
2041 taacaatcta gttgtaatgg cctacattac aggtggtgtt gttcagttga cttcgcagtg
2101 gctaactaac atctttggca ctgtttatga aaaactcaaa cccgtccttg attggcttga
2161 agagaagttt aaggaaggtg tagagtttct tagagacggt tgggaaattg ttaaatttat
2221 ctcaacctgt gcttgtgaaa ttgtcggtgg acaaattgtc acctgtgcaa aggaaattaa
2281 ggagagtgtt cagacattct ttaagcttgt aaataaattt ttggctttgt gtgctgactc
2341 tatcattatt ggtggagcta aacttaaagc cttgaattta ggtgaaacat ttgtcacgca
2401 ctcaaaggga ttgtacagaa agtgtgttaa atccagagaa gaaactggcc tactcatgcc
2461 tctaaaagcc ccaaaagaaa ttatcttctt agagggagaa acacttccca cagaagtgtt
2521 aacagaggaa gttgtcttga aaactggtga tttacaacca ttagaacaac ctactagtga
2581 agctgttgaa gctccattgg ttggtacacc agtttgtatt aacgggctta tgttgctcga
2641 aatcaaagac acagaaaagt actgtgccct tgcacctaat atgatggtaa caaacaatac
2701 cttcacactc aaaggcggtg caccaacaaa ggttactttt ggtgatgaca ctgtgataga
2761 agtgcaaggt tacaagagtg tgaatatcac ttttgaactt gatgaaagga ttgataaagt
2821 acttaatgag aagtgctctg cctatacagt tgaactcggt acagaagtaa atgagttcgc
2881 ctgtgttgtg gcagatgctg tcataaaaac tttgcaacca gtatctgaat tacttacacc
2941 actgggcatt gatttagatg agtggagtat ggctacatac tacttatttg atgagtctgg
3001 tgagtttaaa ttggcttcac atatgtattg ttctttctac cctccagatg aggatgaaga
```

-continued 3061 agaaggtgat tgtgaagaag aagagtttga gccatcaact caatatgagt atggtactga
3121 agatgattac caaggtaaac ctttggaatt tggtgccact tctgctgctc ttcaacctga
3181 agaagagcaa gaagaagatt ggttagatga tgatagtcaa caaactgttg gtcaacaaga
3241 cggcagtgag gacaatcaga caactactat tcaaacaatt gttgaggttc aacctcaatt
3301 agagatggaa cttacaccag ttgttcagac tattgaagtg aatagtttta gtggttattt
3361 aaaacttact gacaatgtat acattaaaaa tgcagacatt gtggaagaag ctaaaaaggt
3421 aaaaccaaca gtggttgtta atgcagccaa tgtttacctt aaacatggag gaggtgttgc
3481 aggagcctta aataaggcta ctaacaatgc catgcaagtt gaatctgatg attacatagc
3541 tactaatgga ccacttaaag tgggtggtag ttgtgtttta agcggacaca atcttgctaa
3601 acactgtctt catgttgtcg gcccaaatgt taacaaaggt gaagacattc aacttcttaa
3661 gagtgcttat gaaaatttta atcagcacga agttctactt gcaccattat tatcagctgg
3721 tatttttggt gctgacccta tacattcttt aagagtttgt gtagatactg ttcgcacaaa
3781 tgtctactta gctgtctttg ataaaaatct ctatgacaaa cttgtttcaa gctttttgga
3841 aatgaagagt gaaaagcaag ttgaacaaaa gatcgctgag attcctaaag aggaagttaa
3901 gccatttata actgaaagta aaccttcagt tgaacagaga aaacaagatg ataagaaaat
3961 caaagcttgt gttgaagaag ttacaacaac tctggaagaa actaagttcc tcacagaaaa
4021 cttgttactt tatattgaca ttaatggcaa tcttcatcca gattctgcca ctcttgttag
4081 tgacattgac atcactttct taaagaaaga tgctccatat atagtgggtg atgttgttca
4141 agagggtgtt ttaactgctg tggttatacc tactaaaaag gctggtggca ctactgaaat
4201 gctagcgaaa gctttgagaa aagtgccaac agacaattat ataaccactt acccgggtca
4261 gggtttaaat ggttacactg tagaggaggc aaagacagtg cttaaaaagt gtaaaagtgc
4321 cttttacatt ctaccatcta ttatctctaa tgagaagcaa gaaattcttg gaactgtttc
4381 ttggaatttg cgagaaatgc ttgcacatgc agaagaaaca cgcaaattaa tgcctgtctg
4441 tgtggaaact aaagccatag tttcaactat acagcgtaaa tataagggta ttaaaataca
4501 agagggtgtg gttgattatg gtgctagatt ttacttttac accagtaaaa caactgtagc
4561 gtcacttatc aacacactta acgatctaaa tgaaactctt gttacaatgc cacttggcta
4621 tgtaacacat ggcttaaatt tggaagaagc tgctcggtat atgagatctc tcaaagtgcc
4681 agctacagtt tctgtttctt cacctgatgc tgttacagcg tataatggtt atcttacttc
4741 ttcttctaaa acacctgaag aacattttat tgaaaccatc tcacttgctg gttcctataa
4801 agattggtcc tattctggac aatctacaca actaggtata gaatttctta agagaggtga
4861 taaaagtgta tattacacta gtaatcctac cacattccac ctagatggtg aagttatcac
4921 ctttgacaat cttaagacac ttctttcttt gagagaagtg aggactatta aggtgtttac
4981 aacagtagac aacattaacc tccacacgca agttgtggac atgtcaatga catatggaca
5041 acagtttggt ccaacttatt tggatggagc tgatgttact aaaataaaac ctcataattc
5101 acatgaaggt aaaacatttt atgttttacc taatgatgac actctacgtg ttgaggcttt
5161 tgagtactac cacacaactg atcctagttt tctgggtagg tacatgtcag cattaaatca
5221 cactaaaaag tggaaatacc cacaagttaa tggtttaact tctattaaat gggcagataa
5281 caactgttat cttgccactg cattgttaac actccaacaa atagagttga agtttaatcc
5341 acctgctcta caagatgctt attacagagc aagggctggt gaagctgcta acttttgtgc
5401 acttatctta gcctactgta ataagacagt aggtgagtta ggtgatgtta gagaaacaat -continued 5461 gagttacttg tttcaacatg ccaatttaga ttcttgcaaa agagtcttga acgtggtgtg 5521 taaaacttgt ggacaacagc agacaaccct taagggtgta gaagctgtta tgtacatggg 5581 cacactttct tatgaacaat ttaagaaagg tgttcagata ccttgtacgt gtggtaaaca 5641 agctacaaaa tatctagtac aacaggagtc accttttgtt atgatgtcag caccacctgc 5701 tcagtatgaa cttaagcatg gtacatttac ttgtgctagt gagtacactg gtaattacca 5761 gtgtggtcac tataaacata taacttctaa agaaactttg tattgcatag acggtgcttt 5821 acttacaaag tcctcagaat acaaaggtcc tattacggat gttttctaca aagaaaacag 5881 ttacacaaca accataaaac cagttactta taaattggat ggtgttgttt gtacagaaat 5941 tgaccctaag ttggacaatt attataagaa agacaattct tatttcacag agcaaccaat 6001 tgatcttgta ccaaaccaac catatccaaa cgcaagcttc gataatttta agtttgtatg 6061 tgataatatc aaatttgctg atgatttaaa ccagttaact ggttataaga aacctgcttc 6121 aagagagctt aaagttacat ttttccctga cttaaatggt gatgtggtgg ctattgatta 6181 taaacactac acaccctctt ttaagaaagg agctaaattg ttacataaac ctattgtttg 6241 gcatgttaac aatgcaacta ataaagccac gtataaacca aatacctggt gtatacgttg 6301 tctttggagc acaaaaccag ttgaaacatc aaattcgttt gatgtactga agtcagagga 6361 cgcgcaggga atggataatc ttgcctgcga agatctaaaa ccagtctctg aagaagtagt 6421 ggaaaatcct accatacaga aagacgttct tgagtgtaat gtgaaaacta ccgaagttgt 6481 aggagacatt atacttaaac cagcaaataa tagtttaaaa attacagaag aggttggcca 6541 cacagatcta atggctgctt atgtagacaa ttctagtctt actattaaga aacctaatga 6601 attatctaga gtattaggtt tgaaaaccct tgctactcat ggtttagctg ctgttaatag 6661 tgtcccttgg gatactatag ctaattatgc taagcctttt cttaacaaag ttgttagtac 6721 aactactaac atagttacac ggtgtttaaa ccgtgtttgt actaattata tgccttattt 6781 ctttacttta ttgctacaat tgtgtacttt tactagaagt acaaattcta gaattaaagc 6841 atctatgccg actactatag caaagaatac tgttaagagt gtcggtaaat tttgtctaga 6901 ggcttcattt aattatttga agtcacctaa tttttctaaa ctgataaata ttataatttg 6961 gtttttacta ttaagtgttt gcctaggttc tttaatctac tcaaccgctg ctttaggtgt 7021 tttaatgtct aatttaggca tgccttctta ctgtactggt tacagagaag gctatttgaa 7081 ctctactaat gtcactattg caacctactg tactggttct ataccttgta gtgtttgtct 7141 tagtggttta gattctttag acacctatcc ttctttagaa actatacaaa ttaccatttc 7201 atcttttaaa tgggatttaa ctgcttttgg cttagttgca gagtggtttt tggcatatat 7261 tcttttcact aggtttttct atgtacttgg attggctgca atcatgcaat tgtttttcag 7321 ctattttgca gtacatttta ttagtaattc ttggcttatg tggttaataa ttaatcttgt 7381 acaaatggcc ccgatttcag ctatggttag aatgtacatc ttctttgcat cattttatta 7441 tgtatggaaa agttatgtgc atgttgtaga cggttgtaat tcatcaactt gtatgatgtg 7501 ttacaaacgt aatagagcaa caagagtcga atgtacaact attgttaatg gtgttagaag 7561 gtccttttat gtctatgcta atggaggtaa aggcttttgc aaactacaca attggaattg 7621 tgttaattgt gatacattct gtgctggtag tacatttatt agtgatgaag ttgcgagaga 7681 cttgtcacta cagtttaaaa gaccaataaa tcctactgac cagtcttctt acatcgttga 7741 tagtgttaca gtgaagaatg gttccatcca tctttacttt gataaagctg gtcaaaagac 7801 ttatgaaaga cattctctct ctcattttgt taacttagac aacctgagag ctaataacac 7861 taaaggttca ttgcctatta atgttatagt tttgatggt aaatcaaaat gtgaagaatc -continued

```
7921 atctgcaaaa tcagcgtctg tttactacag tcagcttatg tgtcaaccta tactgttact
7981 agatcaggca ttagtgtctg atgttggtga tagtgcggaa gttgcagtta aaatgtttga
8041 tgcttacgtt aatacgtttt catcaacttt taacgtacca atggaaaaac tcaaaacact
8101 agttgcaact gcagaagctg aacttgcaaa gaatgtgtcc ttagacaatg tcttatctac
8161 ttttatttca gcagctcggc aagggtttgt tgattcagat gtagaaacta aagatgttgt
8221 tgaatgtctt aaattgtcac atcaatctga catagaagtt actggcgata gttgtaataa
8281 ctatatgctc acctataaca aagttgaaaa catgacaccc cgtgaccttg gtgcttgtat
8341 tgactgtagt gcgcgtcata ttaatgcgca ggtagcaaaa agtcacaaca ttgctttgat
8401 atggaacgtt aaagatttca tgtcattgtc tgaacaacta cgaaaacaaa tacgtagtgc
8461 tgctaaaaag aataacttac cttttaagtt gacatgtgca actactagac aagttgttaa
8521 tgttgtaaca acaaagatag cacttaaggg tggtaaaatt gttaataatt ggttgaagca
8581 gttaattaaa gttacacttg tgttcctttt tgttgctgct attttctatt taataacacc
8641 tgttcatgtc atgtctaaac atactgactt ttcaagtgaa atcataggat acaaggctat
8701 tgatggtggt gtcactcgtg acatagcatc tacagatact tgttttgcta acaaacatgc
8761 tgattttgac acatggttta gccagcgtgg tggtagttat actaatgaca aagcttgccc
8821 attgattgct gcagtcataa caagagaagt gggttttgtc gtgcctggtt tgcctggcac
8881 gatattacgc acaactaatg gtgacttttt gcatttctta cctagagttt ttagtgcagt
8941 tggtaacatc tgttacacac catcaaaact tatagagtac actgactttg caacatcagc
9001 ttgtgttttg gctgctgaat gtacaatttt taaagatgct tctggtaagc cagtaccata
9061 ttgttatgat accaatgtac tagaaggttc tgttgcttat gaaagtttac gccctgacac
9121 acgttatgtg ctcatggatg gctctattat tcaatttcct aacacctacc ttgaaggttc
9181 tgttagagtg gtaacaactt ttgattctga gtactgtagg cacggcactt gtgaaagatc
9241 agaagctggt gtttgtgtat ctactagtgg tagatgggta cttaacaatg attattacag
9301 atctttacca ggagttttct gtggtgtaga tgctgtaaat ttacttacta atatgtttac
9361 accactaatt caacctattg gtgctttgga catatcagca tctatagtag ctggtggtat
9421 tgtagctatc gtagtaacat gccttgccta ctattttatg aggtttagaa gagcttttgg
9481 tgaatacagt catgtagttg cctttaatac tttactattc cttatgtcat tcactgtact
9541 ctgtttaaca ccagtttact cattcttacc tggtgtttat tctgttattt acttgtactt
9601 gacattttat cttactaatg atgtttcttt tttagcacat attcagtgga tggttatgtt
9661 cacaccttta gtacctttct ggataacaat tgcttatatc atttgtattt ccacaaagca
9721 tttctattgg ttctttagta attacctaaa gagacgtgta gtctttaatg gtgtttcctt
9781 tagtactttt gaagaagctg cgctgtgcac ctttttgtta aataaagaaa tgtatctaaa
9841 gttgcgtagt gatgtgctat tacctcttac gcaatataat agatacttag ctctttataa
9901 taagtacaag tattttagtg gagcaatgga tacaactagc tacagagaag ctgcttgttg
9961 tcatctcgca aaggctctca atgacttcag taactcaggt tctgatgttc tttaccaacc
10021 accacaaacc tctatcacct cagctgtttt gcagagtggt tttagaaaaa tggcattccc
10081 atctggtaaa gttgagggtt gtatggtaca agtaacttgt ggtacaacta cacttaacgg
10141 tctttggctt gatgacgtag tttactgtcc aagacatgtg atctgcacct ctgaagacat
10201 gcttaaccct aattatgaag atttactcat tcgtaagtct aatcataatt tcttggtaca
10261 ggctggtaat gttcaactca gggttattgg acattctatg caaaattgtg tacttaagct
```

-continued 10321 taaggttgat acagccaatc ctaagacacc taagtataag tttgttcgca ttcaaccagg 10381 acagactttt tcagtgttag cttgttacaa tggttcacca tctggtgttt accaatgtgc 10441 tatgaggccc aatttcacta ttaagggttc attccttaat ggttcatgtg gtagtgttgg 10501 ttttaacata gattatgact gtgtctcttt ttgttacatg caccatatgg aattaccaac 10561 tggagttcat gctggcacag acttagaagg taacttttat ggaccttttg ttgacaggca 10621 aacagcacaa gcagctggta cggacacaac tattacagtt aatgttttag cttggttgta 10681 cgctgctgtt ataaatggag acaggtggtt tctcaatcga tttaccacaa ctcttaatga 10741 ctttaacctt gtggctatga agtacaatta tgaacctcta acacaagacc atgttgacat 10801 actaggacct ctttctgctc aaactggaat tgccgtttta gatatgtgtg cttcattaaa 10861 agaattactg caaaatggta tgaatggacg taccatattg ggtagtgctt tattagaaga 10921 tgaatttaca ccttttgatg ttgttagaca atgctcaggt gttactttcc aaagtgcagt 10981 gaaaagaaca atcaagggta cacaccactg gttgttactc acaattttga cttcactttt 11041 agttttagtc cagagtactc aatggtcttt gttctttttt ttgtatgaaa atgccttttt 11101 accttttgct atgggtatta ttgctatgtc tgcttttgca atgatgtttg tcaaacataa 11161 gcatgcattt ctctgtttgt ttttgttacc ttctcttgcc actgtagctt attttaatat 11221 ggtctatatg cctgctagtt gggtgatgcg tattatgaca tggttggata tggttgatac 11281 tagtttgtct ggttttaagc taaaagactg tgttatgtat gcatcagctg tagtgttact 11341 aatccttatg acagcaagaa ctgtgtatga tgatggtgct aggagagtgt ggacacttat 11401 gaatgtcttg acactcgttt ataaagttta ttatggtaat gctttagatc aagccatttc 11461 catgtgggct cttataatct ctgttacttc taactactca ggtgtagtta caactgtcat 11521 gtttttggcc agaggtattg tttttatgtg tgttgagtat tgccctattt tcttcataac 11581 tggtaataca cttcagtgta taatgctagt ttattgtttc ttaggctatt tttgtacttg 11641 ttactttggc ctcttttgtt tactcaaccg ctactttaga ctgactcttg gtgtttatga 11701 ttacttagtt tctacacagg agtttagata tatgaattca cagggactac tcccacccaa 11761 gaatagcata gatgccttca aactcaacat taaattgttg ggtgttggtg gcaaaccttg 11821 tatcaaagta gccactgtac agtctaaaat gtcagatgta aagtgcacat cagtagtctt 11881 actctcagtt ttgcaacaac tcagagtaga atcatcatct aaattgtggg ctcaatgtgt 11941 ccagttacac aatgacattc tcttagctaa agatactact gaagcctttg aaaaaatggt 12001 ttcactactt tctgttttgc tttccatgca gggtgctgta gacataaaca agctttgtga 12061 agaaatgctg gacaacaggg caaccttaca agctatagcc tcagagttta gttcccttcc 12121 atcatatgca gcttttgcta ctgctcaaga agcttatgag caggctgttg ctaatggtga 12181 ttctgaagtt gttcttaaaa agttgaagaa gtctttgaat gtggctaaat ctgaatttga 12241 ccgtgatgca gccatgcaac gtaagttgga aaagatggct gatcaagcta tgacccaaat 12301 gtataaacag gctagatctg aggacaagag ggcaaaagtt actagtgcta tgcagacaat 12361 gcttttcact atgcttagaa agttggataa tgatgcactc aacaacatta tcaacaatgc 12421 aagagatggt tgtgttccct tgaacataat acctcttaca acagcagcca aactaatggt 12481 tgtcatacca gactataaca catataaaaa tacgtgtgat ggtacaacat ttacttatgc 12541 atcagcattg tgggaaatcc aacaggttgt agatgcagat agtaaaattg ttcaacttag 12601 tgaaattagt atggacaatt cacctaattt agcatggcct cttattgtaa cagctttaag 12661 ggccaattct gctgtcaaat tacagaataa tgagcttagt cctgttgcac tacgacagat 12721 gtcttgtgct gccggtacta cacaaactgc ttgcactgat gacaatgcgt tagcttacta -continued 12781 caacacaaca aagggaggta ggtttgtact tgcactgtta tccgatttac aggatttgaa 12841 atgggctaga ttccctaaga gtgatggaac tggtactatc tatacagaac tggaaccacc 12901 ttgtaggttt gttacagaca cacctaaagg tcctaaagtg aagtatttat actttattaa 12961 aggattaaac aacctaaata gaggtatggt acttggtagt ttagctgcca cagtacgtct 13021 acaagctggt aatgcaacag aagtgcctgc caattcaact gtattatctt tctgtgcttt 13081 tgctgtagat gctgctaaag cttacaaaga ttatctagct agtgggggac aaccaatcac 13141 taattgtgtt aagatgttgt gtacacacac tggtactggt caggcaataa cagttacacc 13201 ggaagccaat atggatcaag aatcctttgg tggtgcatcg tgttgtctgt actgccgttg 13261 ccacatagat catccaaatc ctaaaggatt ttgtgactta aaaggtaagt atgtacaaat 13321 acctacaact tgtgctaatg accctgtggg ttttacactt aaaaacacag tctgtaccgt 13381 ctgcggtatg tggaaaggtt atggctgtag ttgtgatcaa ctccgcgaac ccatgcttca 13441 gtcagctgat gcacaatcgt ttttaaacgg gtttgcggtg taagtgcagc ccgtcttaca 13501 ccgtgcggca caggcactag tactgatgtc gtatacaggg cttttgacat ctacaatgat 13561 aaagtagctg gttttgctaa attcctaaaa actaattgtt gtcgcttcca agaaaaggac 13621 gaagatgaca atttaattga ttcttacttt gtagttaaga gacacacttt ctctaactac 13681 caacatgaag aaacaattta taatttactt aaggattgtc cagctgttgc taaacatgac 13741 ttctttaagt ttagaataga cggtgacatg gtaccacata tatcacgtca acgtcttact 13801 aaatacacaa tggcagacct cgtctatgct ttaaggcatt ttgatgaagg taattgtgac 13861 acattaaaag aaatacttgt cacatacaat tgttgtgatg atgattattt caataaaaag 13921 gactggtatg attttgtaga aaacccagat atattacgcg tatacgccaa cttaggtgaa 13981 cgtgtacgcc aagctttgtt aaaaacagta caattctgtg atgccatgcg aaatgctggt 14041 attgttggtg tactgacatt agataatcaa gatctcaatg gtaactggta tgatttcggt 14101 gatttcatac aaaccacgcc aggtagtgga gttcctgttg tagattctta ttattcattg 14161 ttaatgccta tattaacctt gaccagggct ttaactgcag agtcacatgt tgacactgac 14221 ttaacaaagc cttacattaa gtgggatttg ttaaaatatg acttcacgga agagaggtta 14281 aaactctttg accgttattt taaatattgg gatcagacat accacccaaa ttgtgttaac 14341 tgtttggatg acagatgcat tctgcattgt gcaaacttta atgttttatt ctctacagtg 14401 ttcccaccta caagttttgg accactagtg agaaaaatat ttgttgatgg tgttccattt 14461 gtagtttcaa ctggatacca cttcagagag ctaggtgttg tacataatca ggatgtaaac 14521 ttacatagct ctagacttag ttttaaggaa ttacttgtgt atgctgctga ccctgctatg 14581 cacgctgctt ctggtaatct attactagat aaacgcacta cgtgcttttc agtagctgca 14641 cttactaaca atgttgcttt tcaaactgtc aaacccggta attttaacaa agacttctat 14701 gactttgctg tgtctaaggg tttctttaag gaaggaagtt ctgttgaatt aaaacacttc 14761 ttctttgctc aggatggtaa tgctgctatc agcgattatg actactatcg ttataatcta 14821 ccaacaatgt gtgatatcag acaactacta tttgtagttg aagttgttga taagtacttt 14881 gattgttacg atggtggctg tattaatgct aaccaagtca tcgtcaacaa cctagacaaa 14941 tcagctggtt ttccatttaa taaatggggt aaggctagac tttattatga ttcaatgagt 15001 tatgaggatc aagatgcact tttcgcatat acaaaacgta atgtcatccc tactataact 15061 caaatgaatc ttaagtatgc cattagtgca aagaatagag ctcgcaccgt agctggtgtc 15121 tctatctgta gtactatgac caatagacag tttcatcaaa aattattgaa atcaatagcc -continued 15181 gccactagag gagctactgt agtaattgga acaagcaaat tctatggtgg ttggcacaac 15241 atgttaaaaa ctgtttatag tgatgtagaa aaccctcacc ttatgggttg ggattatcct 15301 aaatgtgata gagccatgcc taacatgctt agaattatgg cctcacttgt tcttgctcgc 15361 aaacatacaa cgtgttgtag cttgtcacac cgtttctata gattagctaa tgagtgtgct 15421 caagtattga gtgaaatggt catgtgtggc ggttcactat atgttaaacc aggtggaacc 15481 tcatcaggag atgccacaac tgcttatgct aatagtgttt ttaacatttg tcaagctgtc 15541 acggccaatg ttaatgcact tttatctact gatggtaaca aaattgccga taagtatgtc 15601 cgcaatttac aacacagact ttatgagtgt ctctatagaa atagagatgt tgacacagac 15661 tttgtgaatg agttttacgc atatttgcgt aaacatttct caatgatgat actctctgac 15721 gatgctgttg tgtgtttcaa tagcacttat gcatctcaag gtctagtggc tagcataaag 15781 aactttaagt cagttcttta ttatcaaaac aatgttttta tgtctgaagc aaaatgttgg 15841 actgagactg accttactaa aggacctcat gaattttgct ctcaacatac aatgctagtt 15901 aaacagggtg atgattatgt gtaccttcct tacccagatc catcaagaat cctaggggcc 15961 ggctgttttg tagatgatat cgtaaaaaca gatggtacac ttatgattga acggttcgtg 16021 tctttagcta tagatgctta cccacttact aaacatccta atcaggagta tgctgatgtc 16081 tttcatttgt acttacaata cataagaaag ctacatgatg agttaacagg acacatgtta 16141 gacatgtatt ctgttatgct tactaatgat aacacttcaa ggtattggga acctgagttt 16201 tatgaggcta tgtacacacc gcatacagtc ttacaggctg ttggggcttg tgttctttgc 16261 aattcacaga cttcattaag atgtggtgct tgcatacgta gaccattctt atgttgtaaa 16321 tgctgttacg accatgtcat atcaacatca cataaattag tcttgtctgt taatccgtat 16381 gtttgcaatg ctccaggttg tgatgtcaca gatgtgactc aactttactt aggaggtatg 16441 agctattatt gtaaatcaca taaaccaccc attagttttc cattgtgtgc taatggacaa 16501 gtttttggtt tatataaaaa tacatgtgtt ggtagcgata atgttactga ctttaatgca 16561 attgcaacat gtgactggac aaatgctggt gattacattt tagctaacac ctgtactgaa 16621 agactcaagc tttttgcagc agaaacgctc aaagctactg aggagacatt taaactgtct 16681 tatggtattg ctactgtacg tgaagtgctg tctgacagag aattacatct ttcatgggaa 16741 gttggtaaac ctagaccacc acttaaccga aattatgtct ttactggtta tcgtgtaact 16801 aaaaacagta aagtacaaat aggagagtac acctttgaaa aaggtgacta tggtgatgct 16861 gttgtttacc gaggtacaac aacttacaaa ttaaatgttg gtgattattt tgtgctgaca 16921 tcacatacag taatgccatt aagtgcacct acactagtgc cacaagagca ctatgttaga 16981 attactggct tatacccaac actcaatatc tcagatgagt tttctagcaa tgttgcaaat 17041 tatcaaaagg ttggtatgca aaagtattct acactccagg gaccacctgg tactggtaag 17101 agtcattttg ctattggcct agctctctac tacccttctg ctcgcatagt gtatacagct 17161 tgctctcatg ccgctgttga tgcactatgt gagaaggcat taaaatattt gcctatagat 17221 aaatgtagta gaattatacc tgcacgtgct cgtgtagagt gttttgataa attcaaagtg 17281 aattcaacat tagaacagta tgtcttttgt actgtaaatg cattgcctga gacgacagca 17341 gatatagttg tctttgatga aatttcaatg gccacaaatt atgatttgag tgttgtcaat 17401 gccagattac gtgctaagca ctatgtgtac attggcgacc ctgctcaatt acctgcacca 17461 cgcacattgc taactaaggg cacactagaa ccagaatatt tcaattcagt gtgtagactt 17521 atgaaaacta taggtccaga catgttcctc ggaacttgtc ggcgttgtcc tgctgaaatt 17581 gttgacactg tgagtgcttt ggtttatgat aataagctta aagcacataa agacaaatca -continued 17641 gctcaatgct ttaaaatgtt ttataagggt gttatcacgc atgatgtttc atctgcaatt 17701 aacaggccac aaataggcgt ggtaagagaa ttccttacac gtaaccctgc ttggagaaaa 17761 gctgtcttta tttcacctta taattcacag aatgctgtag cctcaaagat tttgggacta 17821 ccaactcaaa ctgttgattc atcacagggc tcagaatatg actatgtcat attcactcaa 17881 accactgaaa cagctcactc ttgtaatgta aacagattta atgttgctat taccagagca 17941 aaagtaggca tactttgcat aatgtctgat agagaccttt atgacaagtt gcaatttaca 18001 agtcttgaaa ttccacgtag gaatgtggca actttacaag ctgaaaatgt aacaggactc 18061 tttaaagatt gtagtaaggt aatcactggg ttacatccta cacaggcacc tacacacctc 18121 agtgttgaca ctaaattcaa aactgaaggt ttatgtgttg acatacctgg catacctaag 18181 gacatgacct atagaagact catctctatg atgggtttta aaatgaatta tcaagttaat 18241 ggttacccta acatgtttat cacccgcgaa gaagctataa gacatgtacg tgcatggatt 18301 ggcttcgatg tcgaggggtg tcatgctact agagaagctg ttggtaccaa tttaccttta 18361 cagctaggtt tttctacagg tgttaaccta gttgctgtac ctacaggtta tgttgataca 18421 cctaataata cagatttttc cagagttagt gctaaaccac cgcctggaga tcaatttaaa 18481 cacctcatac cacttatgta caaaggactt ccttggaatg tagtgcgtat aaagattgta 18541 caaatgttaa gtgacacact taaaaatctc tctgacagag tcgtatttgt cttatgggca 18601 catggctttg agttgacatc tatgaagtat tttgtgaaaa taggacctga gcgcacctgt 18661 tgtctatgtg atagacgtgc cacatgcttt tccactgctt cagacactta tgcctgttgg 18721 catcattcta ttggatttga ttacgtctat aatccgttta tgattgatgt tcaacaatgg 18781 ggttttacag gtaacctaca aagcaaccat gatctgtatt gtcaagtcca tggtaatgca 18841 catgtagcta gttgtgatgc aatcatgact aggtgtctag ctgtccacga gtgctttgtt 18901 aagcgtgttg actggactat tgaatatcct ataattggtg atgaactgaa gattaatgcg 18961 gcttgtagaa aggttcaaca catggttgtt aaagctgcat tattagcaga caaattccca 19021 gttcttcacg acattggtaa ccctaaagct attaagtgtg tacctcaagc tgatgtagaa 19081 tggaagttct atgatgcaca gccttgtagt gacaaagctt ataaaataga agaattattc 19141 tattcttatg ccacacattc tgacaaattc acagatggtg tatgcctatt ttggaattgc 19201 aatgtcgata gatatcctgc taattccatt gtttgtagat ttgacactag agtgctatct 19261 aaccttaact tgcctggttg tgatggtggc agtttgtatg taaataaaca tgcattccac 19321 acaccagctt ttgataaaag tgcttttgtt aatttaaaac aattaccatt tttctattac 19381 tctgacagtc catgtgagtc tcatggaaaa caagtagtgt cagatataga ttatgtacca 19441 ctaaagtctg ctacgtgtat aacacgttgc aatttaggtg gtgctgtctg tagacatcat 19501 gctaatgagt acagattgta tctcgatgct tataacatga tgatctcagc tggctttagc 19561 ttgtgggttt acaaacaatt tgatacttat aacctctgga acacttttac aagacttcag 19621 agtttagaaa atgtggcttt taatgttgta aataagggac actttgatgg acaacagggt 19681 gaagtaccag tttctatcat taataacact gtttacacaa aagttgatgg tgttgatgta 19741 gaattgtttg aaaataaaac aacattacct gttaatgtag catttgagct ttgggctaag 19801 cgcaacatta aaccagtacc agaggtgaaa atactcaata atttgggtgt ggacattgct 19861 gctaatactg tgatctggga ctacaaaaga gatgctccag cacatatatc tactattggt 19921 gtttgttcta tgactgacat agccaagaaa ccaactgaaa cgatttgtgc accactcact 19981 gtcttttttg atggtagagt tgatggtcaa gtagacttat ttagaaatgc ccgtaatggt -continued

```
20041 gttcttatta cagaaggtag tgttaaaggt ttacaaccat ctgtaggtcc caaacaagct
20101 agtcttaatg gagtcacatt aattggagaa gccgtaaaaa cacagttcaa ttattataag
20161 aaagttgatg gtgttgtcca acaattacct gaaacttact ttactcagag tagaaattta
20221 caagaattta aacccaggag tcaaatggaa attgatttct tagaattagc tatggatgaa
20281 ttcattgaac ggtataaatt agaaggctat gccttcgaac atatcgttta tggagatttt
20341 agtcatagtc agttaggtgg tttacatcta ctgattggac tagctaaacg ttttaaggaa
20401 tcaccttttg aattagaaga ttttattcct atggacagta cagttaaaaa ctatttcata
20461 acagatgcgc aaacaggttc atctaagtgt gtgtgttctg ttattgattt attacttgat
20521 gattttgttg aaataataaa atcccaagat ttatctgtag tttctaaggt tgtcaaagtg
20581 actattgact atacagaaat ttcatttatg ctttggtgta aagatggcca tgtagaaaca
20641 ttttacccaa aattacaatc tagtcaagcg tggcaaccgg gtgttgctat gcctaatctt
20701 tacaaaatgc aaagaatgct attagaaaag tgtgaccttc aaaattatgg tgatagtgca
20761 acattaccta aaggcataat gatgaatgtc gcaaaatata ctcaactgtg tcaatattta
20821 aacacattaa cattagctgt accctataat atgagagtta tacattttgg tgctggttct
20881 gataaaggag ttgcaccagg tacagctgtt ttaagacagt ggttgcctac gggtacgctg
20941 cttgtcgatt cagatcttaa tgactttgtc tctgatgcag attcaacttt gattggtgat
21001 tgtgcaactg tacatacagc taataaatgg gatctcatta ttagtgatat gtacgaccct
21061 aagactaaaa atgttacaaa agaaaatgac tctaaagagg gtttttcac ttacatttgt
21121 gggtttatac aacaaaagct agctcttgga ggttccgtgg ctataaagat aacagaacat
21181 tcttggaatg ctgatcttta taagctcatg ggacacttcg catggtggac agcctttgtt
21241 actaatgtga atgcgtcatc atctgaagca tttttaattg gatgtaatta tcttggcaaa
21301 ccacgcgaac aaatagatgg ttatgtcatg catgcaaatt acatattttg gaggaataca
21361 aatccaattc agttgtcttc ctattcttta tttgacatga gtaaatttcc ccttaaatta
21421 aggggtactg ctgttatgtc tttaaaagaa ggtcaaatca atgatatgat tttatctctt
21481 cttagtaaag gtagacttat aattagagaa aacaacagag ttgttatttc tagtgatgtt
21541 cttgttaaca actaaacgaa caatgtttgt ttttcttgtt ttattgccac tagtctctag
21601 tcagtgtgtt aatcttacaa ccagaactca attacccct gcatacacta attctttcac
21661 acgtggtgtt tattaccctg acaaagtttt cagatcctca gttttacatt caactcagga
21721 cttgttctta cctttctttt ccaatgttac ttggttccat gctatacatg tctctgggac
21781 caatggtact aagaggtttg ataaccctgt cctaccattt aatgatggtg tttattttgc
21841 ttccactgag aagtctaaca taataagagg ctggattttt ggtactactt tagattcgaa
21901 gacccagtcc ctacttattg ttaataacgc tactaatgtt gttattaaag tctgtgaatt
21961 tcaattttgt aatgatccat ttttgggtgt ttattaccac aaaaacaaca aaagttggat
22021 ggaaagtgag ttcagagttt attctagtgc gaataattgc acttttgaat atgtctctca
22081 gccttttctt atggaccttg aaggaaaaca gggtaatttc aaaaatctta gggaatttgt
22141 gtttaagaat attgatggtt attttaaaat atattctaag cacacgccta ttaatttagt
22201 gcgtgatctc cctcagggtt tttcggcttt agaaccattg gtagatttgc caataggtat
22261 taacatcact aggtttcaaa ctttacttgc tttacataga agttatttga ctcctggtga
22321 ttcttcttca ggttggacag ctggtgctgc agcttattat gtgggttatc ttcaacctag
22381 gacttttcta ttaaaatata atgaaaatgg aaccattaca gatgctgtag actgtgcact
22441 tgaccctctc tcagaaacaa agtgtacgtt gaaatccttc actgtagaaa aaggaatcta
```

-continued 22501 tcaaacttct aactttagag tccaaccaac agaatctatt gttagatttc ctaatattac 22561 aaacttgtgc ccttttggtg aagtttttaa cgccaccaga tttgcatctg tttatgcttg 22621 gaacaggaag agaatcagca actgtgttgc tgattattct gtcctatata attccgcatc 22681 attttccact tttaagtgtt atggagtgtc tcctactaaa ttaaatgatc tctgctttac 22741 taatgtctat gcagattcat ttgtaattag aggtgatgaa gtcagacaaa tcgctccagg 22801 gcaaactgga aagattgctg attataatta taaattacca gatgatttta caggctgcgt 22861 tatagcttgg aattctaaca atcttgattc taaggttggt ggtaattata attacctgta 22921 tagattgttt aggaagtcta atctcaaacc ttttgagaga gatatttcaa ctgaaatcta 22981 tcaggccggt agcacacctt gtaatggtgt tgaaggtttt aattgttact ttcctttaca 23041 atcatatggt ttccaaccca ctaatggtgt tggttaccaa ccatacagag tagtagtact 23101 ttcttttgaa cttctacatg caccagcaac tgtttgtgga cctaaaaagt ctactaattt 23161 ggttaaaaac aaatgtgtca atttcaactt caatggttta acaggcacag gtgttcttac 23221 tgagtctaac aaaaagtttc tgcctttcca acaatttggc agagacattg ctgacactac 23281 tgatgctgtc cgtgatccac agacacttga gattcttgac attacaccat gttcttttgg 23341 tggtgtcagt gttataacac caggaacaaa tacttctaac caggttgctg ttctttatca 23401 ggatgttaac tgcacagaag tccctgttgc tattcatgca gatcaactta ctcctacttg 23461 gcgtgtttat tctacaggtt ctaatgtttt tcaaacacgt gcaggctgtt taataggggc 23521 tgaacatgtc aacaactcat atgagtgtga catacccatt ggtgcaggta tatgcgctag 23581 ttatcagact cagactaatt ctcctcggcg ggcacgtagt gtagctagtc aatccatcat 23641 tgcctacact atgtcacttg gtgcagaaaa ttcagttgct tactctaata actctattgc 23701 catacccaca aattttacta ttagtgttac cacagaaatt ctaccagtgt ctatgaccaa 23761 gacatcagta gattgtacaa tgtacatttg tggtgattca actgaatgca gcaatctttt 23821 gttgcaatat ggcagttttt gtacacaatt aaaccgtgct ttaactggaa tagctgttga 23881 acaagacaaa aacacccaag aagtttttgc acaagtcaaa caaatttaca aaacaccacc 23941 aattaaagat tttggtggtt ttaatttttc acaaatatta ccagatccat caaaaccaag 24001 caagaggtca tttattgaag atctactttt caacaaagtg acacttgcag atgctggctt 24061 catcaaacaa tatggtgatt gccttggtga tattgctgct agagacctca tttgtgcaca 24121 aaagtttaac ggccttactg ttttgccacc tttgctcaca gatgaaatga ttgctcaata 24181 cacttctgca ctgttagcgg gtacaatcac ttctggttgg acctttggtg caggtgctgc 24241 attacaaata ccatttgcta tgcaaatggc ttataggttt aatggtattg gagttacaca 24301 gaatgttctc tatgagaacc aaaaattgat tgccaaccaa tttaatagtg ctattggcaa 24361 aattcaagac tcactttctt ccacagcaag tgcacttgga aaacttcaag atgtggtcaa 24421 ccaaaatgca caagctttaa acacgcttgt taaacaactt agctccaatt ttggtgcaat 24481 ttcaagtgtt ttaaatgata tcctttcacg tcttgacaaa gttgaggctg aagtgcaaat 24541 tgataggttg atcacaggca gacttcaaag tttgcagaca tatgtgactc aacaattaat 24601 tagagctgca gaaatcagag cttctgctaa tcttgctgct actaaaatgt cagagtgtgt 24661 acttggacaa tcaaaaagag ttgatttttg tggaaagggc tatcatctta tgtccttccc 24721 tcagtcagca cctcatggtg tagtcttctt gcatgtgact tatgtccctg cacaagaaaa 24781 gaacttcaca actgctcctg ccatttgtca tgatggaaaa gcacactttc ctcgtgaagg 24841 tgtctttgtt tcaaatggca cacactggtt tgtaacacaa aggaattttt atgaaccaca -continued

```
24901 aatcattact acagacaaca catttgtgtc tggtaactgt gatgttgtaa taggaattgt
24961 caacaacaca gtttatgatc ctttgcaacc tgaattagac tcattcaagg aggagttaga
25021 taaatatttt aagaatcata catcaccaga tgttgattta ggtgacatct ctggcattaa
25081 tgcttcagtt gtaaacattc aaaaagaaat tgaccgcctc aatgaggttg ccaagaattt
25141 aaatgaatct ctcatcgatc tccaagaact tggaaagtat gagcagtata taaaatggcc
25201 atggtacatt tggctaggtt ttatagctgg cttgattgcc atagtaatgg tgacaattat
25261 gctttgctgt atgaccagtt gctgtagttg tctcaagggc tgttgttctt gtggatcctg
25321 ctgcaaattt gatgaagacg actctgagcc agtgctcaaa ggagtcaaat tacattacac
25381 ataaacgaac ttatggattt gtttatgaga atcttcacaa ttggaactgt aactttgaag
25441 caaggtgaaa tcaaggatgc tactccttca gattttgttc gcgctactgc aacgataccg
25501 atacaagcct cactcccttt cggatggctt attgttggcg ttgcacttct tgctgttttt
25561 cagagcgctt ccaaaatcat aaccctcaaa aagagatggc aactagcact ctccaagggt
25621 gttcactttg tttgcaactt gctgttgttg tttgtaacag tttactcaca ccttttgctc
25681 gttgctgctg gccttgaagc cccttttctc tatctttatg ctttagtcta cttcttgcag
25741 agtataaact tgtaagaat aataatgagg ctttggcttt gctggaaatg ccgttccaaa
25801 aacccattac tttatgatgc caactatttt ctttgctggc atactaattg ttacgactat
25861 tgtatacctt acaatagtgt aacttcttca attgtcatta cttcaggtga tggcacaaca
25921 agtcctattt ctgaacatga ctaccagatt ggtggttata ctgaaaaatg ggaatctgga
25981 gtaaaagact gtgttgtatt acacagttac ttcacttcag actattacca gctgtactca
26041 actcaattga gtacagacac tggtgttgaa catgttacct tcttcatcta caataaaatt
26101 gttgatgagc ctgaagaaca tgtccaaatt cacacaatcg acggttcatc cggagttgtt
26161 aatccagtaa tggaaccaat ttatgatgaa ccgacgacga ctactagcgt gcctttgtaa
26221 gcacaagctg atgagtacga acttatgtac tcattcgttt cggaagagac aggtacgtta
26281 atagttaata gcgtacttct ttttcttgct ttcgtggtat tcttgctagt tacactagcc
26341 atccttactg cgcttcgatt gtgtgcgtac tgctgcaata ttgttaacgt gagtcttgta
26401 aaaccttctt tttacgttta ctctcgtgtt aaaaatctga attcttctag agttcctgat
26461 cttctggtct aaacgaacta aatattatat tagtttttct gtttggaact ttaattttag
26521 ccatggcaga ttccaacggt actattaccg ttgaagagct taaaaagctc cttgaacaat
26581 ggaacctagt aataggtttc ctattcctta catggatttg tcttctacaa tttgcctatg
26641 ccaacaggaa taggtttttg tatataatta agttaatttt cctctggctg ttatggccag
26701 taactttagc ttgttttgtg cttgctgctg tttacagaat aaattggatc accggtggaa
26761 ttgctatcgc aatggcttgt cttgtaggct tgatgtggct cagctacttc attgcttctt
26821 tcagactgtt tgcgcgtacg cgttccatgt ggtcattcaa tccagaaact aacattcttc
26881 tcaacgtgcc actccatggc actattctga ccagaccgct tctagaaagt gaactcgtaa
26941 tcggagctgt gatccttcgt ggacatcttc gtattgctgg acaccatcta ggacgctgtg
27001 acatcaagga cctgcctaaa gaaatcactg ttgctacatc acgaacgctt tcttattaca
27061 aattgggagc ttcgcagcgt gtagcaggtg actcaggttt tgctgcatac agtcgctaca
27121 ggattggcaa ctataaatta aacacagacc attccagtag cagtgacaat attgctttgc
27181 ttgtacagta agtgacaaca gatgtttcat ctcgttgact ttcaggttac tatagcagag
27241 atattactaa ttattatgag gacttttaaa gtttccattt ggaatcttga ttacatcata
27301 aacctcataa ttaaaaattt atctaagtca ctaactgaga ataaatattc tcaattagat
```

-continued 27361 gaagagcaac caatggagat tgattaaacg aacatgaaaa ttattctttt cttggcactg
27421 ataacactcg ctacttgtga gctttatcac taccaagagt gtgttagagg tacaacagta
27481 cttttaaaag aaccttgctc ttctggaaca tacgagggca attcaccatt tcatcctcta
27541 gctgataaca aatttgcact gacttgcttt agcactcaat ttgcttttgc ttgtcctgac
27601 ggcgtaaaac acgtctatca gttacgtgcc agatcagttt cacctaaact gttcatcaga
27661 caagaggaag ttcaagaact ttactctcca atttttctta ttgttgcggc aatagtgttt
27721 ataacacttt gcttcacact caaaagaaag acagaatgat tgaactttca ttaattgact
27781 tctatttgtg ctttttagcc tttctgctat tccttgtttt aattatgctt attatctttt
27841 ggttctcact tgaactgcaa gatcataatg aaacttgtca cgcctaaacg aacatgaaat
27901 ttcttgtttt cttaggaatc atcacaactg tagctgcatt tcaccaagaa tgtagtttac
27961 agtcatgtac tcaacatcaa ccatatgtag ttgatgaccc gtgtcctatt cacttctatt
28021 ctaaatggta tattagagta ggagctagaa aatcagcacc tttaattgaa ttgtgcgtgg
28081 atgaggctgg ttctaaatca cccattcagt acatcgatat cggtaattat acagtttcct
28141 gtttaccttt tacaattaat tgccaggaac ctaaattggg tagtcttgta gtgcgttgtt
28201 cgttctatga agacttttta gagtatcatg acgttcgtgt tgttttagat ttcatctaaa
28261 cgaacaaact aaaatgtctg ataatggacc ccaaaatcag cgaaatgcac cccgcattac
28321 gtttggtgga ccctcagatt caactggcag taaccagaat ggagaacgca gtggggcgcg
28381 atcaaaacaa cgtcggcccc aaggtttacc caataatact gcgtcttggt tcaccgctct
28441 cactcaacat ggcaaggaag accttaaatt ccctcgagga caaggcgttc caattaacac
28501 caatagcagt ccagatgacc aaattggcta ctaccgaaga gctaccagac gaattcgtgg
28561 tggtgacggt aaaatgaaag atctcagtcc aagatggtat ttctactacc taggaactgg
28621 gccagaagct ggacttccct atggtgctaa caaagacggc atcatatggg ttgcaactga
28681 gggagccttg aatacaccaa aagatcacat tggcacccgc aatcctgcta acaatgctgc
28741 aatcgtgcta caacttcctc aaggaacaac attgccaaaa ggcttctacg cagaagggag
28801 cagaggcggc agtcaagcct cttctcgttc ctcatcacgt agtcgcaaca gttcaagaaa
28861 ttcaactcca ggcagcagta ggggaacttc tcctgctaga atggctggca atggcggtga
28921 tgctgctctt gctttgctgc tgcttgacag attgaaccag cttgagagca aaatgtctgg
28981 taaaggccaa caacaacaag gccaaactgt cactaagaaa tctgctgctg aggcttctaa
29041 gaagcctcgg caaaaacgta ctgccactaa agcatacaat gtaacacaag ctttcggcag
29101 acgtggtcca gaacaaaccc aaggaaattt tggggaccag gaactaatca gacaaggaac
29161 tgattacaaa cattggccgc aaattgcaca atttgccccc agcgcttcag cgttcttcgg
29221 aatgtcgcgc attggcatgg aagtcacacc ttcgggaacg tggttgacct acacaggtgc
29281 catcaaattg gatgacaaag atccaaattt caaagatcaa gtcattttgc tgaataagca
29341 tattgacgca tacaaaacat tcccaccaac agagcctaaa aaggacaaaa agaagaaggc
29401 tgatgaaact caagccttac cgcagagaca gaagaaacag caaactgtga ctcttcttcc
29461 tgctgcagat ttggatgatt tctccaaaca attgcaacaa tccatgagca gtgctgactc
29521 aactcaggcc taaactcatg cagaccacac aaggcagatg ggctatataa acgttttcgc
29581 ttttccgttt acgatatata gtctactctt gtgcagaatg aattctcgta actacatagc
29641 acaagtagat gtagttaact ttaatctcac atagcaatct ttaatcagtg tgtaacatta
29701 gggaggactt gaaagagcca ccacattttc accgaggcca cgcggagtac gatcgagtgt -continued

```
29761 acagtgaaca atgctaggga gagctgccta tatggaagag ccctaatgtg taaaattaat

29821 tttagtagtg ctatccccat gtgattttaa tagcttctta ggagaatgac aaaaaaaaaa

29881 aaaaaaaaaa aaaaaaaaaa aaa.
```

In some embodiments, the plurality of primers for the RPA assay are designed against a plurality of target regions in the nucleic acid sequence of SEQ ID NO:1, or variants thereof, such SARS-CoV-2 B.1.1.7 variant III. Methods of Diagnosis and/or Treatment Methods for detecting or diagnosing a viral infection in a subject are also provided. The methods provide rapid, fast and accurate results on the presence of a viral nucleic acid (e.g., SARS-CoV-2) in a sample. Typically, the method of diagnosing involves any of the methods for detecting a viral nucleic acid discussed above. For example, a method of diagnosing a subject for infection with a virus can include detecting the presence of a viral nucleic acid in a sample from the subject by performance of an RPA assay, optionally followed by sequencing of one or more amplification products. In some embodiments, detection of a plurality of amplification products indicates the subjects is infected with the virus. The detection may be qualitative or quantitative.

In a particular embodiment, the current or present exposure or infection with SARS-CoV-2 can be detected and/or diagnosed and/or treated using the disclosed compositions and methods. Typically, the presence and/or elevated amount of SARS-CoV-2 nucleic acid in a subject's biological sample as compared to a control (as determined by any disclosed method of detection for example) is indicative of current or past exposure or an active infection with SARS-CoV-2.

The subject may or may not exhibit symptoms of a disease, disorder, or condition associated with the virus. For example, a symptomatic subject may be suspected of having a particular viral infection. In such cases, the method of diagnosis can be used to confirm the etiology of the infection by detecting the presence of a particular viral nucleic acid in a sample from the subject. In some embodiments, the subject is asymptomatic, but can be suspected of having contact with a virus. In such cases, the method of diagnosis can be used to confirm exposure and/or infection with the virus.

The methods can be used to diagnose a viral infection at early stages. The early stages include asymptomatic or presymptomatic stages of infection, as well as days 0, 1, and 2 post symptom onset. In some embodiments, the methods have accuracy of greater than 90% specificity and greater than 90% sensitivity for detecting a viral infection (e.g., SARS-CoV-2) in the subject prior to onset of symptoms of infection, on the day of onset of symptoms of infection, or one day, two days, three days, four days, five days, six days, or seven days after onset of symptoms of infection.

Exemplary viruses and symptoms of illness stemming from infection by the viruses that are treatable by the disclosed methods are also provided. The virus is typically a coronavirus. Coronaviruses cause diseases in mammals and birds. In humans, coronaviruses can cause respiratory tract infections that can range from mild to lethal. Mild illnesses include some cases of the common cold, while more lethal varieties can cause SARS, MERS, and COVID-19 (i.e., caused by SARS-CoV-2).

Thus, in some embodiments, the subject may have one or more symptoms characteristic of SARS, MERS, or COVID-19. SARS (i.e., SAR-CoV) usually begins with flu-like signs and symptoms such as fever, chills, muscle aches, headache and occasionally diarrhea. After about a week, signs and symptoms include fever of 100.5 F (38 C) or higher, dry cough, shortness of breath, headache, muscular stiffness, loss of appetite, malaise, confusion, rash, or diarrhea, or any combination thereof.

Reported illnesses from COVID-19 (i.e., caused by SARS-CoV-2) have ranged from mild symptoms to severe illness and death for confirmed cases. The most common symptoms are fever, tiredness, dry cough, loss of taste or smell, sore throat, runny nose, congestion, vomiting, diarrhea and shortness of breath. These symptoms may appear 2-14 days after exposure. Symptoms differ with severity of disease. For example, fever, cough, and shortness of breath are more commonly reported among people who are hospitalized with COVID-19 than among those with milder disease (non-hospitalized patients). Atypical presentations occur often, and older adults and persons with medical comorbidities may have delayed presentation of fever and respiratory symptoms. In one study of 1,099 hospitalized patients, fever was present in only 44% at hospital admission but eventually developed in 89% during hospitalization. Fatigue, headache, and muscle aches (myalgia) are among the most commonly reported symptoms in people who are not hospitalized, and sore throat and nasal congestion or runny nose (rhinorrhea) also may be prominent symptoms. Many people with COVID-19 experience gastrointestinal symptoms such as nausea, vomiting or diarrhea, sometimes prior to developing fever and lower respiratory tract signs and symptoms. Loss of smell (anosmia) or taste (ageusia) preceding the onset of respiratory symptoms has been commonly reported in COVID-19 especially among women and young or middle-aged patients who do not require hospitalization. While many of the symptoms of COVID-19 are common to other respiratory or viral illnesses, anosmia appears to be more specific to COVID-19. In critical cases, respiratory failure, shock, or multiorgan system dysfunction is common.

Most people confirmed to have MERS-CoV infection have had severe respiratory illness with symptoms of fever, cough, and/or shortness of breath. Some people also exhibit diarrhea and nausea/vomiting. For many people with MERS, more severe complications followed, such as pneumonia and kidney failure. Some infected people had mild symptoms (such as cold-like symptoms) or no symptoms at all.

In some embodiments, the subject has an underlying condition such as asthma, heart disease, diabetes, cancer, chronic lung disease, chronic heart disease, chronic kidney disease, an autoimmune disease, or a combination thereof. Preferably, the subject is human.

Any of the disclosed methods can be combined with a method of treatment. In some embodiments, upon diagnosis as infected with the virus, the subject is further treated. In preferred embodiments, the method of treatment includes administering the subject an effective amount of an anti-viral therapy (e.g., remdesivir), analgesic therapy (e.g., ibuprofen, acetaminophen), corticosteroid therapy (e.g., dexamethasone, prednisone, methylprednisolone, or hydrocortisone), fever reducers, cough suppressants, and/or respiratory assistance (e.g., supplemental oxygen or mechanical ventilation).

IV. Kits

Also disclosed are kits for carrying out the disclosed methods. Compositions, reagents, and other materials can be packaged together in any suitable combination as a kit useful for performing, or aiding in the performance of, the disclosed methods. It is useful if the kit components in a given kit are designed and adapted for use together in the disclosed methods. For example, disclosed are kits with one or more primers, buffers, and/or enzymes. The kits may include a sterile needle, swab, syringe, ampule, tube, container, or other suitable vessels for isolating samples, holding assay components and/or performing the assay. The kits may include instructions for use.

The kit can include a sufficient quantity of reverse transcriptase, a DNA polymerase, single-stranded DNA binding proteins (SSBs), recombinases suitable nucleoside triphosphates, primers (e.g., 2 or more primer pairs), and/or reaction buffer, or any combination thereof, for the amplification processes described above. A kit may further include instructions pertinent for the particular embodiment of the kit, such as providing conditions and steps for operation of the method. A kit may also contain reaction containers such as microcentrifuge tubes and the like. A kit may also reagents for isolating a biological sample and extracting nucleic acids therefrom.

The kits may contain nucleic acid primers suspended in an aqueous solution or as a freeze-dried or lyophilized powder, for instance. The container(s) in which the primers are supplied can be any conventional container that is capable of holding the supplied form, for instance, microfuge tubes, multi-well plates, ampoules, or bottles. One or more control probes, primers, and or nucleic acids also may be supplied in the kit. For example, the kit may include one or more positive control samples (such as a sample including a particular viral nucleic acid) and/or one or more negative control samples (such as a sample known to be negative for a particular viral nucleic acid).

In some embodiments, one or more primers (such as one or more sets of primers suitable for SARS-Cov-2), may be provided in pre-measured single use amounts in individual, typically disposable, tubes, wells, or equivalent containers. In this embodiment, the sample to be tested for the presence of the target nucleic acids can be added to the individual tube(s) or well(s) and amplification and/or detection can be carried out directly. In some examples, the containers may also contain additional reagents for amplification reactions, such as buffer, enzymes (such as reverse transcriptase and/or DNA polymerase), dNTPs, or other reagents. In some embodiments, the container includes all of the components required for the reaction except the sample (and water, if the reagents are supplied in dried or lyophilized form).

In some embodiments, the kit can contain reagents and instructions for detecting a viral nucleic acid. This can include for example, reagents, instructions, software and/or hardware for gel electrophoresis, sequencing library preparation, sequencing, and data analysis.

The disclosed compositions and methods can be further understood through the following numbered paragraphs.

1. A method for determining the presence of a viral nucleic acid in a sample comprising:

contacting the sample with a plurality of primers specific to the nucleic acid;

performing a single reaction to simultaneously amplify a plurality of target regions in multiple viral nucleic acid; and detecting the amplification products, thereby determining the presence of the viral nucleic acid in the sample.

2. The method of paragraph 1, wherein the nucleic acid is derived from viruses, preferably a Severe acute respiratory syndrome-related coronavirus, influenza A, human adenovirus, and non-SARS-CoV-2 human coronavirus.

3. The method of paragraph 2, wherein the Severe acute respiratory syndrome-related coronavirus is SARS-CoV or SARS-CoV-2.

4. The method of any one of paragraphs 1-3, wherein the plurality of primers comprises 7-9 pairs of primers and/or wherein the plurality of target regions comprises 7-9 target regions.

5. The method of paragraph 4 comprising 9 pairs of primers.

6. The method of paragraph 4 or 5 comprising 9 target regions.

7. The method of paragraph 6, wherein one or more of the target regions comprise genomic regions comprising signature mutations or mutation hotspots.

8. The method of paragraph 6 or 7, wherein one or more of the target regions are within the N gene, S gene, ORF1ab, or ORF8.

9. The method of any one of paragraphs 5-8, wherein one or more of the primers comprise a nucleic acid sequence having at least 90% sequence identity to any one of SEQ ID NOs:2-11.

10. The method of any one of paragraphs 1-9, wherein the amplification reaction comprises an isothermal recombinase polymerase amplification (RPA).

11. The method of any one of paragraphs 1-10 further comprising characterizing the viral nucleic acid by a method comprising sequencing the amplification products and analyzing the sequences.

12. The method of paragraph 11, wherein the sequencing is performed using a Nanopore MinION.

13. The method of paragraph 11 or 12, wherein the analysis comprises aligning the sequences to a reference viral genome and determining the presence of one or more genetic variants in the sequences as compared to the reference.

14. The method of paragraph 13, wherein the variants comprise single nucleotide variants, multiple nucleotide variants, indels, deletions or insertions larger than 50 bp, duplications or inversions.

15. The method of any one of paragraphs 11-14, wherein the analysis is performed in real-time or near real-time.

16. The method of any one of paragraphs 1-15 performed on about 10-100 samples simultaneously.

17. The method of any one of paragraphs 1-16, wherein the method has a duration of about 0.5-4 hours.

18. A method for detecting the presence of a viral nucleic acid in a sample and one or more mutations therein, the method comprising: (a) performing an isothermal recombinase polymerase amplification (RPA) on the sample to simultaneously amplify a plurality of target regions in multiple viral nucleic acid, thereby generating a plurality of amplification products;

(b) sequencing the amplification products;

(c) aligning the sequences to a reference viral genome or sequence, wherein existence of reads covering targeted amplicons indicates presence of the viral nucleic acid; and (d) determining the presence of one or more mutations in the sequences as compared to the reference.

19. A method of diagnosing a subject for infection with a virus comprising detecting the presence of a viral nucleic acid in a sample from the subject by the method of any one of paragraphs 1-10, wherein detecting the amplification products indicates the subjects is infected with the virus.

20. The method of paragraph 19, wherein the subject exhibits or does not exhibit symptoms of a disease, disorder, or condition associated with the virus.

21. The method of paragraph 19 further comprising treating the subject, wherein the subject was diagnosed as infected with the virus.

22. The method of paragraphs 19-21, wherein the subject is human.

23. The method of any one of paragraphs 1-22, wherein the sample is a nucleic acid sample.

24. The method of paragraph 24, wherein the nucleic acid sample is derived from mucus, sputum (processed or unprocessed), bronchial alveolar lavage (BAL), bronchial wash (BW), cerebrospinal fluid (CSF), urine, tissue (e.g., biopsy material), rectal swab, nasopharyngeal aspirate, nasopharyngeal swab, throat swab, saliva, feces, mucosal excretions, plasma, serum, or whole blood.

EXAMPLES

Example 1: Development of NIRVANA—a Multiplex Method for the Rapid Detection and Mutational Surveillance of SARS-Cov-2

Methods

RNA Samples and Primers

Anonymized RNA samples were obtained from Ministry of Health (MOH) hospitals in the western region in Saudi Arabia. The use of clinical samples in this study was approved by the institutional review board (IRB #H-02-K-076-0320-279) of MOH and KAUST Institutional Biosafety and Bioethics Committee (IBEC). Oropharyngeal and nasopharyngeal swabs were carried out by physicians and samples were steeped in 1 mL of TRIzol (Invitrogen Cat. No 15596018) to inactivate virus during transportation. Total RNA extraction of the samples was performed following instructions as described in the CDC EUA-approved protocol using the Direct-Zol RNA Miniprep kit (Zymo Research Cat. No R2070) or TRIzol reagent (Invitrogen Cat. No 15596026) following the manufacturers' instructions. The Respiratory (21 targets) control panel (Microbiologics Cat. No 8217) was used as positive control in the amplification of FluA, HAdVs and HCoV. A full list of primers used in this study can be found in Table 1.

TABLE 1

Primers used in this study

| Primer | Sequence | |
|---|---|---|
| pair4-F | GCTGGTTCTAAATCACCCATTCAGT | (SEQ ID NO: 2) |
| pair4-R | TCTGGTTACTGCCAGTTGAATCTG | (SEQ ID NO: 3) |
| pair5-F | TTGGGATCAGACATACCACCCA | (SEQ ID NO: 4) |
| pair5-R | CAACACCTAGCTCTCTGAAGTGG | (SEQ ID NO: 5) |
| pair9-F | CCAGCAACTGTTTGTGGACCT | (SEQ ID NO: 6) |
| pair9-R | AGCAACAGGGACTTCTGTGC | (SEQ ID NO: 7) |
| pair10-F | GACCCCAAAATCAGCGAAAT | (SEQ ID NO: 8) |
| pair10-R | TGTAGCACGATTGCAGCATTG | (SEQ ID NO: 9) |
| pair13-F | CCAGAGTACTCAATGGTCTTTGTTC | (SEQ ID NO: 10) |
| pair13-R | ACCCAACTAGCAGGCATATAGAC | (SEQ ID NO: 11) |
| ACTB-F | CCCAGCCATGTACGTTGCTATCCAGGC | (SEQ ID NO: 12) |
| ACTB-R | ACAGCTTCTCCTTAATGTCACGCACGAT | (SEQ ID NO: 13) |
| FluA-F | ATGAGYCTTYTAACCGAGGTCGAAACG | (SEQ ID NO: 14) |
| FluA-R | TGGACAAANCGTCTACGCTGCAG | (SEQ ID NO: 15) |
| HAdV-F | GCCGAGAAGGGCGTGCGCAGGTA | (SEQ ID NO: 16) |
| HAdV-R | TACGCCAACTCCGCCCACGCGCT | (SEQ ID NO: 17) |
| HCoV-F | ATGGTCAAGGAGTTCCCATTGCTTTCGG AGTA | (SEQ ID NO: 18) |
| HCoV-R | GGGCCGGTACCGAGATAGTAGAAATAC CATCTCG | (SEQ ID NO: 19) |

The PMMoV primers used in wastewater samples were PMMoV-F:

```
                                   (SEQ ID NO: 21)
TCAAATGAGAGTGGTTTGACCTTAACGTTTGA
and

PMMoV-R:
                                   (SEQ ID NO: 20)
AACTCATCGGACACTGTGTTGCCTGTTAGAC.
```

Wastewater Samples

Raw sewage was collected at 9 AM and 4 PM on 7 Jun. 2020 from the wastewater equalization tank in KAUST, and then mixed together to constitute a composite sample. A 300-500 ml of sewage mixture was concentrated by electronegative membrane in the present of cation as previously described (Haramoto et al., 2004). The eluate of viruses were recovered in a tube with 50 μL of 100 mM $H_2SO_4$ (pH 1.0) and 100 μL of 100× Tris-EDTA buffer (pH 8.0) for neutralization. Centripep YM-50 (Merck Millipore) was used to further concentrate the samples to a volume of 600-700 μl.

Reverse Transcription

Reverse transcription of RNA samples was done using either NEB ProtoScript II reverse transcriptase (NEB Cat. No M0368) or Invitrogen SuperScript IV reverse transcriptase (Thermo Fisher Scientific Cat. No 18090010), following protocols provided by the manufacturers. After reverse transcription, 5 units of thermostable RNase H (New England Biolabs Cat. No M0523S) was added to the reaction, which was incubated at 37° C. for 20 min to remove RNA. The final reaction was diluted to be used as templates in RPA. All of the web-lab experiments in this study were conducted in a horizontal flow clean bench to prevent contaminations. The bench was decontaminated with 70% ethanol, DNAZap (Invitrogen, Cat no. AM9890) and RNase AWAY (Invitrogen, Cat no. 10328011) before and after use. The filtered pipette tips (Eppendorf epT.IP.S.® LoRetention series) and centrifuge tubes (Eppendorf DNA LoBind Tubes, Cat. No 0030108051) used in this study were PCR-clean grade. All of the operations were performed carefully following standard laboratory operating procedures.

rRT-PCR

The rRT-PCR assay of SARS-CoV-2 was purchased from IDT (Cat. No 10006770). The rRT-PCR assay for FluA was purchased from IDT (Cat. No 1079729). Respiratory Virus PCR Panel kit (Diagenode diagnostics, DDGR-90-L048) was used for the determination of FluA, HAdVs and HCoV. All reactions were run on a CFX384 Touch Real-Time PCR Detection System (Bio-rad) following the instruction of manufacturers. The copy number of SARS-CoV-2 was determined by the IDT SARS-CoV-2 rRT-PCR assay based on the standard curve of CT values of known copies of synthetic SARS-CoV-2 N gene RNA (nt28,287-29,230 in NC_045512.2, DNA template purchased from IDT). A serial dilution of the synthetic RNA was performed to obtain final concentrations of 10, $10^2$, $10^3$, $10^4$, $10^5$, $10^6$, $10^7$ copies/μl. The reverse transcription was done using 1 μl of diluted RNA, followed by rRT-PCR using 2.5 μl of 5-fold diluted cDNA.

Singleplex RPA

Singleplex RPA was performed using TwistAmp® Basic kit following the standard protocol. Thirteen pairs of SARS-CoV-2 primers covering N gene, S gene, ORFlab and ORF8 were tested and the corresponding amplicons were purified by 0.8× Beckman Coulter AMPure XP beads (Cat. No A63882) and eluted in 40 μl $H_2O$. The purified amplicons were first analyzed by running DNA agarose gel to check the specificity and efficiency. The most robust five pairs of primers with correct size were further analyzed by NlaIII (NEB Cat. No R0125L) and SpeI (NEB Cat. No R0133L) digestion following standard protocols. For one-pot RT-RPA, 10 U of AMV Reverse Transcriptase (NEB Cat no. M0277S) and 20 U of SUPERase•In™ RNase Inhibitor (Invitrogen Cat no. AM2694) were added to a regular RPA reaction mix. The RT-RPA was carried out per the manufacturer protocol. For the RPA of respiratory viruses, reverse-transcribed cDNA from the Respiratory (21 targets) control panel (Microbiologics Cat. No 8217) was used as the template.

Multiplex RPA

Multiplex RPA was done by add all of the primers in the same reaction. The total final primer concentration was set to 2 μM. To achieve an even and robust amplification, we empirically determined the final concentration of the five-amplicon primers (for the initial test of 10 SARS-CoV-2 positive samples) as follows: 0.166 μM for each pair-4 primer, 0.166 μM for each pair-5 primer, 0.242 μM for each pair-9 primer, 0.26 μM for each pair-10 primer, 0.166 μM for each pair-13 primer, 29.5 μl of primer free rehydration buffer, 1 μl of 10-fold diluted cDNA, 7 μl $H_2O$. In the multiplex RPA of 9-amplicon and 7-amplicon (remove pairs 9 & 10) primers, the primer mixtures were obtained by combining different amount of 10 μM primers according to the ratios in Table 1, and 2.5 μl of 5-fold diluted cDNA were used as template. The FluA and HAdV primers target regions that are expected to be shared by all subtypes of the corresponding viruses, while the HCoV primers are specific for the HKU1 subtype. The reaction was incubated at 39° C. for 4 min, then vortexed and spin down briefly, followed by a 16-min incubation at 39° C.

Library Preparation and Sequencing

The RPA library preparation was done using Native barcoding expansion kit (Oxford Nanopore Technologies EXP-NBD 114 and EXP-NBD196) following Nanopore PCR tiling of COVID-19 Virus protocol (Ver: PTC_9096_v109_revE_06Feb2020) with a few changes to save time. The RPA reaction was purified using Qiagen QIAquick PCR purification kit (Qiagen Cat No. 28106) and elute in 30 μl $H_2O$. The end-prep reaction was done separately in 15 μl volume using 5 μl of each multiplex RPA samples. After that, the same procedures as described in the official protocol was followed. The RT-PCR library preparation was done using Native barcoding expansion kit (Oxford Nanopore Technologies EXP-NBD104) according to the standard native barcoding amplicons protocol. The sequencing runs were performed on an Oxford Nanopore MinION sequencer using R9.4.1 flow cells.

Quantification and Statistical Analysis

RTNano scanned the sequencing folder repeatedly based on user defined interval time. Once newly generated fastq files were detected, it moved the files to the analysis folder and made a new folder for each sample. If the Nanopore demultiplexing tool guppy is provided, RTNano will do additional demultiplexing to make sure reads are correctly classified. The analysis part utilized minimap2 (Li, 2018) to quickly align the reads to the SARS-CoV-2 reference genome (GenBank: NC_045512). After alignment, RTNano will filter the alignment records based on defined thresholds of parentage identity and amplicon coverage, followed by counting the alignment records of each amplicon. A read with >=89% alignment identity and >=96% amplicon coverage will be counted as one positive record. If an NTC barcode number was provided, RTNano will subtract this number in individual sample analysis to further ensure confident demultiplexing. In the end, RTNano will assign samples with different result marks (POS, NEG and UNK) based on the number of alignment records of each amplicon. With the sequencing continuing, RTNano will merge the newly analyzed result with completed ones to update the current sequencing statistics. RTNano is ultra-fast, a typical analysis with additional guppy demultiplexing of 5 fastq files (containing 4000 reads each and sequenced with 12-barcode kit) will take ~10 s using one thread in a MacBook Pro 2016 15-inch laptop. Variant calling was performed using samtools (v1.9) and bcftools (v1.9)(Li et al., 2009). The detected variants were filtered by position (within the targeted regions) and compared with the data in Nextstrain.org as of Jun. 2, 2020.

Results

Figure 1B:
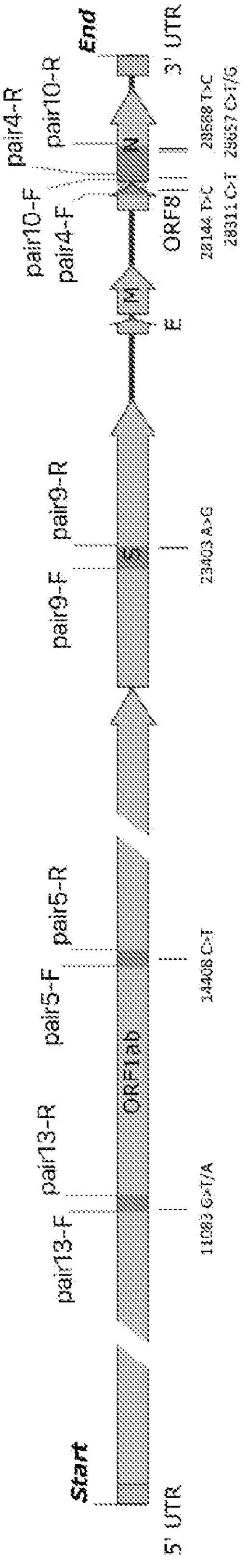
Figure 1C:
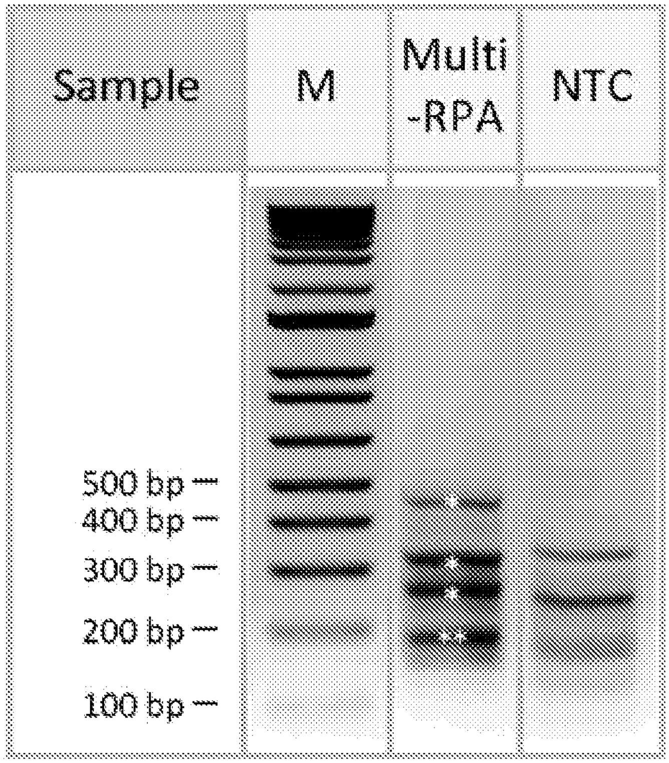
Figure 2A:
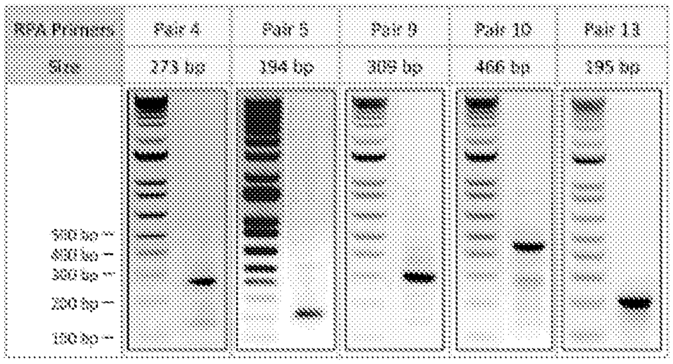
FIGS. 2A-D show agarose gel electrophoresis results of singleplex RPA.
Figure 2B:
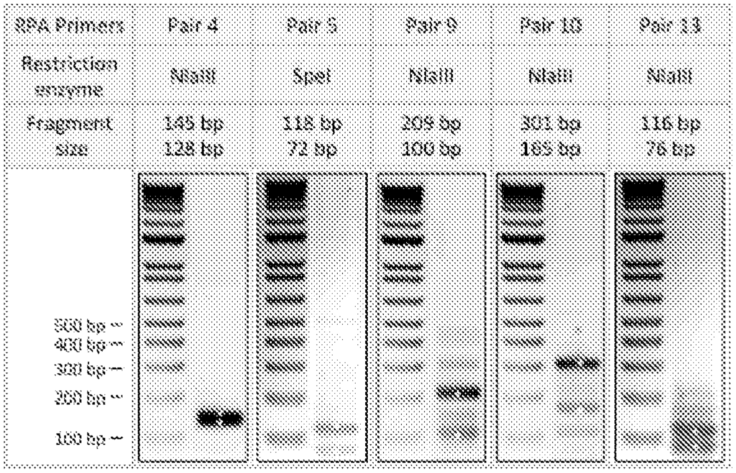
Figure 2C:
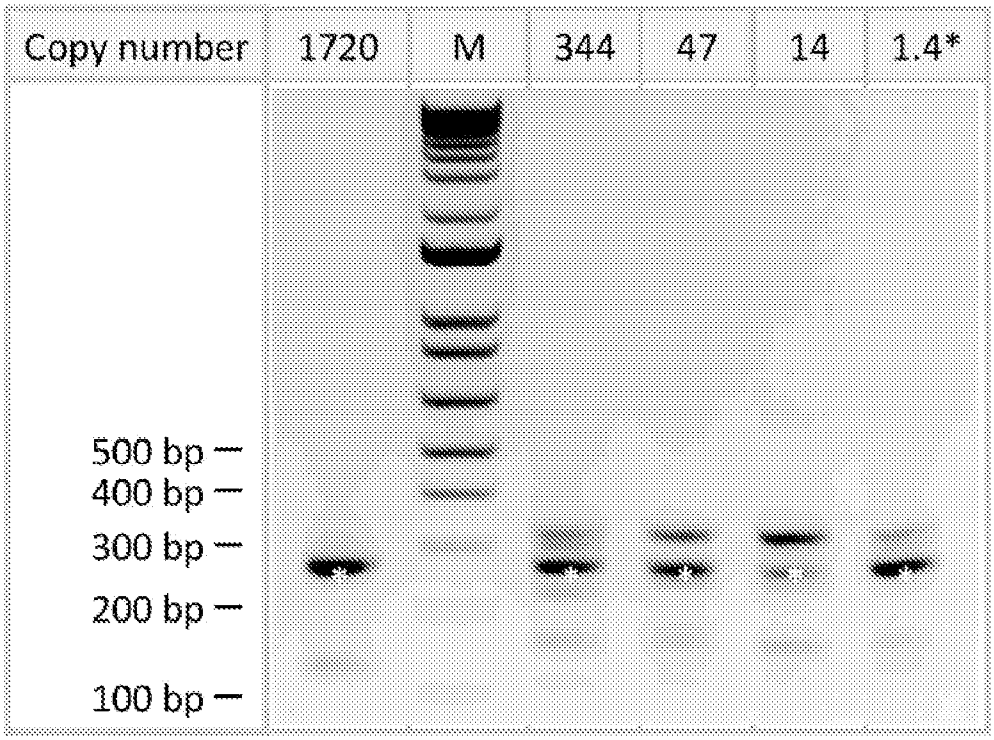

Singleplex RPA was first performed to test its ability to amplify the SARS-CoV-2 genome from a nasopharyngeal swab sample tested positive for the virus using the US CDC assays[5] (CT value=21). Sixteen primers were tested in 12 combinations to amplify 5 regions harboring either reported signature mutations[21,22] useful for strain classification or mutation hotspots (GISAID, as of Mar. 15, 2020). Five pairs of primers showed robust amplification of DNA of predicted size (range: 194-466 bp) in a 20-min isothermal reaction at 39° C. (FIG. 1B, FIG. 2A). The specificity of all 5 RPA products was verified by restriction enzyme digestion (FIG. 2B). The limit of detection of RPA reaches below 10 copies per reaction (FIG. 2C). Furthermore, the data showed that these RPA reactions could be multiplexed to amplify the five regions of the SARS-CoV-2 genome in a single reaction (FIG. 1C), thus significantly simplifying the workflow.

Figure 1D:
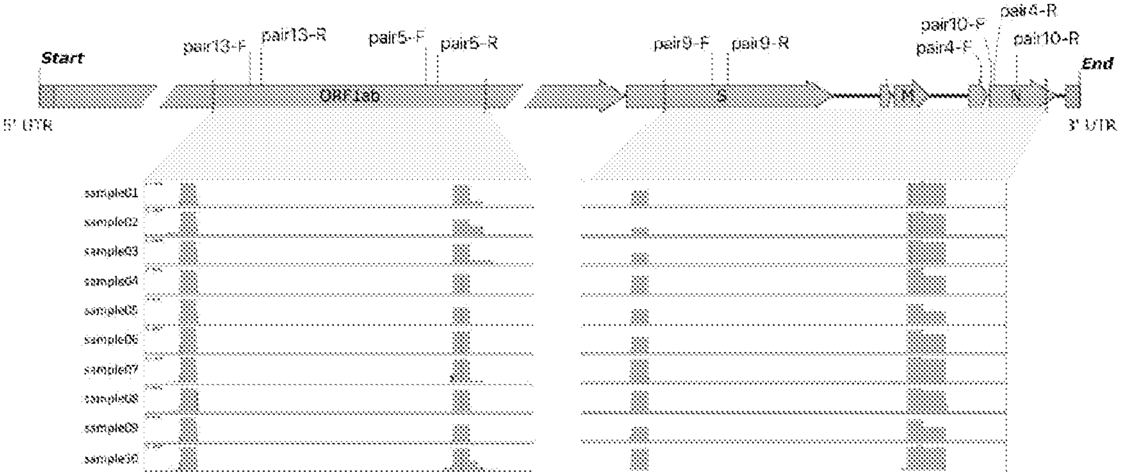
Figures 4A, 4B:
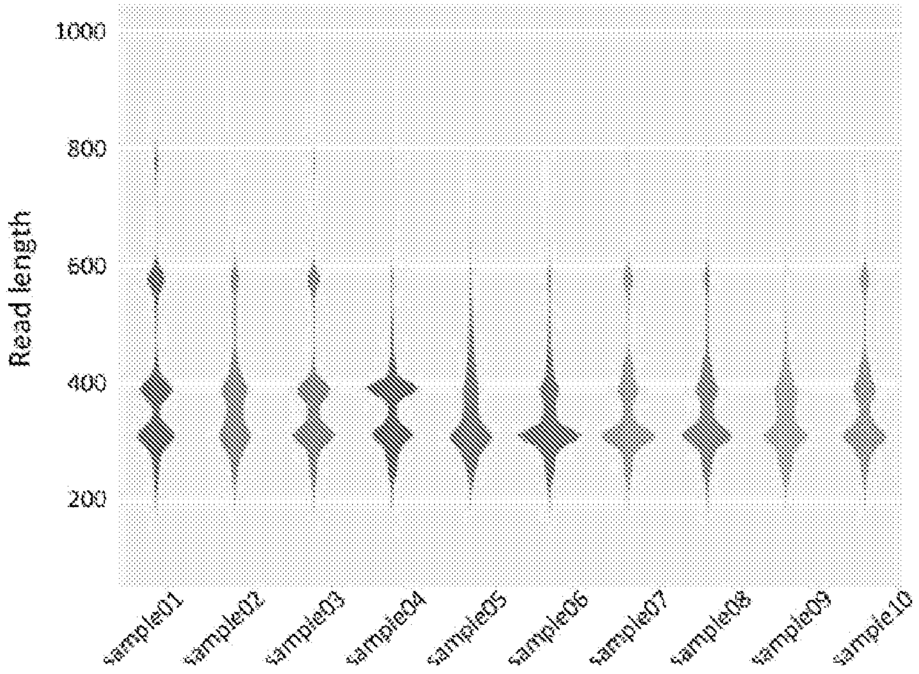
FIG. 4A-G show sequencing analysis of multiplex RPA.

Next, multiplex RPA was performed using ten SARS-CoV-2 positive samples (SARS-CoV-2*, determined by US CDC assays[5], CT value range: 15 to 27.9). Multiplex RPA products of the 10 samples were individually barcoded, pooled and prepared into a Nanopore sequencing library using an optimized protocol as disclosed in the methods section under “Examples”). The whole workflow from RNA to sequencing took approximately 4 hours (FIG. 1A). The barcoded library was sequenced on a Nanopore MinION using a R9.4.1 flow cell. After 12-h sequencing, resulting in a total of 1.7 million reads from this barcoded library (FIG. 4A). The demultiplexed reads were distributed relatively evenly among the barcodes (samples). The reads were aligned to the SARS-CoV-2 reference genome. This alignment showed that all RPA amplicons were covered by thousands of reads in all samples, suggesting that barcoded multiplexed RPA sequencing worked effectively (FIG. 1D, FIG. 4B).

Figure 4C:
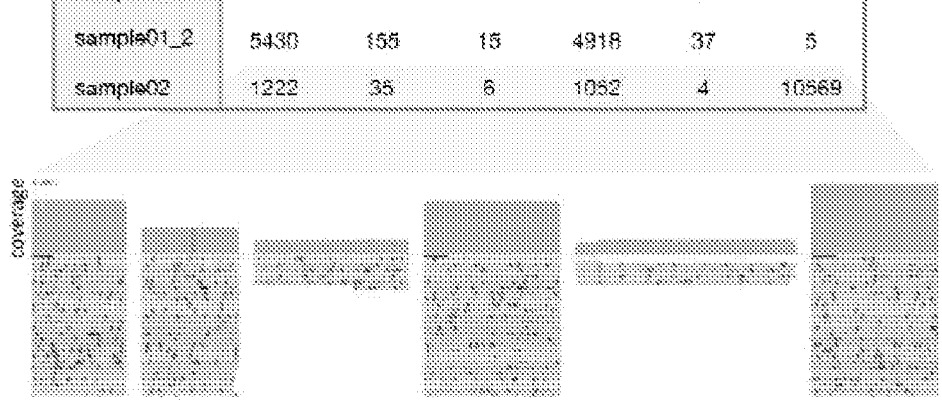

The identification of a SARS-CoV-2 positive sample can be achieved by surveying the existence of targeted amplicons via sequencing. However, the determination of negative samples needs to rule out potential sample collection failure, thus requiring a sample quality validation control. The existence of transcripts of the human housekeeping gene ACTB was used as a quality check of sample collection. The sequencing results showed that the ACTB gene could be effectively amplified without significantly affecting the amplification of SARS-CoV-2 (FIG. 4C).

Co-infection with other respiratory pathogens in COVID-19 patients has been evaluated, though current detection of co-infections requires additional rRT-PCR assays (Hashemi et al., 2020; Kim et al., 2020; Ma et al., 2020) or NGS (Babiker et al., 2020). Such ad hoc tests are not amenable to large-scale screening of co-infections. On the other hand, multiplexed RPA of different viruses could be a promising solution to detect co-infections in a timely and efficient manner.

As a proof-of-principle of multiplex RPA of multiple human viral pathogens, RPA primers that robustly amplify influenza A (FluA), human adenovirus (HAdV), and non-SARS-CoV-2 human coronavirus (HCoV), respectively, were screened and validated (data not shown). The three pairs of respiratory virus primers were added to the multiplex SARS-CoV-2 RPA panel to achieve simultaneous isothermal amplification of four viral pathogens (table 1).

TABLE 1

Primers used in this study

| Primer | Sequence | | Amplicon Size | Primer Amount |
|---|---|---|---|---|
| pair4-F | GCTGGTTCTAAATCACCCATTCAGT | (SEQ ID NO: 2) | 273 bp | 6 µl |
| pair4-R | TCTGGTTACTGCCAGTTGAATCTG | (SEQ ID NO: 3) | | |
| pair5-F | TTGGGATCAGACATACCACCCA | (SEQ ID NO: 4) | 194 bp | 9 µl |
| pair5-R | CAACACCTAGCTCTCTGAAGTGG | (SEQ ID NO: 5) | | |
| pair9-F | CCAGCAACTGTTTGTGGACCT | (SEQ ID NO: 6) | 309 bp | 12 µl |
| pair9-R | AGCAACAGGGACTTCTGTGC | (SEQ ID NO: 7) | | |
| pair10-F | GACCCCAAAATCAGCGAAAT | (SEQ ID NO: 8) | 394 bp | 12 µl |
| pair10-R | TGTAGCACGATTGCAGCATTG | (SEQ ID NO: 9) | | |
| pair13-F | CCAGAGTACTCAATGGTCTTTGTTC | (SEQ ID NO: 10) | 195 bp | 6 µl |
| pair13-R | ACCCAACTAGCAGGCATATAGAC | (SEQ ID NO: 11) | | |
| ACTB-F | CCCAGCCATGTACGTTGCTATCCAGGC | (SEQ ID NO: 12) | 263 bp | 4 µl |
| ACTB-R | ACAGCTTCTCCTTAATGTCACGCACGAT | (SEQ ID NO: 13) | | |
| influA-F | ATGAGYCTTYTAACCGAGGTCGAAACG | (SEQ ID NO: 14) | 244 bp | 12 µl |
| influA-R | TGGACAAANCGTCTACGCTGCAG | (SEQ ID NO: 15) | | |

TABLE 1-continued

| Primers used in this study | | | | |
|---|---|---|---|---|
| Primer | Sequence | | Amplicon Size | Primer Amount |
| HAdV-F | GCCGAGAAGGGCGTGCGCAGGTA | (SEQ ID NO: 16) | 161 bp | 9 µl |
| HAdV-R | TACGCCAACTCCGCCCACGCGCT | (SEQ ID NO: 17) | | |
| HCoV-F | ATGGTCAAGGAGTTCCCATTGCTTTC GGAGTA | (SEQ ID NO: 18) | 151 bp | 9 µl |
| HCoV-R | GGGCCGGTACCGAGATAGTAGAAAT ACCATCTCG | (SEQ ID NO: 19) | | |

Figure 3A:
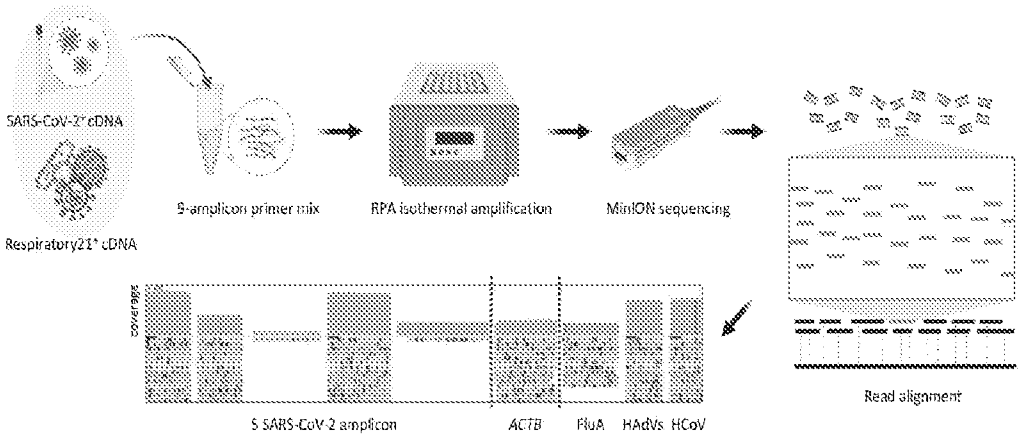
FIG. 3A-F show real-time detection of multiple viral pathogens and mutational analysis of SARS-CoV-2.

To ensure effective amplification of all targets, the concentration of each primer pair was adjusted based on the read depth of the cognate genomic region when sequencing a contrived co-infection sample made from a SARS-CoV-2$^+$ sample spiked with a control panel of 21 respiratory viruses including FluA, HAdV, and HCoV (Respiratory21$^+$). The final primer mix achieved amplification of all targeted amplicons (FIG. 3A).

Figure 4D:
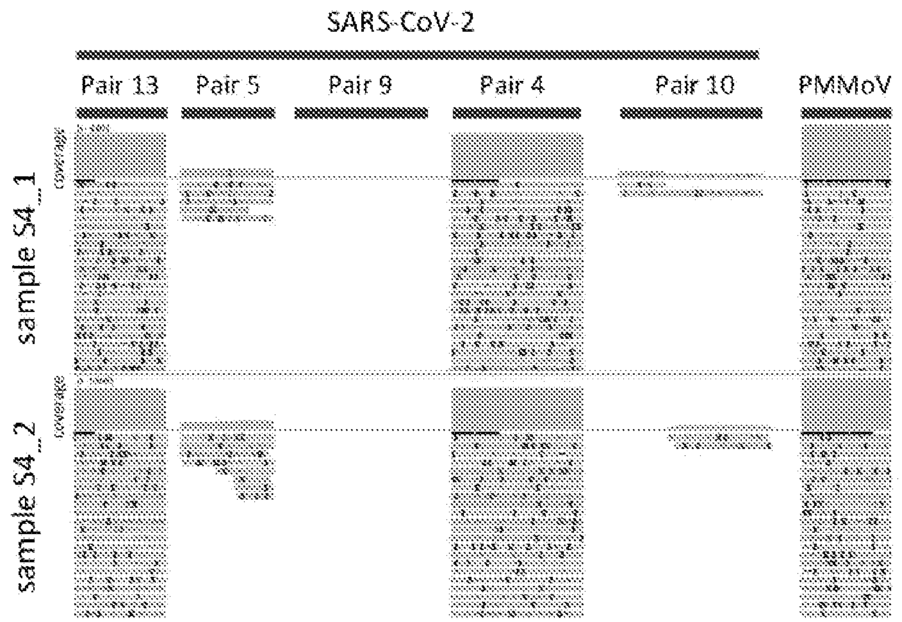

The presence of SARS-CoV-2 has been reported in municipal sewage, with the viral load was found to be correlated to the reported COVID-19 prevalence[25]. This suggests that wastewater surveillance could be a sensitive indicator of total COVID-19 case load (including asymptomatic cases) in the population. To evaluate the possibility of using multiplex RPA to detect SARS-CoV-2 in wastewater, the primer mix to simultaneously amplify five regions of SARS-CoV-2 and one region of pepper mild mottle virus (PMMoV, an omnipresent indicator of water quality[26]) was determined. The wastewater concentrate (as disclosed in the methods section under “Examples”)) was spiked with RNA of SARS-CoV-2 positive samples, and used this as a positive control to test the multiplex RPA. Two primer mixes with different concentration of PMMoV primers were tested. Both primer mixtures can detect the SARS-CoV-2 and PMMoV within the positive control (FIG. 4D). These results suggested that multiplex RPA could be used to monitor the presence of SARS-CoV-2 and other viruses in municipal wastewater. In addition, because the simultaneous acquisition of viral sequences, this method can also survey the strains circulating in the population (see below).

Figure 1E:
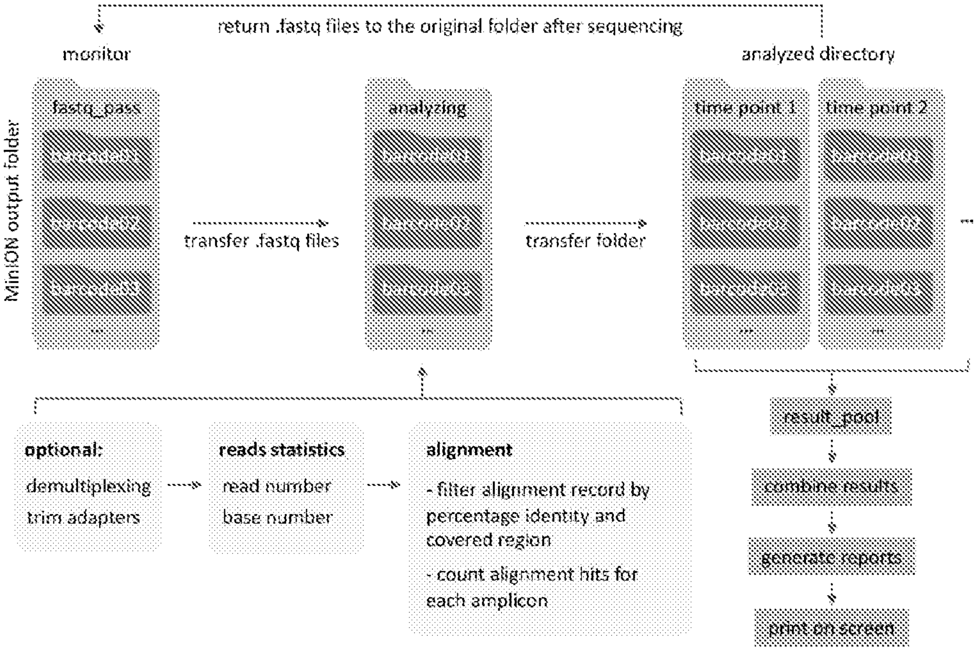

Multi-virus multiplex RPA assay was performed next, followed by Nanopore sequencing in 60 clinical samples suspected of SARS-CoV-2 infection. Following RT and RPA (FIG. 1A), amplicons of each sample were barcoded and sequenced in one Nanopore MinION flow cell. To take advantage of the unique feature of real-time base-calling offered by Nanopore sequencing, a bioinformatics algorithm termed Real-Time Nanopore sequencing monitor (RTNano) was developed (FIG. 1E). RTNano continuously monitors the output folder of base called data during the sequencing run and generates analysis reports in a matter of seconds. After detecting new fastq files (basecalled sequence output format of Nanopore sequencing), RTNano quickly aligns the reads to the targeted amplicons of the viruses. To confidently determined the existence of a virus, RTNano filters the alignment records by percentage identity and amplicon coverage and provides the number of positive records for each targeted viral amplicon, which is then used to evaluate the infection status of the sample.

When demultiplexing a large number of samples, barcode misclassification could potentially happen due to base-calling errors in the barcodes. RTNano included an additional round of demultiplexing using stringent parameters to reduce the chance of barcode misclassification (see methods section under “Examples”)). Furthermore, a no template control (NTC) was included to monitor barcode misclassification. The reads of targeted amplicons assigned to the NTC barcode likely represented background errors in demultiplexing. The positive record number of the NTC was subtracted from individual sample analysis to further reduce false positive identification. After the real-time analysis, RTNano generated a report for each of the 60 samples, including current read number, base number, and details of alignment positive records (FIG. 1E). To simplify the interpretation of the result, RTNano provided a summary score of SARS-CoV-2 based on predefined rules (Table 2).

TABLE 2

| Sample classification rules in RTNano analysis | |
|---|---|
| Mark | Condition |
| POS_3 | 3 regions >= 50 records |
| POS_2 | 2 regions >= 50 records<br>OR 1 region >= 50 records and 2 regions >= 5 |
| POS_1 | 1 region >= 20 records<br>OR 2 regions >= 5 records<br>OR 3 regions >= 1 record |
| POS_0 | only 1 region >= 1 and <20 records<br>or only 2 regions >= 1 and <5 records |
| NEG | all regions = 0 record<br>AND ACTB >= 1000 records |
| UNK (unknown) | all regions = 0 record<br>AND ACTB <= 1000 records |

SARS-CoV-2 positive samples (POS) were assigned a confidence level ranging from 0 to 3 (lowest to highest) based on the number of covered amplicons and corresponding positive records. When there is no record of SARS-CoV-2, the sample could be categorized as either negative (NEG), if there were enough records (>1000) of ACTB, or unknown (UKN), if there were insufficient records of ACTB. The introduction of the confidence level could improve the accuracy of diagnosis, which is in principle similar to the CT value of rRT-PCR but based on quantitative information of multiple amplicons. Since base calling and demultiplexing may lead to a brief delay, we refer to the workflow as Nanopore sequencing of Isothermal Rapid Viral Amplification for Near real-time Analysis (NIRVANA) (FIG. 1A).

Figure 3B:
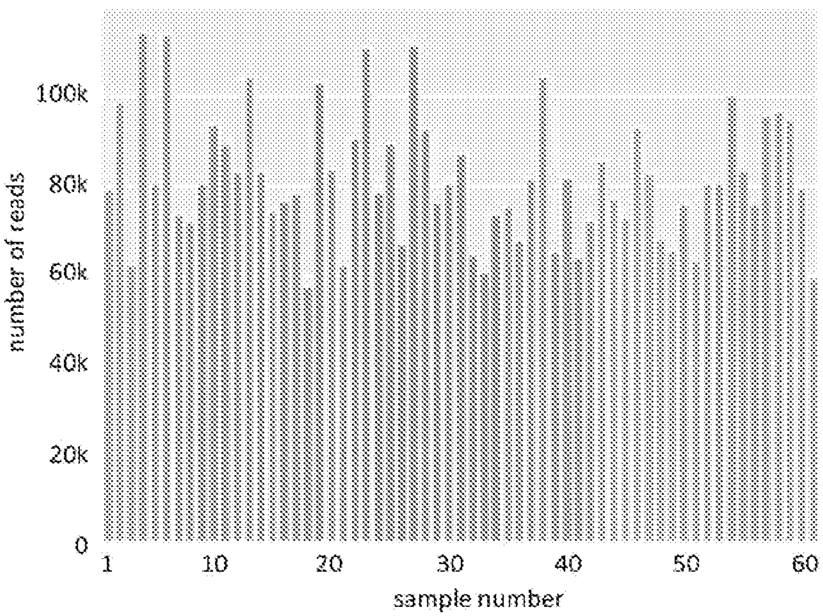
Figure 3C:
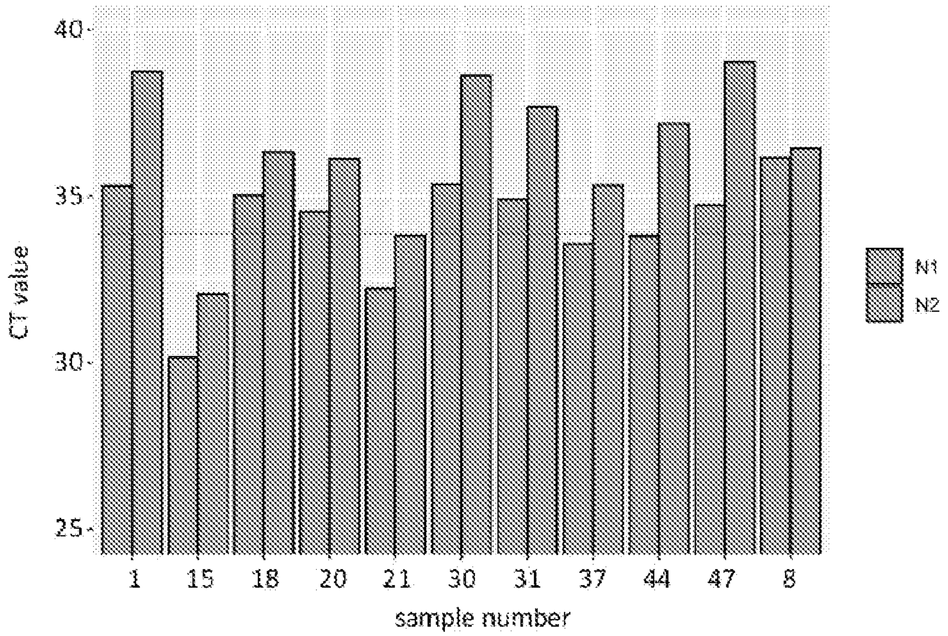

RTNano identified 35 SARS-CoV-2 positive cases in the 60 samples after 2 hours of Nanopore sequencing. Ten more positives were identified by RTNano (RTNano$^+$) as the data output increased in the next 22 hours of sequencing (FIG. 3B. An identical aliquot of each sample was analyzed in parallel using the US CDC rRT-PCR SARS-CoV-2 assays. Three samples were inconclusive after two rounds of rRT- PCR tests and were excluded in the downstream analysis. Among the 45 RTNano$^+$ samples, 43 had rRT-PCR confirmed status, in which 41 (95.35%) were positive by the rRT-PCR assay (PCR$^+$). The two remaining weakly RTNano$^+$ sample (POS_0) had high CT values of RNase P and failed in PCR amplification of N1 and N2. Three of the RTNano$^-$ samples were also PCR$^-$ due to no amplification of N1 and/or N2, while the rest of the 11 RTNano$^-$ were PCR$^+$. These 11 false-negative samples had high CT values (N1: 34.16±0.36, N2: 36.27±0.47, FIG. 3C). The incorrect identification of these samples could be due to amplification failure of multiplex RPA or insufficient sequencing throughput. In addition, high CT values in SARS-CoV-2 rRT-PCR tests have a higher chance of being false-positive (Katz et al., 2020; Surkova et al., 2020).

Figure 3D:
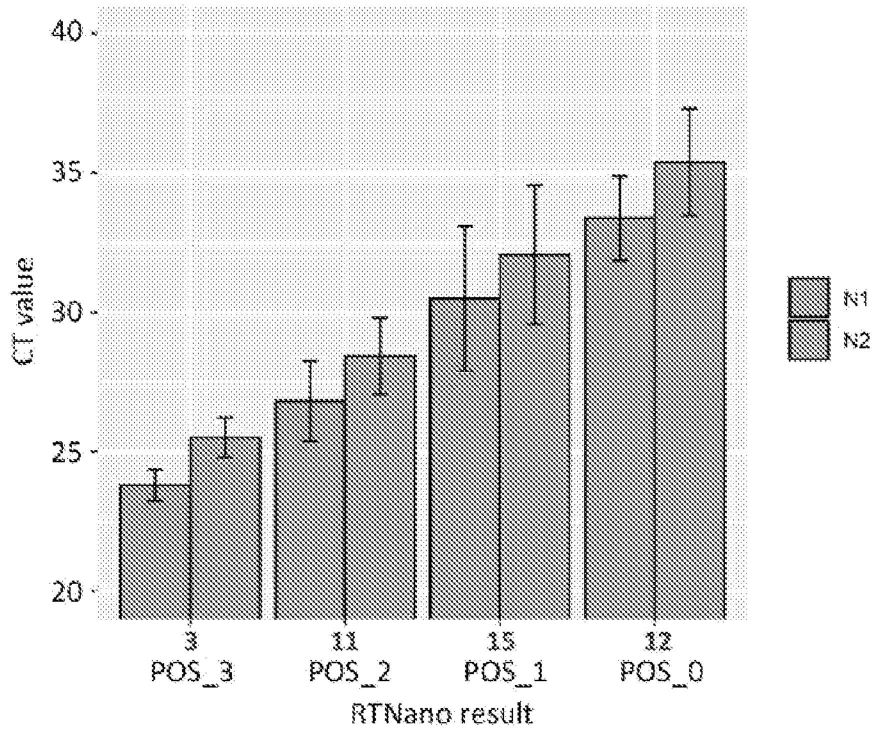

The average CT value of RTNano$^+$ samples was calculated under different confidence levels. RTNano$^+$ samples with high confidence level correlated with lower CT values, which proved the reliability of RTNano results (FIG. 3D). Based on the N1 standard curve, the limit of detection (LoD) of NIRVANA estimated was ~29 viral RNA copies/μl of extracted nucleic acid (86 copies per reaction, based on average N1 CT value of 33.37 of POS_0, and see as methods section under "Examples")), which was comparable to the current rRT-PCR assays[29].

Figure 3E:
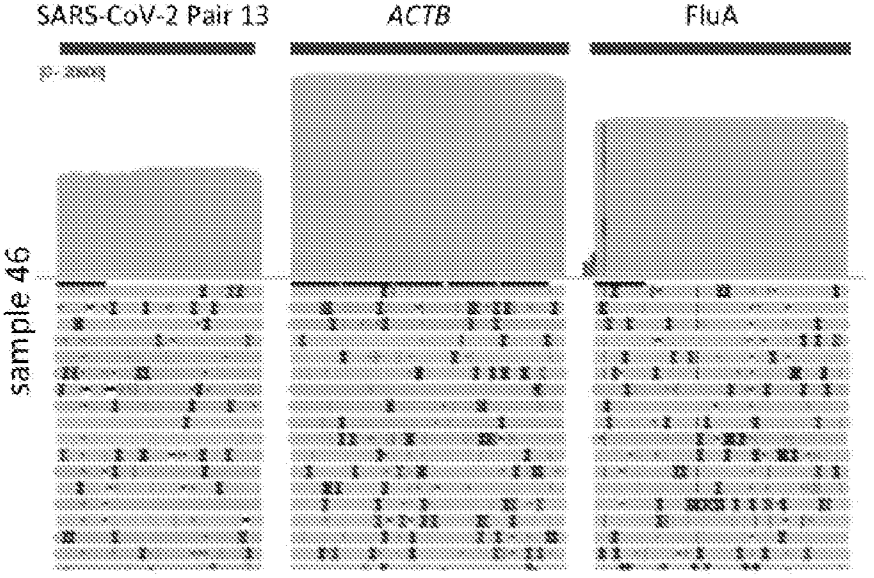
Figure 4E:
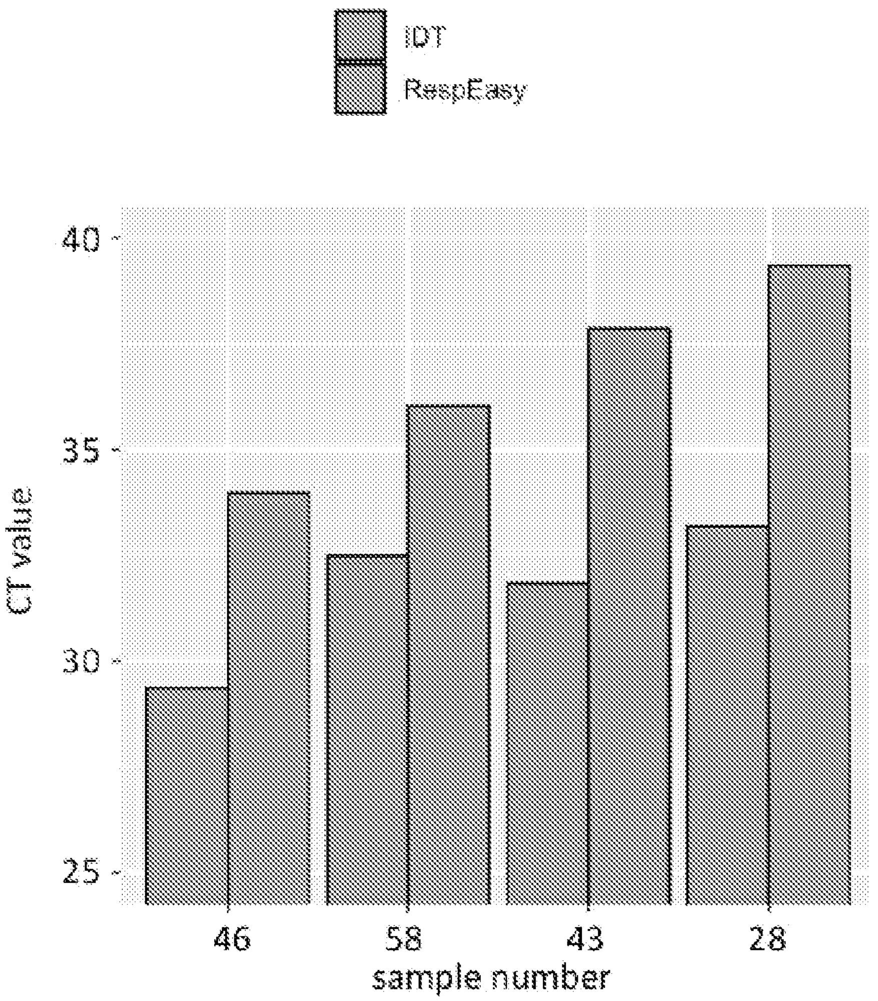

Co-infection of three common respiratory viruses in the 60 samples was studied, next. FluA co-infection was determined by two independent commercial rRT-PCR assays (Resp'Easy™ in vitro diagnostic kit (CE-IVD) and IDT influenza A,B/RSV identification kit). Four samples were identified as FluA$^+$ in both assays (CT value range: 33.97 to 39.33 by Resp'Easy™) (FIG. 4E). RTNano detected the FluA$^+$ sample with the lowest CT value (sample 46, CT 33.97) with high confidence (FIG. 3E). HAdVs and HCoV co-infection was examined using the Resp'Easy™ kit, and only one HCoV$^+$ sample was identified (Resp'Easy™ CT=35.18). RTNano reported no HAdVs co-infection and failed to detect the HCoV$^+$ sample.

Figure 4F:
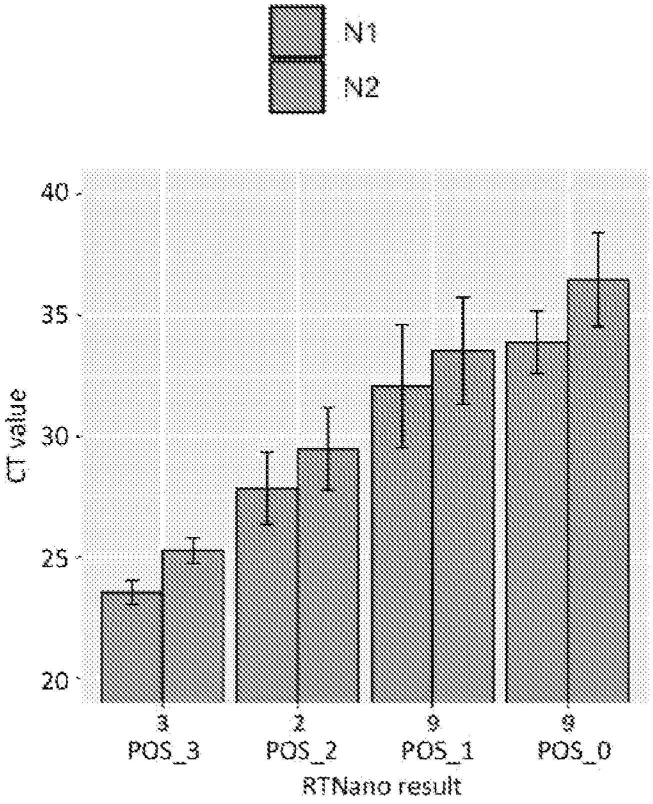

A high level of multiplexing reactions could negatively affect RPA efficiency of each amplicon. To test if a less complex primer combination could improve the performance of NIRVANA, we removed less robust SARS-CoV-2 primers (pair 9 & 10) and performed a new NIRVANA sequencing. Twenty-nine of the 60 samples were sequenced, including 11 RTNano$^-$/PCR$^+$, 4 FluA$^+$, and 1 HCoV$^+$. Nine of the previous 11 RTNano$^-$/PCR$^+$ samples were identified as SARS-CoV-2*, suggesting an improved sensitivity. To test if the remaining two RTNano$^-$/PCR$^+$ samples were true positives, we performed Nanopore sequencing of the PCR products of the two samples. The results showed that both samples contained high-confidence reads mapped to the expected amplicon sequences (data not shown). Thus, we concluded that these two samples were true positives. The average N1 CT value of POS_1 was improved from 30.48 to 32.06 (FIG. 4F). Using the new data, the LoD of SARS-CoV-2 of 7-amplicon NIRVANA was calculated to be ~20 viral RNA copies/μl of extracted nucleic acid (61 copies per reaction, based on average N1 CT value of 33.37 of POS_0).

Figure 4G:
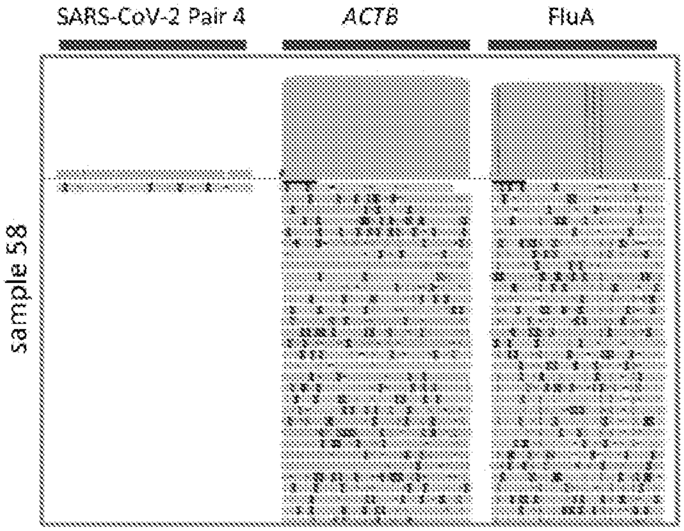

The sensitivity of FluA detection was also improved as two FluA$^+$ samples (Resp'Easy™ CT value of 33.97 and 36.03) were correctly identified (sample 46 & 58 in FIG. 4E, FIG. 4G). The HCoV$^+$ sample was still not identified. NIRVANA showed a robust ability in detecting HCoV in the positive control sample (FIG. 3A), suggesting that the HCoV in the clinical sample may belong to a different strain that could not be amplified by the HCoV primers used. Taken all together, these results showed that NIRVANA provided high-confident SARS-CoV-2 detection for virus loads above 20 copies/μl of extracted nucleic acid and reliable capability in detecting potential co-infections.

Figure 3F:
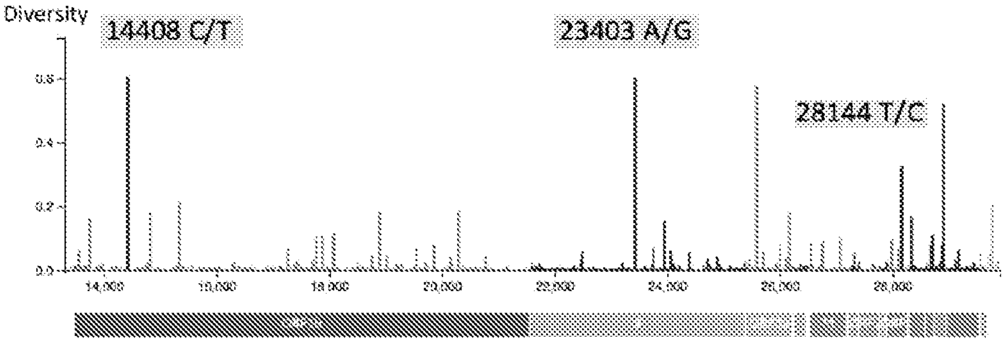

RTNano has an integrated function to quickly analyze variants in each sample during sequencing. It was used to analyze sequence variants in ten SARS-CoV-2 positive samples (FIG. 1D). It detected 16 single nucleotide variants (SNVs) in the ten samples and all of them had been reported in GISAID (FIG. 3F, as of Jun. 7, 2020). The reported SNVs suggested that the strains in samples 01-03 are close to clade 19B (nt28144 T/C), first identified in Wuhan, China, while the strains in samples 04-10 are close to clade 20 (nt14408 C/T, 23403 A/G), first becoming endemic in Europe. Given the fact that samples 01-03 were collected early in the pandemic, while the others were later (around May), the SNV signature of the strains revealed by NIRVANA is consistent with the pattern of COVID-19 case importation. Prospectively collecting such data regularly could guide public health policy making to better control the pandemic.

Figure 5A:
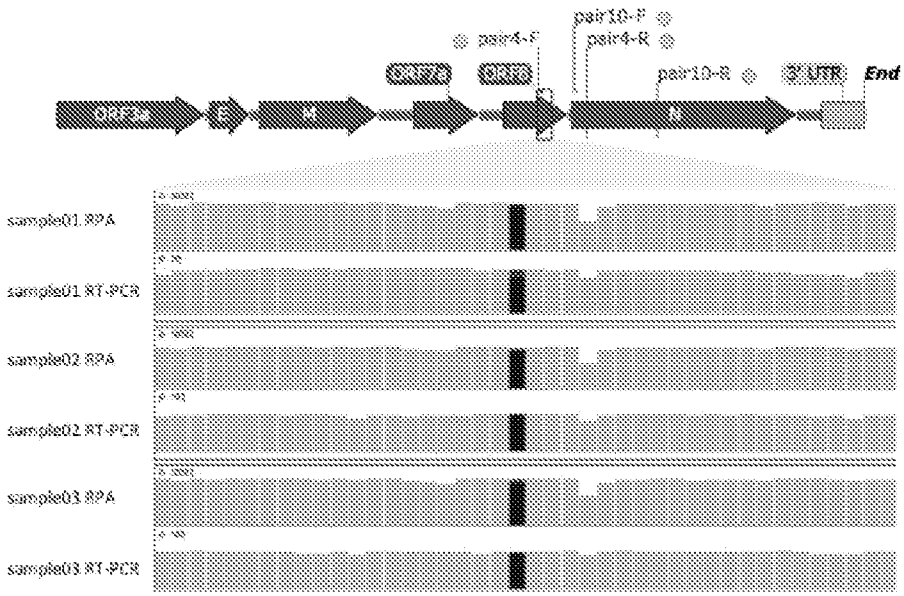
FIG. 5A-B show validation of SNVs detected by NIRVANA.

To validate the SNVs and compare NIRVANA with conventional RT-PCR amplicon sequencing[30], three samples (01-03) were chosen to perform multiplex RT-PCR amplicon sequencing on the Nanopore MinION. Variant calling was done by RTNano using the same parameters and the results showed that RT-PCR sequencing confirmed all 3 SNVs detected by NIRVANA (FIG. 5A). The SNVs of samples 01-03 were further compared with their corresponding assembled genome from Illumina sequencing published in GISAID (EPI_ISL_437459 for sample03, EPI_ISL_437460 for sample04, and EPI_ISL_437461 for sample05). All of the three SNVs existed in the assembled genome.

Taken together, NIRVANA provides high-confidence detection of both SARS-CoV-2 and other respiratory viruses, and mutation surveillance of SARS-CoV-2 on the fly. Compared to the Oxford Nanopore's official method termed LAMPore[31], which is based on RT-LAMP, NIRVANA offers several advantages including longer amplicons and higher level of multiplexing. LAMPore generated short amplicons (~80 bp), of which half were composed of primer sequences. Thus, the read alignment may be more prone to amplification artifacts that lead to false-positive results. In NIRVANA, significantly longer amplicons (up to 466 bp in this study) combined with alignment record filter significantly improve the accuracy of positive result by eliminating the influence of amplification artifacts. In addition, LAMP-based LAMPore requires multiple primers (at least 4) to amplify one amplicon, which is a challenging for multiplexing. In contrast, the studies disclosed herein showed that RPA-based NIRVANA can able to amplify and detect nine amplicons in one pot (FIG. 3A). It can therefore be used in detecting multiple viruses simultaneously to help monitor and treat patients.

Figure 2D:
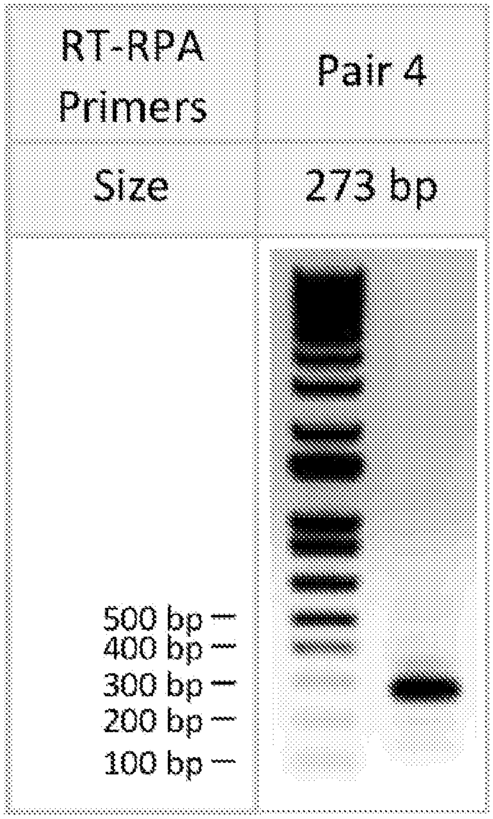
Figure 5B:
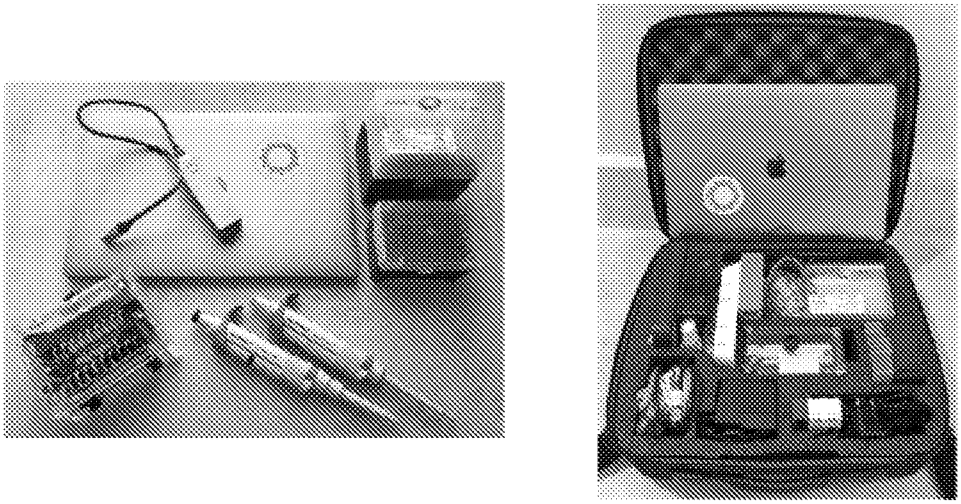

The whole workflow of NIRVANA can be further shortened by performing one-pot RT-RPA (FIG. 2D) so that the time from RNA to result can be as short as 3.5 hours. All molecular biology reactions in the workflow can be done in a simple heating block, and all necessary supplies fit into a briefcase (FIG. 5B). The framework of NIRVANA is built with flexibility of detecting other viruses by changing primers. Thus, NIRVANA provides a rapid field-deployable solution of pathogen detection and mutational surveillance of viral strains, including pandemic strains.

REFERENCES

1 WHO. *Naming the coronavirus disease* (*COVID*-19) *and the virus that causes it*, <https://www.who.int/emergencies/diseases/novel-coronavirus-2019/technical-guidance/naming-the-coronavirus-disease-(covid-2019)-and-the-virus-that-causes-it> (2020).

2 The nCo-V Outbreak Joint Field Epidemiology Investigation Team, Q., Li. An Outbreak of NCIP (2019-nCoV) Infection in China—Wuhan, Hubei Province, 2019-2020. *China CDC Weekly* 2, 79-80, doi:10.46234/ccdcw2020.022 (2020).

3 Wu, F., Zhao, S., Yu, B., Chen, Y. M., Wang, W., Song, Z. G., Hu, Y., Tao, Z. W., Tian, J. H., Pei, Y. Y., Yuan, M. L., Zhang, Y. L., Dai, F. H., Liu, Y., Wang, Q. M., Zheng, J. J., Xu, L., Holmes, E. C. and Zhang, Y. Z. Novel 2019 coronavirus genome. (2020).

4 Corman, V. M. et al. Detection of 2019 novel coronavirus (2019-nCoV) by real-time RT-PCR. *Euro Surveill* 25, doi:10.2807/1560-7917.ES.2020.25.3.2000045 (2020).

5 Centers for Disease Control and Prevention, R. V. B., Division of Viral Diseases. Real-Time RT-PCR Panel for Detection 2019—Novel Coronavirus. (2020).

6 Zhang, Y. Z. & Holmes, E. C. A Genomic Perspective on the Origin and Emergence of SARS-CoV-2. *Cell* 181, 223-227, doi:10.1016/j.cell.2020.03.035 (2020).

7 Lansbury, L., Lim, B., Baskaran, V. & Lim, W. S. Co-infections in people with COVID-19: a systematic review and meta-analysis. *J Infection* 81, 266-275, doi:10.1016/j.jinf.2020.05.046 (2020).

8 Babiker, A. et al. Metagenomic sequencing to detect respiratory viruses in persons under investigation for COVID-19. *J Clin Microbiol*, doi:10.1 128/JCM.02142-20 (2020).

9 Hashemi, S. A., Safamanesh, S., Zadeh-moghaddam, H. G., Ghafouri, M. & Azimian, A. High prevalence of SARS-CoV-2 and influenza A virus (H1N1) coinfection in dead patients in Northeastern Iran. *Journal of Medical Virology*, doi:10.1002/jmv.26364 (2020).

10 Notomi, T. et al. Loop-mediated isothermal amplification of DNA. *Nucleic acids research* 28, E63, doi:10.1093/nar/28.12.e63 (2000).

11 Zhang, Y. et al. Rapid Molecular Detection of SARS-CoV-2 (COVID-19) Virus RNA Using Colorimetric LAMP. *medRxiv,* 2020.2002.2026.20028373, doi:10.1101/2020.02.26.20028373 (2020).

12 Yan, C. et al. Rapid and visual detection of 2019 novel coronavirus (SARS-CoV-2) by a reverse transcription loop-mediated isothermal amplification assay. *Clin Microbiol Infect* 26, 773-779, doi:10.1016/j.cmi.2020.04.001 (2020).

13 Broughton, J. P. et al. CRISPR-Cas12-based detection of SARS-CoV-2. *Nature biotechnology*, doi:10.1038/s41587-020-0513-4 (2020).

14 Joung, J. et al. Point-of-care testing for COVID-19 using SHERLOCK diagnostics. *medRxiv,* 2020.2005.2004.20091231, doi:10.1101/2020.05.04.20091231 (2020).

15 Gardy, J. L. & Loman, N. J. Towards a genomics-informed, real-time, global pathogen surveillance system. *Nature reviews* 19, 9-20, doi:10.1038/nrg.2017.88 (2018).

16 Greninger, A. L. et al. Rapid metagenomic identification of viral pathogens in clinical samples by real-time nanopore sequencing analysis. *Genome Med* 7, 99, doi:10.1186/s13073-015-0220-9 (2015).

17 Bi, C. et al. Long-read Individual-molecule Sequencing Reveals CRISPR-induced Genetic Heterogeneity in Human ESCs. *bioRxiv,* 2020.2002.2010.942151, doi:10.1101/2020.02.10.942151 (2020).

18 Li, Y. et al. DeepSimulator1.5: a more powerful, quicker and lighter simulator for Nanopore sequencing. *Bioinformatics* 36, 2578-2580, doi:10.1093/bioinformatics/btz963 (2020).

19 Li, H. Minimap2: pairwise alignment for nucleotide sequences. *Bioinformatics* 34, 3094-3100, doi:10.1093/bioinformatics/bty191 (2018).

20 Li, H. et al. The Sequence Alignment/Map format and SAMtools. *Bioinformatics* 25, 2078-2079, doi:10.1093/bioinformatics/btp352 (2009).

21 Yin, C. Genotyping coronavirus SARS-CoV-2: methods and implications. *Genomics*, doi:10.1016/j.ygeno.2020.04.016 (2020).

22 Pachetti, M. et al. Emerging SARS-CoV-2 mutation hot spots include a novel RNA-dependent-RNA polymerase variant. *J Transl Med* 18, 179, doi:10.1186/si2967-020-02344-6 (2020).

23 Kim, D., Quinn, J., Pinsky, B., Shah, N. H. & Brown, I. Rates of Co-50 infection Between SARS-CoV-2 and Other Respiratory Pathogens. *Jama-JAm Med Assoc* 323, 2085-2086, doi:10.1001/jama.2020.6266 (2020).

24 Ma, L. et al. Coinfection of SARS-CoV-2 and Other Respiratory Pathogens. *Infect Drug Resist* 13, 3045-3053, doi:10.2147/IDR.S267238 (2020).

25 Medema, G., Heijnen, L., Elsinga, G., Italiaander, R. & Brouwer, A. Presence of SARS-Coronavirus-2 RNA in Sewage and Correlation with Reported COVID-19 Prevalence in the Early Stage of the Epidemic in The Netherlands. *Environmental Science & Technology Letters* 7, 511-516, doi:10.1021/acs.estlett.0c00357 (2020).

26 Kitajima, M., Sassi, H. P. & Torrey, J. R. Pepper mild mottle virus as a water quality indicator. *Npj Clean Water* 1, doi:ARTN 19 10.1038/s41545-018-0019-5 (2018).

27 Surkova, E., Nikolayevskyy, V. & Drobniewski, F. False-positive COVID-19 results: hidden problems and costs. *Lancet Respir Med*, doi:10.1016/S2213-2600(20)30453-7 (2020).

28 Katz, A. P. et al. False-positive reverse transcriptase polymerase chain reaction screening for SARS-CoV-2 in the setting of urgent head and neck surgery and otolaryngologic emergencies during the pandemic: Clinical implications. *Head Neck-J Sci Spec* 42, 1621-1628, doi:10.1002/hed.26317 (2020).

29 Vogels, C. B. F. et al. Analytical sensitivity and efficiency comparisons of SARS-CoV-2 RT-qPCR primer-probe sets. *Nat Microbiol* 5, 1299-+, doi:10.1038/s41564-020-0761-6 (2020).

30 Team, C.-I. Clinical and virologic characteristics of the first 12 patients with coronavirus disease 2019 (COVID-19) in the United States. *Nature medicine*, doi:10.1038/s41591-020-0877-5 (2020).

31 James, P. et al. LamPORE: rapid, accurate and highly scalable molecular screening for SARS-CoV-2 infection, based on nanopore sequencing. *medRxiv,* 2020.2008.2007.20161737, doi:10.1101/2020.08.07.20161737 (2020).

We claim:

1. A method for determining the presence of a viral nucleic acid in a sample comprising:

(i) contacting the sample with a plurality of primers specific to the nucleic acid, wherein the plurality of primers comprises one or more primers comprising a nucleic acid sequence having at least 90% sequence identity to any one of SEQ ID NOs: 2-11;

(ii) performing a single isothermal amplification reaction to simultaneously amplify a plurality of target regions in multiple viral nucleic acid; and (iii) detecting the amplification products, thereby determining the presence of the viral nucleic acid in the sample.

2. The method of claim 1, wherein the nucleic acid is derived from viruses, preferably a Severe acute respiratory syndrome-related coronavirus, influenza A, human adenovirus, and non-SARS-COV-2 human coronavirus.

3. The method of claim 1, wherein: (a) the Severe acute respiratory syndrome-related coronavirus is SARS-COV or SARS-COV-2; or (b) the plurality of primers comprises 7-9 pairs of primers and/or wherein the plurality of target regions comprises 7-9 target regions.

4. The method of claim 3 comprising 9 pairs of primers and/or 9 target regions.

5. The method of claim 4, wherein one or more of the target regions comprise genomic regions comprising signature mutations or mutation hotspots.

6. The method of claim 5, wherein one or more of the target regions are within the N gene, S gene, ORF1ab, or ORF8.

7. The method of claim 4, wherein the one or more primers comprise a nucleic acid sequence having the sequence of any one of SEQ ID NOs: 2-11.

8. The method of claim 1, wherein the single isothermal amplification reaction is an isothermal recombinase polymerase amplification (RPA).

9. The method of claim 1, further comprising characterizing the viral nucleic acid by a method comprising sequencing the amplification products and analyzing the sequences.

10. The method of claim 9, wherein the sequencing is performed using a Nanopore MinION.

11. The method of claim 9, wherein the analysis comprises aligning the sequences to a reference viral genome and determining the presence of one or more genetic variants in the sequences as compared to the reference.

12. The method of claim 11, wherein the variants comprise single nucleotide variants (SNVs), multiple nucleotide variants, indels, deletions or insertions larger than 50 bp, duplications or inversions, optionally, wherein one or more of the following SARS-CoV-2 SNVs are detected 28144 T/C, 14408 C/T, and 23403 A/G or the variant is the B.1.1.7 variant.

13. The method of claim 9, wherein the analysis is performed in real-time or near real-time.

14. The method of claim 1 performed on about 10-100 samples simultaneously.

15. The method of claim 1, wherein the method has a duration of about 0.5-4 hours.

16. A method for detecting the presence of a viral nucleic acid in a sample and one or more mutations therein, the method comprising:

(a) contacting the sample with a plurality of primers specific to the nucleic acid, wherein the plurality of primers comprises one or more primers comprising a nucleic acid sequence having at least 90% sequence identity to any one of SEQ ID NOs: 2-11;

(b) performing an isothermal recombinase polymerase amplification (RPA) on the sample to simultaneously amplify a plurality of target regions in multiple viral nucleic acid, thereby generating a plurality of amplification products;

(c) sequencing the amplification products;

(d) aligning the sequences to a reference viral genome or sequence, wherein existence of reads covering targeted amplicons indicates presence of the viral nucleic acid; and (e) determining the presence of one or more mutations in the sequences as compared to the reference.

17. A method of diagnosing a subject for infection with a virus comprising detecting the presence of a viral nucleic acid in a sample from the subject by the method of claim 1, wherein detecting the amplification products indicates the subjects is infected with the virus.

18. The method of claim 17, (a) wherein the subject exhibits or does not exhibit symptoms of a disease, disorder, or condition associated with the virus, and/or (b) further comprising treating the subject, wherein the subject was diagnosed as infected with the virus.

19. The method of claim 17, wherein the subject is human.

20. The method of claim 1, wherein the nucleic acid sample is derived from mucus, sputum (processed or unprocessed), bronchial alveolar lavage (BAL), bronchial wash (BW), cerebrospinal fluid (CSF), urine, tissue, rectal swab, nasopharyngeal aspirate, nasopharyngeal swab, throat swab, saliva, feces, mucosal excretions, plasma, serum, or whole blood.

* * * * *